US010832798B2

(12) United States Patent
Hubbell

(10) Patent No.: US 10,832,798 B2
(45) Date of Patent: *Nov. 10, 2020

(54) TIME-WARPED BACKGROUND SIGNAL FOR SEQUENCING-BY-SYNTHESIS OPERATIONS

(71) Applicant: LIFE TECHNOLOGIES CORPORATION, Carlsbad, CA (US)

(72) Inventor: Earl Hubbell, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 724 days.

This patent is subject to a terminal disclaimer.

(21) Appl. No.: 15/454,006

(22) Filed: Mar. 9, 2017

(65) Prior Publication Data

US 2017/0300616 A1    Oct. 19, 2017

Related U.S. Application Data

(63) Continuation of application No. 13/339,753, filed on Dec. 29, 2011, now Pat. No. 9,594,870.

(60) Provisional application No. 61/428,097, filed on Dec. 29, 2010.

(51) Int. Cl.
*G16B 40/00* (2019.01)
*G16B 30/00* (2019.01)

(52) U.S. Cl.
CPC .............. *G16B 40/00* (2019.02); *G16B 30/00* (2019.02)

(58) Field of Classification Search
CPC ................................. G16B 40/00; G16B 30/00
See application file for complete search history.

(56) References Cited

U.S. PATENT DOCUMENTS

| 4,384,273 A | 5/1983 | Ackland et al. |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,210,015 A | 5/1993 | Gelfand et al. |
| 5,399,491 A | 3/1995 | Kacian et al. |
| 5,587,128 A | 12/1996 | Wilding et al. |
| 5,750,341 A | 5/1998 | Macevicz |
| 5,854,033 A | 12/1998 | Lizardi |
| 6,033,546 A | 3/2000 | Ramsey |
| 6,054,034 A | 4/2000 | Soane et al. |
| 6,174,670 B1 | 1/2001 | Wittwer et al. |
| 6,210,891 B1 | 4/2001 | Nyren et al. |
| 6,258,568 B1 | 7/2001 | Nyren |
| 6,274,320 B1 | 8/2001 | Rothberg et al. |
| 6,399,952 B1 | 6/2002 | Maher et al. |
| 6,404,907 B1 | 6/2002 | Gilchrist et al. |
| 6,613,525 B2 | 9/2003 | Nelson et al. |
| 6,780,591 B2 | 8/2004 | Williams et al. |
| 6,828,100 B1 | 12/2004 | Ronaghi |
| 6,833,246 B2 | 12/2004 | Balasubramanian |
| 6,911,327 B2 | 6/2005 | McMillan et al. |
| 6,960,437 B2 | 11/2005 | Enzelberger et al. |
| 7,037,687 B2 | 5/2006 | Williams et al. |
| 7,049,645 B2 | 5/2006 | Sawada et al. |
| 7,133,782 B2 | 11/2006 | Odedra |
| 7,211,390 B2 | 5/2007 | Rothberg |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,535,232 B2 | 5/2009 | Barbaro et al. |
| 7,575,865 B2 | 8/2009 | Leamon et al. |
| 7,645,596 B2 | 1/2010 | Williams et al. |
| 7,695,907 B2 | 4/2010 | Miyahara et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,838,226 B2 | 11/2010 | Kamahori et al. |
| 7,875,440 B2 | 1/2011 | Williams et al. |

(Continued)

FOREIGN PATENT DOCUMENTS

| GB | 2461127 | 12/2009 |
| JP | 04-262799 | 9/1992 |

(Continued)

OTHER PUBLICATIONS

Ahmadian et al., "Pyrosequencing: History, biochemistry and future," *Clinica Chimica Acta*, 363:83-94 (2006).
Anderson et al., "A System for Multiplexed Direct Electrical Detection of DNA Synthesis," *Sensors and Actuators B: Chemical*, 129(1):79-86 (2008).
Balzer et al., "Characteristics of 454 pyrosequencing data—enabling realistic simulation with flowsim," *Bioinformatics*, 26:i420-i425 (2010).
Barbaro et al., "Fully electronic DNA hybridization detection by a standard CMOS biochip," *Sensors and Actuators B: Chemical*, 118:41-46 (2006).
Brockman et al., "Quality scores and SNP detection in sequencing-by-synthesis systems," *Genome Research*, 18:763-770 (2008).
Chapter 2, "Machine-Learning Foundations: The Probabilistic Framework", In: Baldi, P. and Brunak, S., *Bioinformatics: The Machine Learning Approach*, 2nd Edition, The MIT Press, 47-65 (2001).

(Continued)

*Primary Examiner* — John S Brusca
*Assistant Examiner* — Kaitlyn L Minchella
(74) *Attorney, Agent, or Firm* — Carolyn Koenig

(57) ABSTRACT

Methods for analyzing signal data generated by sequencing of a polynucleotide strand using a pH-based method of detecting nucleotide incorporation(s). In an embodiment, the method comprises formulating a function that models the output signal of a representative empty well of a reactor array. A time transformation is applied to the empty well function to obtain a time-warped empty well function. The time-warped empty well function is fitted to an output signal from the loaded well representative of a flow that results in a non-incorporation event in the loaded well. The fitted time-warped empty well function can then be used to analyze output signals from the loaded well for other flows.

20 Claims, 47 Drawing Sheets

(56) References Cited

U.S. PATENT DOCUMENTS

| | | |
|---|---|---|
| 7,888,013 B2 | 2/2011 | Miyahara et al. |
| 7,948,015 B2 | 5/2011 | Rothberg et al. |
| 8,673,627 B2 | 3/2014 | Nobile et al. |
| 2003/0219797 A1 | 11/2003 | Zhao et al. |
| 2004/0018506 A1 | 1/2004 | Koehler et al. |
| 2004/0197793 A1 | 10/2004 | Hassibi et al. |
| 2004/0197845 A1 | 10/2004 | Hassibi et al. |
| 2005/0084851 A1 | 4/2005 | Ronaghi et al. |
| 2006/0040297 A1 | 2/2006 | Leamon et al. |
| 2006/0147935 A1 | 7/2006 | Linnarsson |
| 2006/0147983 A1 | 7/2006 | O'uchi et al. |
| 2007/0059733 A1 | 3/2007 | Sundararajan et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2010/0035252 A1 | 2/2010 | Rothberg et al. |
| 2010/0075327 A1 | 3/2010 | Maxham et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1* | 12/2010 | Nobile ............... G01N 27/4145 205/775 |
| 2010/0301398 A1 | 12/2010 | Rothberg et al. |
| 2010/0304447 A1 | 12/2010 | Harris |
| 2010/0323348 A1 | 12/2010 | Hamady |
| 2010/0323350 A1 | 12/2010 | Gordon et al. |
| 2011/0183320 A1 | 7/2011 | Flusberg et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0173158 A1 | 7/2012 | Hubbell |
| 2013/0060482 A1 | 3/2013 | Sikora et al. |
| 2013/0090860 A1 | 4/2013 | Sikora et al. |

FOREIGN PATENT DOCUMENTS

| | | |
|---|---|---|
| WO | 1999/019717 | 4/1999 |
| WO | 1999/057321 | 11/1999 |
| WO | 2002/020837 | 3/2002 |
| WO | 2002/024322 | 3/2002 |
| WO | 2003/020895 | 3/2003 |
| WO | 2004/001015 | 12/2003 |
| WO | 2005/040425 | 5/2005 |
| WO | 2007/098049 | 8/2007 |
| WO | 2008/076406 | 6/2008 |
| WO | 2008/092150 | 7/2008 |
| WO | 2008/092155 | 7/2008 |
| WO | 2009/117119 | 9/2009 |
| WO | 2009/158006 | 12/2009 |
| WO | 2010/047804 | 4/2010 |
| WO | 2010/077859 | 7/2010 |
| WO | 2010/117804 | 10/2010 |
| WO | 2010/138182 | 12/2010 |
| WO | 2011/120964 | 10/2011 |
| WO | 2011/156707 | 12/2011 |
| WO | 2012/058459 | 5/2012 |
| WO | 2012/092515 | 7/2012 |

OTHER PUBLICATIONS

Eltoukhy et al., "Modeling and Base-Calling for DNA Sequencing-By-Synthesis," *2006 IEEE International Conference on Acoustics, Speech, and Signal Processing*, vol. 2, May 2006, II-1032-II-1035.

Finotello et al., "Comparative analysis of algorithms for whole-genome assembly of pyrosequencing data," *Briefings in Bioinformatics Advance Access*, 1-12 (Oct. 21, 2011).

Hammond et al., "Design of a single-chip pH sensor using a conventional 0.6-µm CMOS process," *IEEE Sensors Journal*, 4:706-712 (2004).

Heer et al., "Single-chip microelectronic system to interface with living cells," *Biosensors and Bioelectronics*, 22:2546-2553 (2007).

Hert et al., "Advantages and limitations of next-generation sequencing technologies: a comparison of electrophoresis and non-electrophoresis methods," *Electrophoresis*, 29(23):4618-26 (2008).

Hizawa et al., "Fabrication of a two-dimensional pH image sensor using a charge transfer technique," *Sensors and Actuators B: Chemical*, 117:509-515 (2006).

Hughes et al., "Chemical Microsensors," *Science*, 254:74-80 (1991).

Huse et al., "Accuracy and quality of massively parallel DNA pyrosequencing," *Genome Biology*, 8(7):R143.1-R143.9 (2007).

Ji et al., "BM-BC: A Bayesian method of base calling for Solexa sequence data," *Department of Biostatistics, The University of Texas M. D. Anderson Cancer Center*, Houston, Texas, U.S.A. (http://odin.mdacc.tmc.edu/~ylji/BMBC/bmbc-ie2.pdf), 1-27, 2010.

Kao, Wei-Chun et al., "BayesCall: A model-based base-calling algorithm for high-throughput short-read sequencing", *Genome Research*, vol. 19, 2009, 1884-1895.

Langaee et al., "Genetic variation analyses by Pyrosequencing," *Mutation Research*, 573: 96-102 (2005).

Leamon et al., "Cramming More Sequencing Reactions onto Microreactor Chips," *Chemical Reviews*, 107:3367-3376 (2007).

Ledergerber et al., "Base-calling for next-generation sequencing platforms," Briefings in Bioinformatics Advance Access, 12(5):489-497 (Jan. 18, 2011).

Lysholm et al., "FAAST: Flow-space Assisted Alignment Search Tool," *BMC Bioinformatics 2011*, 12:293 (http://www.biomedcentral.com/1471-2105/12/293), pp. 1-7 (2011).

Margulies, et al., "Genome sequencing in microfabricated high-density picolitre reactors", *Nature*, vol. 437, No. 15, Jul. 31, 2005, 376-380.

Margulies et al., Supplementary Methods for the article "Genome sequencing in microfabricated high-density picolitre reactors," *Nature*, 437:376-380 (2005), pp. 1-34.

Martinoia et al., "Development of ISFET array-based microsystems for bioelectrochemical measurements of cell populations," *Biosensors and Bioelectronics*, 16:1043-1050 (2001).

Massingham et al., "All Your Base: a fast and accurate probabilistic approach to base calling," *European Bioinformatics Institute, Wellcome Trust Genome Campus*, Hinxton, Cambridgeshire, UK (http://www.ebi.ac.uk/goldman-srv/AYB/references/ayb_revised.pdf), Oct. 26, 2011, 1-26.

Metzker, "Emerging technologies in DNA sequencing," *Genome Research*, 15:1767-1776 (2005).

Milgrew et al., "The development of scalable sensor arrays using standard CMOS technology," *Sensors and Actuators B: Chemical*, 103:37-42 (2004).

(56) References Cited

OTHER PUBLICATIONS

Milgrew et al., "A large transistor-based sensor array chip for direct extracellular imaging," *Sensors and Actuators B: Chemical*, 111-112:347-353 (2005).
Mir et al., "Integrated electrochemical DNA biosensors for lab-on-a-chip devices," *Electrophoresis*, 30:3386-3397 (2009).
PCT/US2011/067759, International Search Report and Written Opinion dated Jul. 4, 2012.
Pourmand et al., "Direct electrical detection of DNA synthesis," *Proc. Natl. Adac. Sci. U.S.A.*, 103(17):6466-6470 (2006).
Ronaghi, M. et al., "A Sequencing Method Based on Real-Time Pyrophosphate", *Science*, vol. 281, 1998, 363-365.
Ronaghi, "Pyrosequencing Sheds Light on DNA Sequencing," *Genome Research*, 11:3-11 (2001).
Svantesson et al., "A mathematical model of the Pyrosequencing reaction system," *Biophysical Chemistry*, 100:129-145 (2004).
Trojanowicz, "Recent developments in electrochemical flow detections—a review: part I. Flow analysis and capillary electrophoresis," *Anal. Chim. Acta*, 653(1):36-58 (2009).
Xu et al., "Integration of electrochemistry in micro-total analysis systems for biochemical assays: recent developments," *Talanta*, 80(1):8-18 (2009).
Yeow et al., "A very large integrated pH-ISFET sensor array chip compatible with standard CMOS processes," *Sensors and Actuators B: Chemical*, 44:434-440 (1997).
454 Sequencing System Software Manual Version 2.6 Part B : *GS Run Processor, GS Reporter, GS Run Browser, GS Support Tool*, available at http://genepool.bio.ed.ac.uk/Gene_Pool/454_software/Manuals/454SeqSys_SWManual-v2.6_PartB_May2011.pdf (last visited Aug. 31, 2012) (document dated May 2011).

\* cited by examiner

FIG. 2
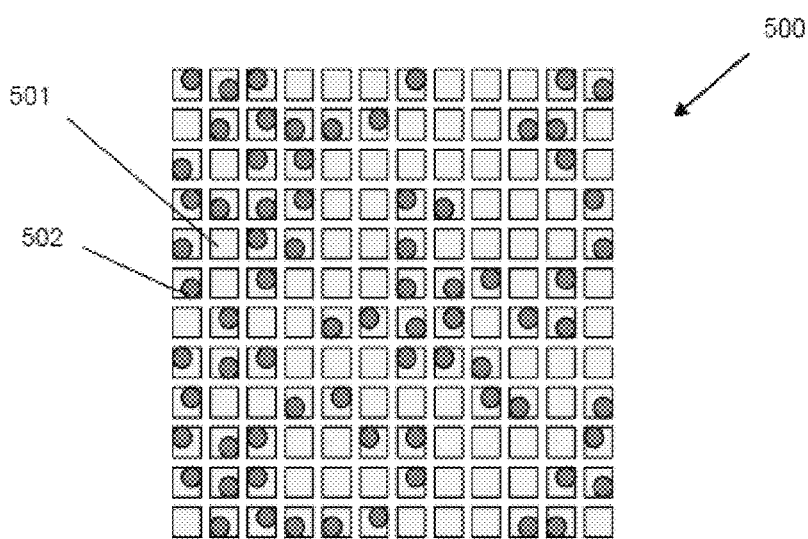
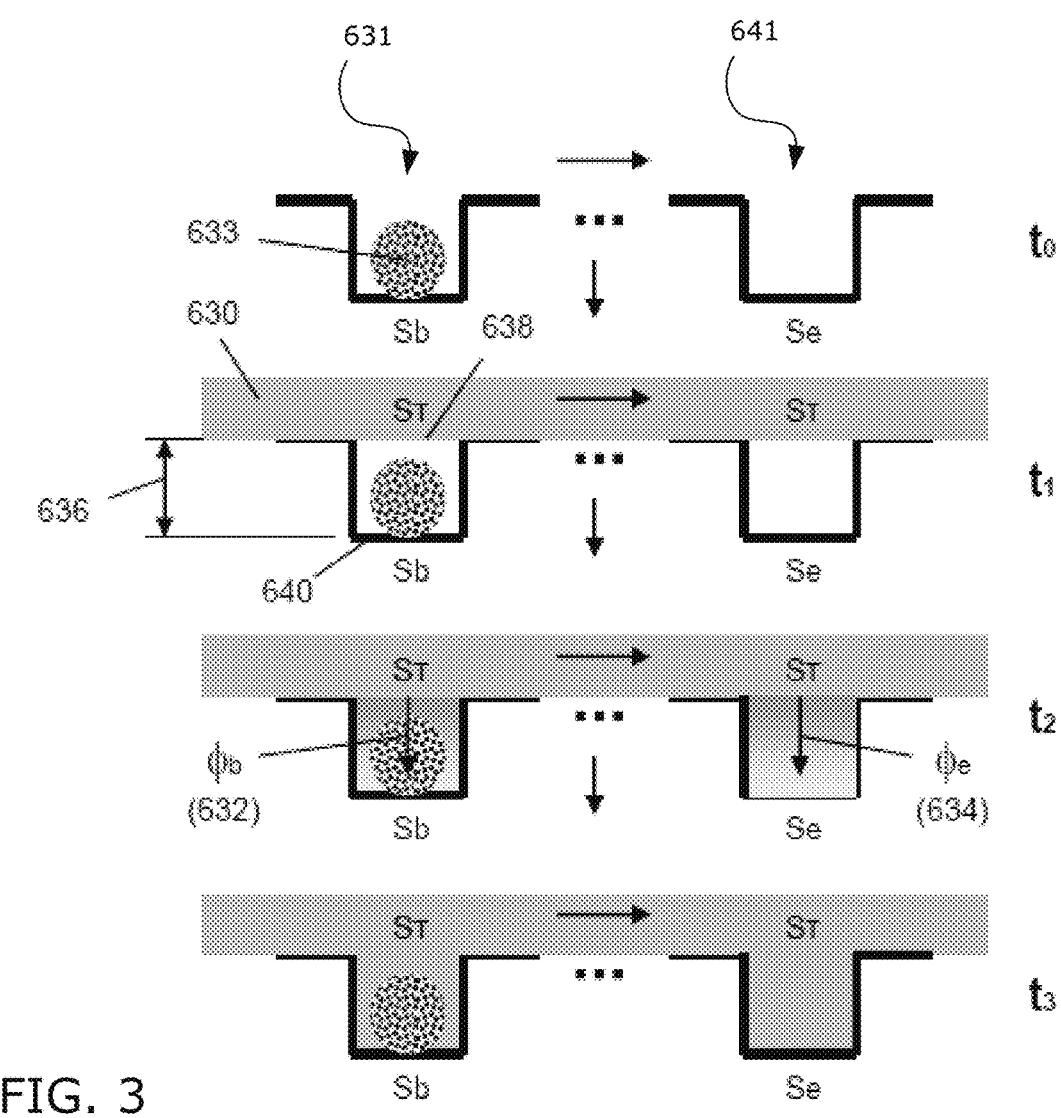
FIG. 3

TIME-WARPED BACKGROUND SIGNAL FOR SEQUENCING-BY-SYNTHESIS OPERATIONS

CROSS-REFERENCE TO RELATED APPLICATIONS

This application is a continuation of U.S. application Ser. No. 13/339,753 filed Dec. 29, 2011, which claims priority to U.S. application No. 61/428,097 filed Dec. 29, 2010, which disclosures are herein incorporated by reference in their entirety.

TECHNICAL FIELD

The present application generally relates to nucleic acid sequencing, and more particularly, to the processing of signals acquired from sequencing reactions.

BACKGROUND

Sequencing-by-synthesis is among a new generation of high throughput DNA sequencing technologies. Examples of techniques and platforms for sequencing-by-synthesis include the Genome Analyzer/HiSeq/MiSeq platforms (Illumina, Inc.; see e.g., U.S. Pat. Nos. 6,833,246 and 5,750,341); those applying pyrosequencing-based sequencing methods such as that used by Roche/454 Technologies on the GS FLX, GS FLX Titanium, and GS Junior platforms (see e.g., Ronaghi et al., SCIENCE, 281:363 (1998) and Margulies et al., NATURE, 437:376-380 (2005)); and those by Life Technologies Corp./Ion Torrent in the PGM™ system (see e.g., U.S. Patent Application Publication No. 2010/0137143 and No. 2009/0026082, which are both incorporated by reference herein in their entirety). There is a need for improved signal processing techniques to process signal data from nucleic acid sequencing, including from sequencing-by-synthesis operations.

BRIEF DESCRIPTION OF THE DRAWINGS

The accompanying drawings illustrate one or more exemplary embodiments of the present invention and serve to explain the principles of various exemplary embodiments. The drawings are exemplary and explanatory only and are not in any way limiting of the present invention.

FIG. 2 shows a random distribution of loaded wells and empty wells on an exemplary reactor array.

FIG. 3 shows two neighboring microwells and the diffusion of hydrogen ions into the microwells.

EXEMPLARY EMBODIMENTS

Figure 1:
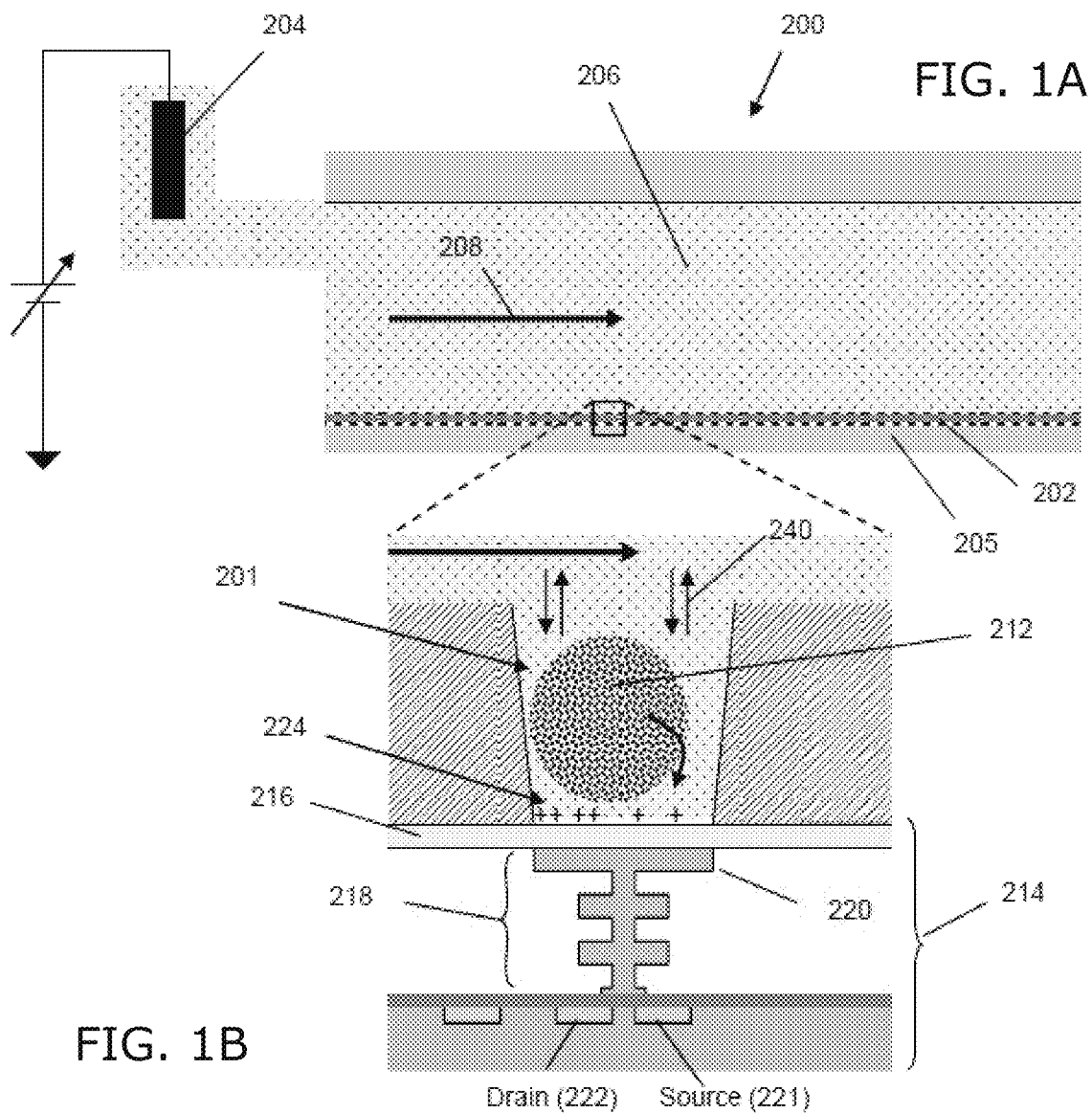
FIGS. 1A and 1B show an exemplary section of a flow cell and a microwell.

In various exemplary embodiments, one or more mathematical models may be used to process and/or analyze signal data from the sequencing of a template polynucleotide strand (e.g. by sequencing-by-synthesis).

In an exemplary embodiment, there is provided a method of sequencing a polynucleotide strand, comprising: (a) flowing a series of nucleotide reagents onto a reactor array having multiple reaction confinement regions, wherein the polynucleotide strand is located in a loaded reaction confinement region of the reactor array; (b) receiving signal data from the reactor array; (c) determining a function that models an output signal of a representative empty reaction confinement region; (d) determining a time-warped empty reaction confinement region function; and (e) estimating a number of nucleotide incorporations using the time-warped empty reaction confinement region function.

In some cases, the time-warped empty reaction confinement region function is determined by applying a time transformation to the empty reaction confinement region function. In some cases, the method further comprises fitting the time-warped empty reaction confinement region function to an output signal from the loaded reaction confinement region that is representative of a first flow, wherein the first flow results in a non-incorporation event in the loaded reaction confinement region. In some cases, the method further comprises applying the fitted time-warped empty reaction confinement region function to the output signal for a second flow to the loaded reaction confinement region to obtain an incorporation signal for the second flow. In some cases, the method further comprises analyzing the incorporation signal to determine an estimate of the number of nucleotides incorporated into the polynucleotide strand.

In some cases, the time transformation is a polynomial function of time. In some cases, the time transformation is a quadratic or cubic polynomial function of time. In some cases, the time transformation is a linear function of time. In some cases, the step of determining the empty reaction confinement region function comprises performing a spline fitting of the output signal from the representative empty reaction confinement region. In some cases, the empty reaction confinement region function is a polynomial function of time.

In some cases, the empty reaction confinement region function is an exponential function of time. In some cases, the representative empty reaction confinement region represents a plurality of empty reaction confinement regions within a region that includes the loaded reaction confinement region. In some cases, the reactor array includes a chemFET sensor array for detecting hydrogen ions in the reaction confinement regions of the array.

In some cases, the method further comprises fitting the time-warped empty reaction confinement region function to output signal from the loaded reaction confinement region representative of a third flow, wherein the third flow occurs later than the second flow and results in a non-incorporation event in the loaded reaction confinement region. In some cases, the time transformation comprises a parameter, and further comprising: obtaining an output signal from the loaded reaction confinement region that is representative of a third flow, wherein the third flow occurs later than the second flow and results in a non-incorporation event in the loaded reaction confinement region; obtaining a derivative of the output signal for the third flow; and adjusting the parameter of the time transformation using the derivative.

In some cases, the polynucleotide strand includes a portion having a known sequence, and wherein the first flow is over the portion having the known sequence. In some cases, the step of fitting the time-warped empty reaction confinement region function comprises minimizing the difference between the output signal from the loaded reaction confinement region and the signal predicted by the time-warped empty reaction confinement region function. In some cases, the incorporation signal is obtained by subtracting the time-warped empty reaction confinement region function from the output signal for the second flow. In some cases, the incorporation signal is obtained by solving a model for an output signal from the loaded reaction confinement region, wherein the output signal model comprises a background component and an incorporation signal component, wherein the background component is the fitted time-warped empty reaction confinement region function.

In some cases, the method further comprises: comparing the incorporation signal to a library of incorporation signal shapes comprising multiple signal shapes that are associated with different n-mer lengths; and based on the comparison, determining an estimate of the number of nucleotides incorporated into the polynucleotide strand. In some cases, the method further comprises using a catenary multi-compartment model to add to or generate or allow cross-referencing to the library of incorporation signal shapes, wherein the multi-compartment model comprises a series of two or more compartments that represent molecular locations on the homopolymer length. In some cases, the method further comprises: determining a function for the incorporation signal, wherein the function includes a parameter for the n-mer length; fitting the incorporation signal function to the incorporation signal to solve for the parameter for the n-mer length; and using the parameter for the n-mer length to estimate the number of nucleotides incorporated into the polynucleotide strand. In some cases, the method further comprises using a catenary multi-compartment model to determine the function for the incorporation signal. In some cases, the method further comprises using the time-warped empty reaction confinement region function to determine whether the loaded reaction confinement region is an outlier reaction confinement region.

In another exemplary embodiment, there is provided a sequencing apparatus comprising: a machine-readable memory; and a processor configured to execute machine-readable instructions, said instructions which when executed cause the apparatus to: (a) receive signal data relating to chemical reactions resulting from the flow of a series of nucleotide reagents onto a reactor array having multiple reaction confinement regions, wherein the polynucleotide strand is located in a loaded reaction confinement region of the reactor array; (b) determine a function that models an output signal of a representative empty reaction confinement region, wherein the function is stored in a computer memory; (c) determine a time-warped empty reaction confinement region function; (d) estimate a number of nucleotide incorporations using the time-warped empty reaction confinement region function; and (e) store the estimated number of nucleotide incorporations in the memory.

In another exemplary embodiment, there is provided a non-transitory machine-readable storage medium comprising instructions which, when executed by a processor, cause the processor to: (a) receive signal data relating to chemical reactions resulting from the flow of a series of nucleotide reagents onto a reactor array having multiple reaction confinement regions, wherein the polynucleotide strand is located in a loaded reaction confinement region of the reactor array; (b) determine a function that models an output signal of a representative empty reaction confinement region, wherein the function is stored in a computer memory; (c) determine a time-warped empty reaction confinement region function; (d) estimate a number of nucleotide incorporations using the time-warped empty reaction confinement region function; and (e) store the estimated number of nucleotide incorporations in the memory.

In an exemplary embodiment, there is provided a method for the processing and/or analysis of signal data generated by sequencing of a polynucleotide strand using a pH-based method of detecting nucleotide incorporation(s). The incorporation of nucleotide bases into the template polynucleotide strand may be detected by measuring the amount of hydrogen ions released from the polymerase-catalyzed incorporation reactions. Additional details of pH-based sequence detection systems and methods can be found in commonly-assigned U.S. Patent Application Publication No. 2009/0127589 and No. 2009/0026082, which are both incorporated by reference herein in their entirety.

The sequencing reactions may be carried out on reactor arrays, such as those described in U.S. Patent Application Publication No. 2010/0300559, No. 2010/0197507, No. 2010/0301398, No. 2010/0300895, No. 2010/0137143, and No. 2009/0026082, which are all incorporated by reference herein in their entirety. A reactor array may have multiple reaction confinement regions for localizing a reaction of interest. An example of a reaction confinement region is a well for containing the reaction reagents and/or analytes. Another example of a reaction confinement region is a discrete region of a surface of the array that can bind or otherwise directly or indirectly confine the reagents and/or analytes in or on such discrete region. As used herein, for more convenient terminology, the terms "well" and "microwell" are to be considered interchangeable with the term "reaction confinement region." The template polynucleotide strand can be confined to the reaction confinement region in various ways. For example, the template polynucleotide strand can be attached to a substrate particle (e.g. bead, microparticle, or other substrate moiety that fits inside wells of a reactor array or is directly or indirectly coupled to a surface of the reactor array). The particle may contain multiple identical copies (e.g. clonal) of the template polynucleotide strand.

The wells of the reactor array can be associated with sensors that detect hydrogen ions and produce an output signal (e.g. a change in voltage level or current level) based on the amount of hydrogen ions and/or changes thereof (i.e. a pH sensor). In an exemplary embodiment, the sensor may be a chemFET (chemical field-effect transistor) sensor that detects hydrogen ions to measure pH. The amplitude of the signals from the chemFET sensors may be related to the amount of hydrogen ions detected.

FIGS. 1A and 1B show an example of how the flow of a nucleotide reagent solution over a reactor array generates a signal. FIG. 1A shows a cross-sectional view of a portion 206 of a flow chamber on a flow cell 200. A nucleotide reagent solution is flowed (shown by arrow 208) over the microwells 202 of the reactor array. In this example, the array of microwells 202 is integrated with a sensor array 205 for detecting hydrogen ions. A reference electrode 204 is fluidly connected to flow cell 200.

FIG. 1B shows a close-up view of a microwell 201 of the reactor array. The microwell 201 contains a bead 212 that holds multiple identical copies of a template polynucleotide strand. Beneath the microwell 201 there is a chemFET sensor 214 for detecting hydrogen ions (and thus acting as a pH sensor) in the microwell 201 and generating an output signal. Sensor 214 includes a floating gate 218 having sensor plate 220 separated from the microwell interior by passivation layer 216. Sensor 214 is responsive to (and generates an output signal related to) the amount of charge 224 present on the passivation layer 216 opposite of sensor plate 220. Changes in charge 224 cause changes in the current between source 221 and drain 222 of the chemFET, which generates an output signal for the sensor 214.

The nucleotide solution moves into the microwell 201 by diffusion 240. If the nucleotide is complementary to the next base on the polynucleotide strand, then polymerase-catalyzed reactions with the polynucleotide strands on the bead 212 generate hydrogen ions that affect the amount of charge adjacent to sensor plate 220. The output signals from the sensors are collected and processed to estimate the number of nucleotides incorporated into the polynucleotide strand. With each successive flow of the nucleotide reagent, the output signal from the sensors may be collected over a time interval (e.g. in a continuous or intermittent manner).

A signal of interest in this example is the signal produced by the polymerase reaction-generated hydrogen ions. However, in addition to this signal of interest, there is also a background component of the measured output signal that results from other sources of pH changes. Since the bulk reagent solution used for the nucleotide flow also contains hydrogen ions, one of the sources of pH change in the wells is the diffusion of hydrogen ions from the bulk solution into the well as successive nucleotide reagent flows are passed over the reactor array (i.e. reagent change noise).

Having multiple wells, the reactor array may have some wells that contain substrate particles (e.g. beads) and other wells that are empty. The substrate particles may be dispersed randomly in the wells of the array. For example, the substrate particles may be flowed in a fluid onto the reactor array where they settle randomly into the wells. As a result, some wells may contain the particles whereas other wells may be empty. For example, FIG. 2 shows a random distribution of beads in a portion of a reactor array 500 having empty microwells 501 and loaded microwells 502.

Since an empty well on the reactor array does not contain a substrate particle (along with polynucleotide strands and polymerase that may be associated thereto), the signal in the empty well can be considered reflective of the pH changes that result from the background source, i.e., from the diffusion of hydrogen ions from the bulk solution into the well. To demonstrate this, FIG. 3 shows an example of the flux of hydrogen ions, represented as $\varphi_b$ (632), into a loaded well containing a bead 633 compared to the flux of hydrogen ions, represented as $\varphi_e$ (634), into an empty well. Two neighboring microwells, 631 and 641, are shown at four different times: before the next nucleotide reagent is introduced ($t_0$), immediately after the nucleotide reagent is flowed via the flow chamber 630 to the microwells ($t_1$), during equilibration of the nucleotide reagent with the microwell contents ($t_2$), and after equilibrium has been achieved ($t_3$). The change in sensor signal due to the reagent change can be described using a two compartment model, in which one compartment is the flow of nucleotide (shown by the horizontal arrow) in region 638 adjacent to the opening of a microwell and the other compartment is the surface 640 at the bottom of a microwell, located at a distance 636 from the opening of the microwell and adjacent to the sensor.

Figure 4:
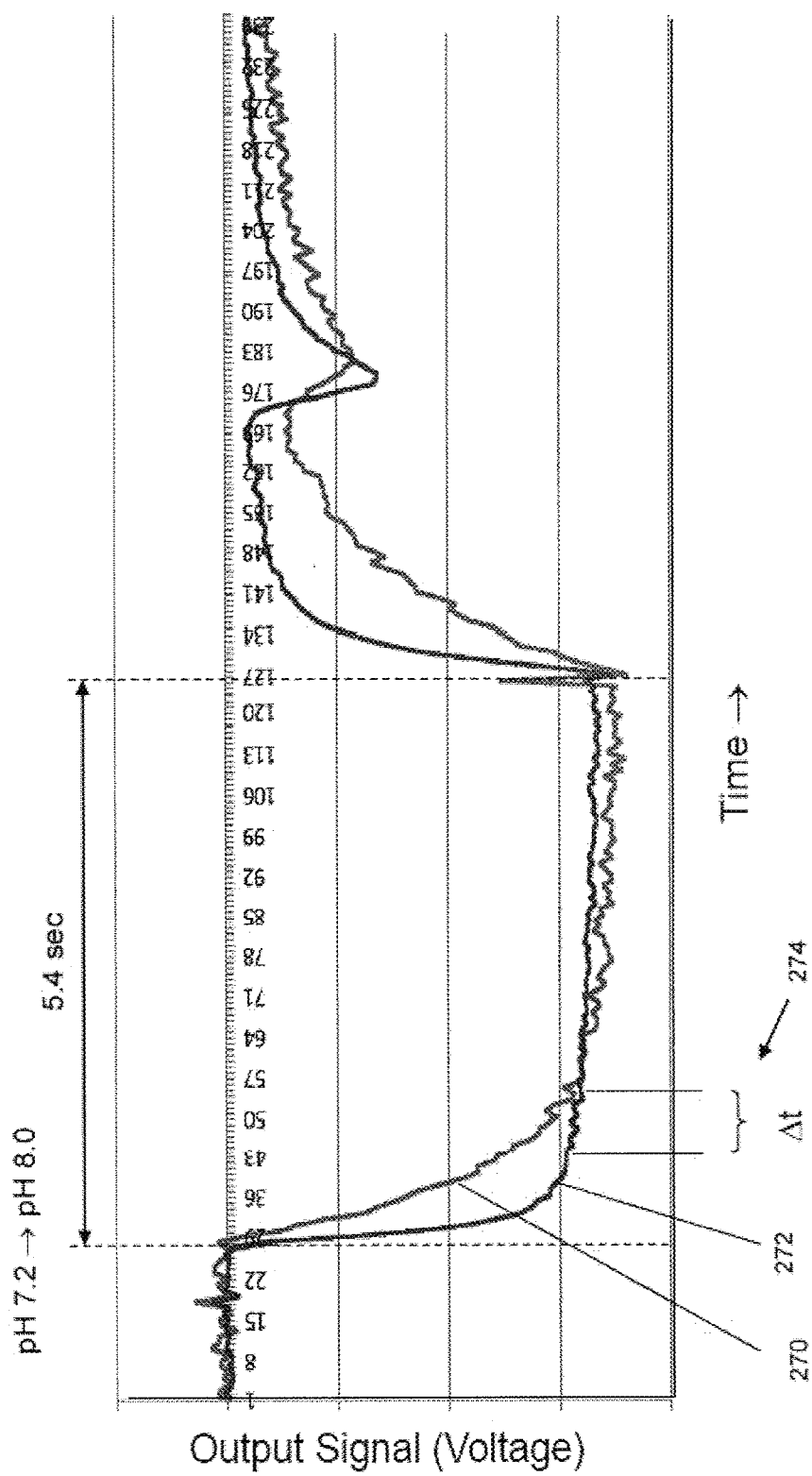
FIG. 4 shows a plot of signal voltage from a loaded well and from an empty well.
Figure 5B:
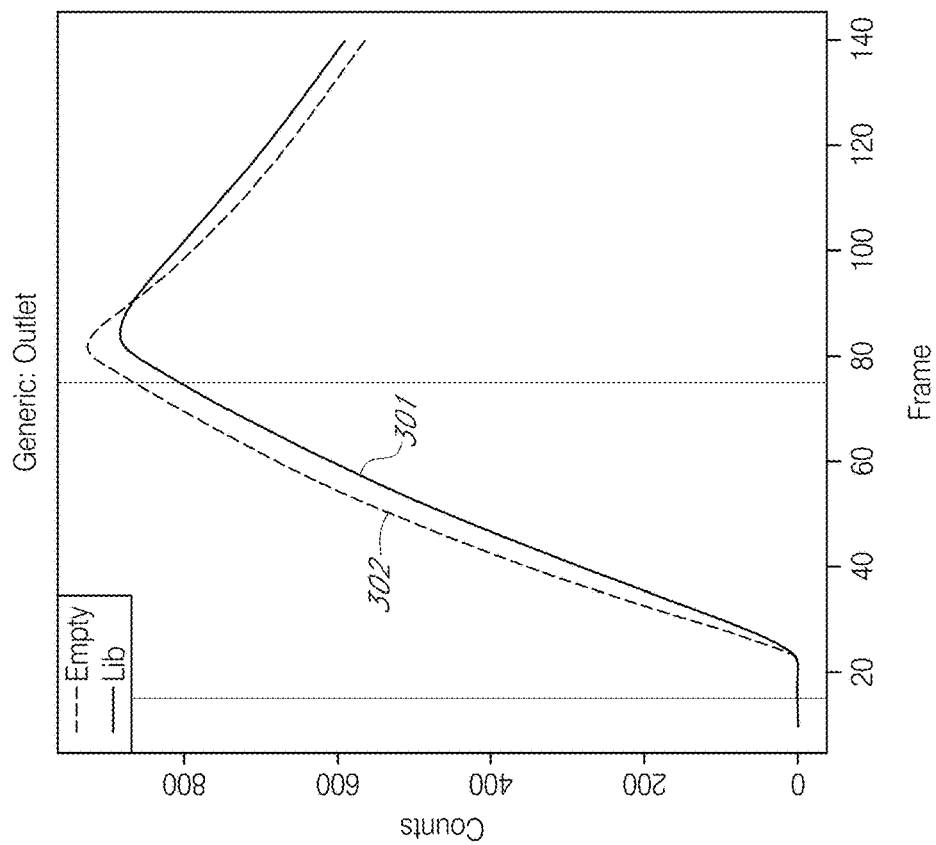
FIGS. 5A-5D show other examples of how the signal trajectory of empty wells may differ from loaded wells.
Figure 5A:
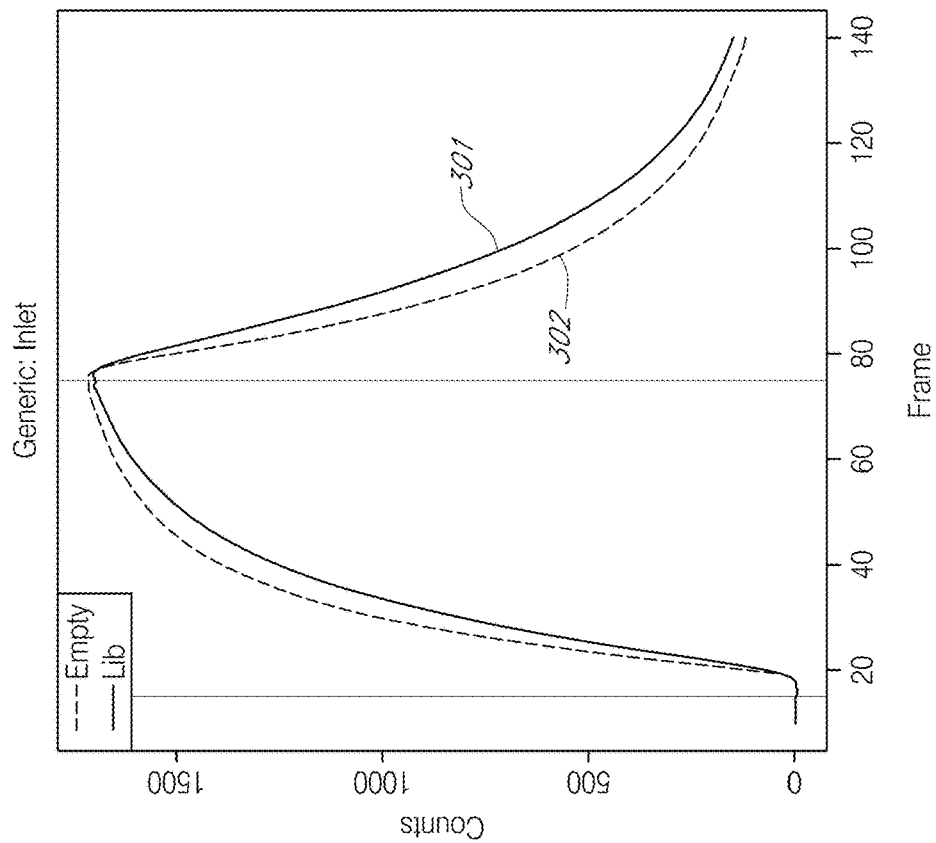
Figure 5C:
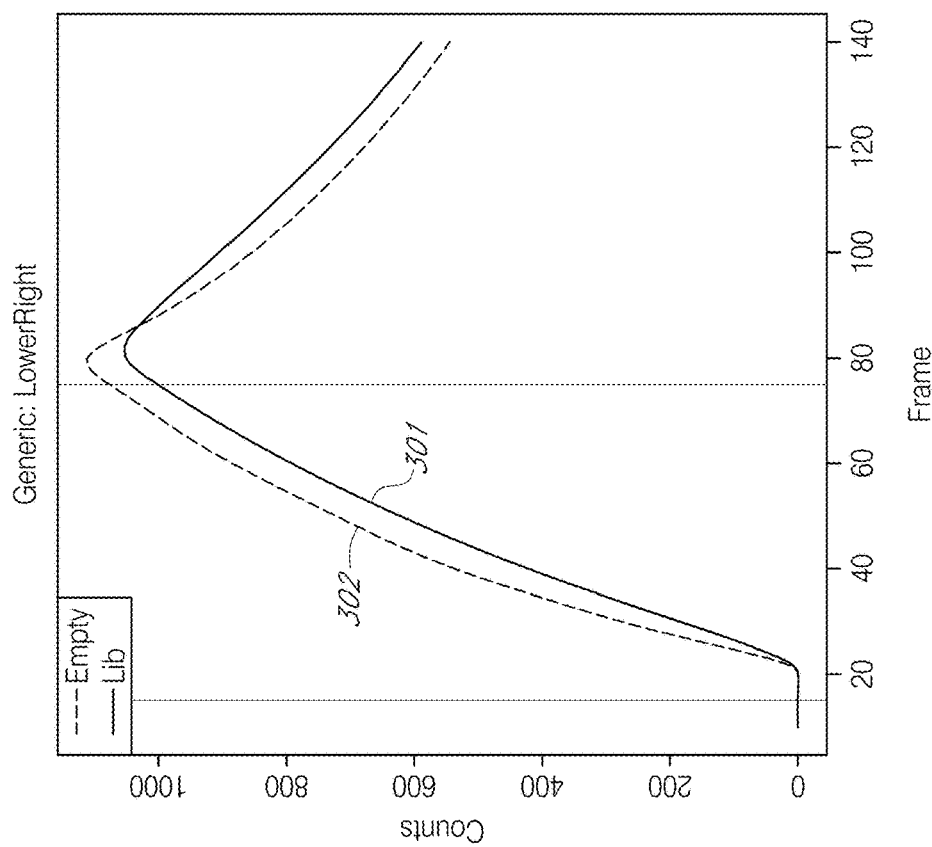
Figure 5D:
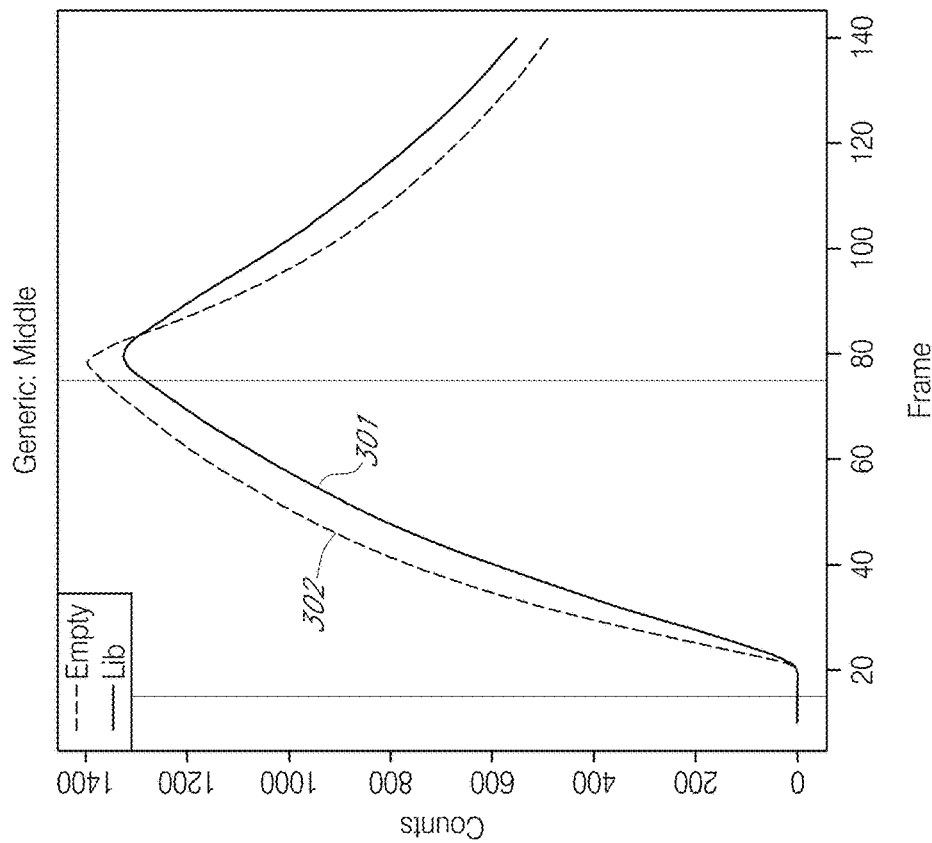

However, one of the potential complications in using an empty well signal as the background is that the loaded well may have various pH-buffering effects that are not present in the empty well. For example, the loaded well may have additional buffering capacity because of the substrate particle, the polynucleotide strands, and/or the polymerase enzymes, which may buffer the pH changes. As a result of this buffering effect, the signal count from the diffusion of hydrogen ions may rise faster in an empty well than in a loaded well. This is demonstrated in FIG. 4, which shows a plot of signal voltage from a loaded well (curve 270) and from an empty well (curve 272). The output voltage from the sensor in each well changes when the nucleotide reagent is flowed. Both curves show the signal change with the reagent flow. However, the signal curve 272 for the empty well changes at a faster rate than the signal curve for the loaded well. In other words, the signal curve from the loaded well lags the signal curve from the empty well. The difference in time, $\Delta t$(274), at which the respective output signals reach the plateau can be readily determined with conventional data analysis techniques.

FIGS. 5A-5D show other examples of how the signal trajectory of empty wells may differ from loaded wells. Each of FIGS. 5A-5D show the signal response from different wells located at different regions of a reactor array. As seen here, wells in different regions of the reactor array may have different signal responses. For example, a well located at the inlet of the flow chamber (see FIG. 5A) may have a faster signal response than a well located at the outlet of the flow chamber (see FIG. 5B). In each of FIGS. 5A-5D, curve 301 represents the signal from a loaded well whereas curve 302 represents the signal from an empty well. As seen here, the signal response curve 301 from the loaded wells lag the signal response curve 302 from the empty wells.

Because of this offset in the empty well signal curve, simply subtracting this empty well signal as background signal may not give an accurate estimate of the signal of interest. In an exemplary embodiment, for a more accurate representation of the background signal, the signal curve from an empty well may be transformed along the time axis for improved alignment with the signal curve of the loaded well. This approach may be useful where systematic differences account for the differences in the background signal in different wells. The present invention adjusts for this systematic difference to apply the background signal from an empty well to a loaded well. For example, it may be useful to consider that the signal response in the loaded wells are offset from the signal response of empty wells by a time lag, but reaching the same count at a later time.

In an exemplary embodiment, the output signal from a representative empty well is subject to a time transformation (which may be referred to as a "time warp") function to be used as an estimate of the background signal in a loaded well. The empty well here is identified as a representative empty well because the signal data may be from a single empty well or an estimate from multiple empty wells as representative of an empty well. The signal data from multiple empty wells may be subject to any suitable statistical analysis to obtain a single value as a representative estimate that quantitatively summarizes the collection of signal data, including calculating an average, a weighted average, some function of the average, a mean, a mode, or applying some other transformation function to the signal data, for example.

Figure 6A:
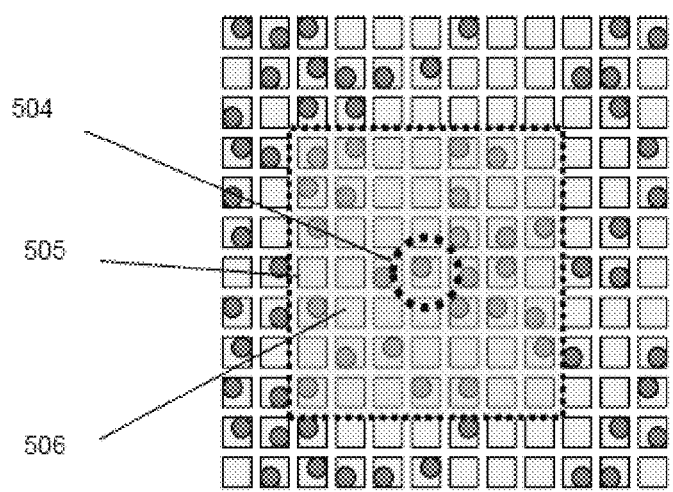
FIGS. 6A and 6B show examples of neighborhood regions on an exemplary reactor array.
Figure 6B:
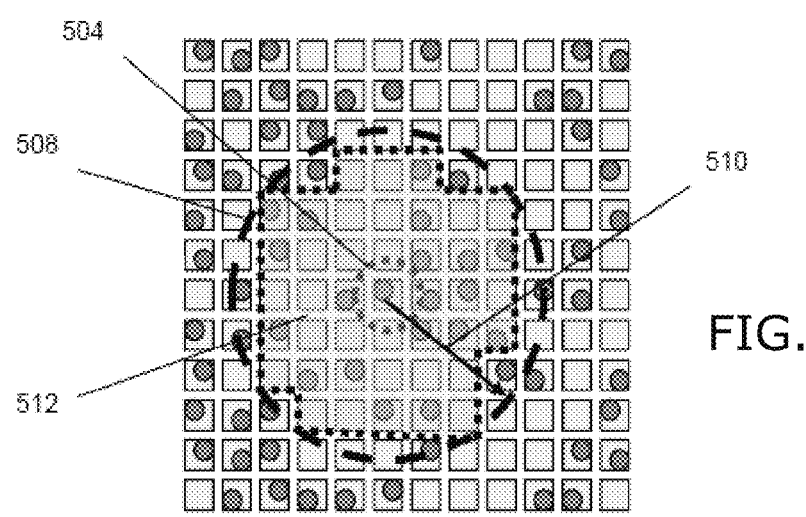

In cases where multiple empty wells are used, the empty wells may be in a region of the reactor array that includes the loaded well of interest (e.g. empty wells in a neighborhood around the well of interest). FIGS. 6A and 6B show examples of how regions for selecting empty wells can be defined. FIG. 6A shows a loaded well of interest 504 and a region 506 defined by a 7×7 square 505 of microwells. The size of the region may vary and may be selected on the basis of various factors, such as the relative number of loaded wells and its burden on computation time. In another example, FIG. 6A shows a region 512 defined by a circle 508 having a radius 510 from the microwell of interest 504. Not all of the empty well signals in a given region need be used. In some circumstances, it may be advantageous to minimize the number of empty well output signals being used in order to minimize computation time. For example, a random selection of available empty wells within a region may be used.

The output signal from the representative empty well may be described by a mathematical function that models the signal curve. For example, the function may represent the signal count as a function of time. Any suitable curve fitting technique may be used to construct a mathematical function that fits the signal data, including interpolation or smoothing techniques. For example, the signal data may be approximated by a spline function or polynomial approximation (e.g. an exponential function that approximates the signal curve). The empty well function may be a smooth function and/or a monotone function.

Having this mathematical function for the output signal from a representative empty well, a time transformation may be applied to this empty well function to fit the empty well function to signal data that is representative of a non-incorporation event in the well of interest. In this context, the term "non-incorporation event" means that the nucleotide flow does not result in any significant incorporation reactions (also referred to herein as "0-mer flows"). However, there may be non-significant incorporation reactions due to errors such as phase loss effects or misincorporations.

The signal data from the non-incorporation flow may be identified as being representative because it can be signal data from a single 0-mer flow or from multiple 0-mer flows. The signal data from multiple 0-mer flows may be subject to any suitable statistical analysis to obtain a single value as a representative estimate that quantitatively summarizes the collection of signal data, including calculating an average, a weighted average, some function of the average, a mean, a mode, or applying some other transformation function to the signal data, for example. Where multiple 0-mer flows are used, the fitting may be applied to each 0-mer flow individually to obtain a representative estimate (e.g. by taking the average of the fitting results), or the fitting may be applied to the multiple 0-mer flows collectively (e.g. an average of the signal data from multiple 0-mer flows) to obtain the representative estimate.

The non-incorporation signal can be obtained by any suitable manner. For example, the non-incorporation flows may be those over known base sequences (e.g. key sequences or other known part of the polynucleotide sequence) that are expected to produce non-incorporation events because they are non-complementary to the nucleotide being flowed. In another example, the non-incorporation signal can be produced by immediately repeating the same nucleotide flow (e.g. double tapping). Since the complementary nucleotides would have already incorporated in the prior flow, the subsequent flow of the same nucleotide would not be expected to result in any further nucleotide incorporations.

Any suitable time transformation may be applied to the empty well function to remap the time scale of the empty well function, resulting in a time-warped empty well function. For example, if the empty well function can be expressed by the function $z(t)$, then a time warping function can be applied to $z(t)$ to give $z(g(t))$, where $g(t)$ describes the changed time scale feeding into the function $z(t)$. The transformation may alter the time scale in a linear or non-linear manner.

In an exemplary embodiment, the function $g(t)$ may be a constant rescaling factor a such that the resulting transformed empty function is $z(a \cdot t)$. As a result, the time-warped empty well function is rescaled on the time axis (e.g. compressed or stretched), but otherwise has the same functional form. The time warping function $g(t)$ is not necessarily linear, however, and in some cases, the time warping function $g(t)$ may be non-linear (e.g. a quadratic function).

The fitting of the time-warped empty well function to the output signal that is representative of a non-incorporation event may be performed in any suitable manner, such as regression analysis or Bayesian techniques. The fitting may involve an iterative process of varying the parameter(s) of the time-warped empty well function to improve the fit (e.g. obtaining the best fit by minimizing the residual error sums) between the predicted signal curve and the measured signal curve. For example, the fitting may involve a least squares analysis of the signal curves and an optimization algorithm is applied to find a best-fitting solution. In some cases, this may be accomplished by defining an objective function for the difference between the two curves and optimizing this as a function of the parameter(s).

Figure 7B:
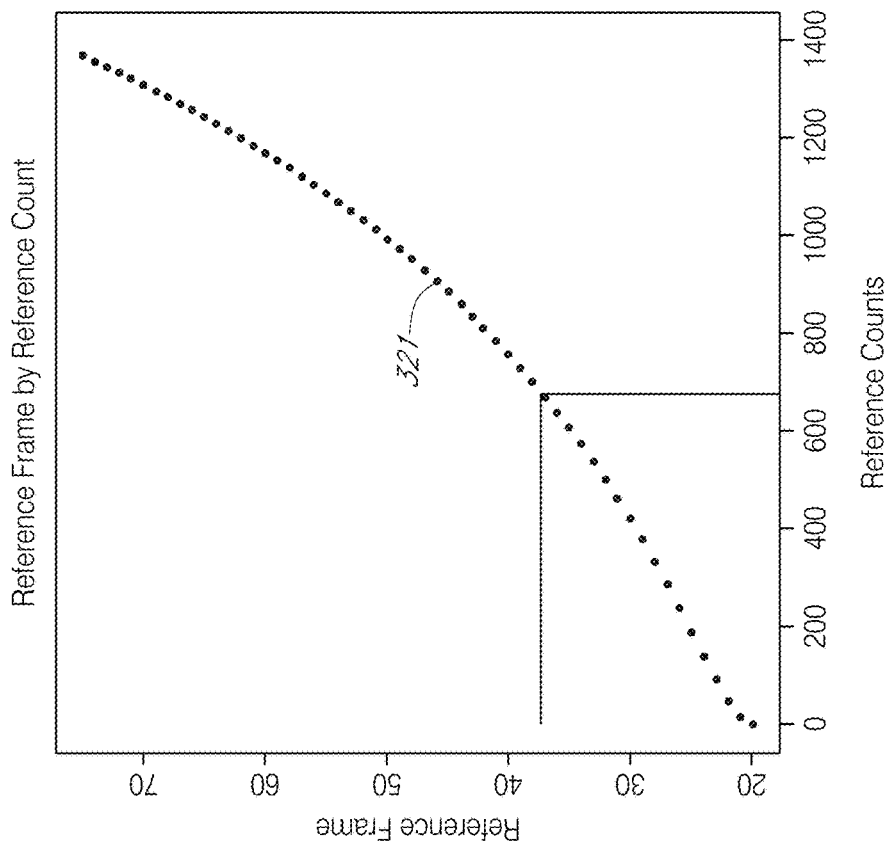
FIGS. 7A-7D demonstrate how a quadratic time warping may be applied to an empty well signal curve.
Figure 7A:
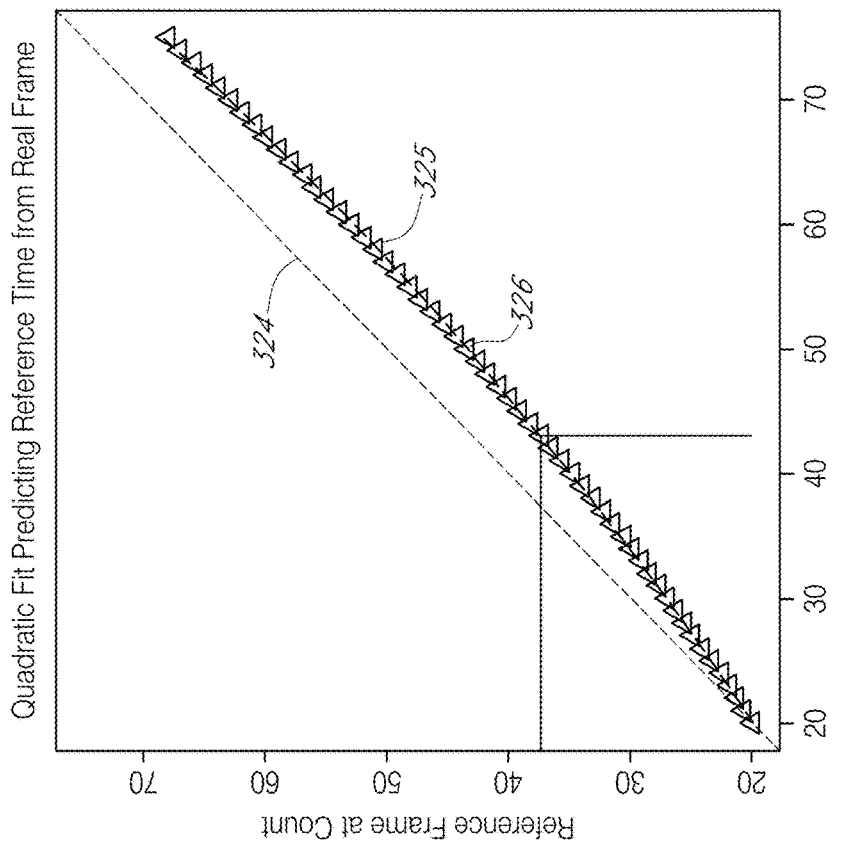
Figure 7D:
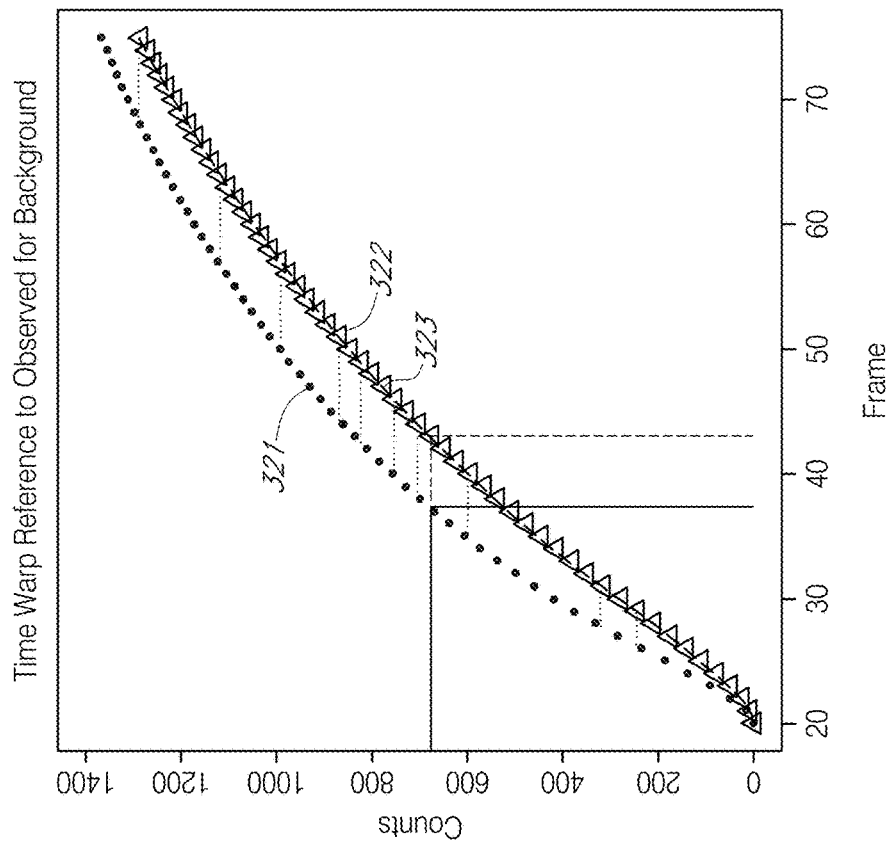
Figure 7C:
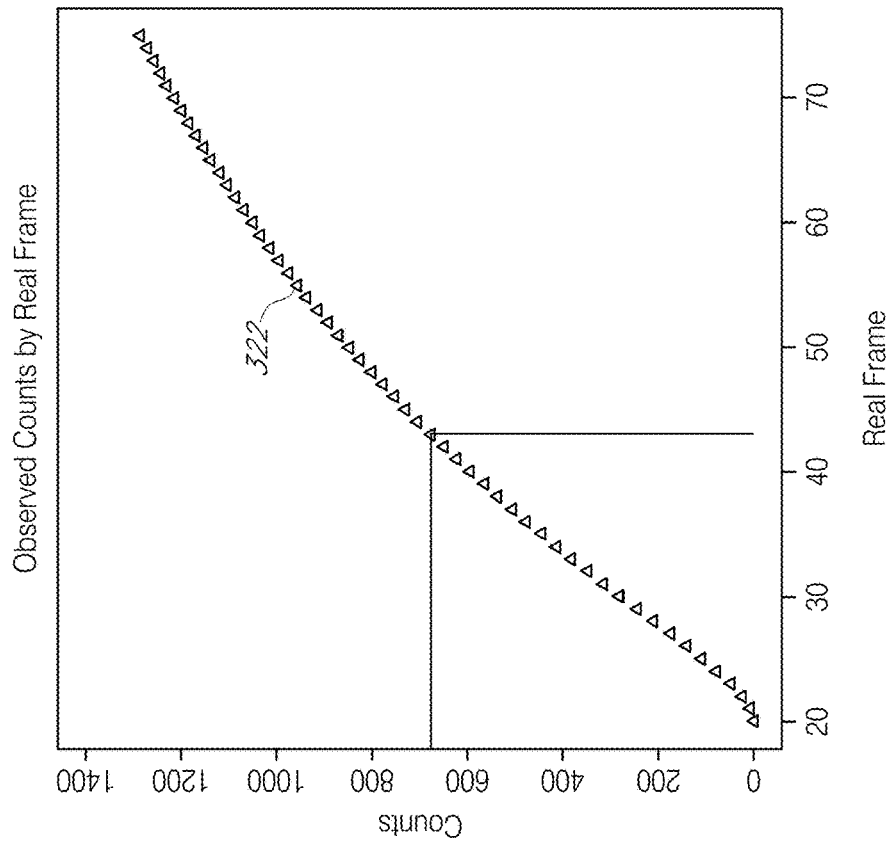

In an exemplary embodiment, the time transformation may be a polynomial function of time. For example, the transformation may be a function of a first (linear), second (quadratic), or third degree polynomial (cubic). FIGS. 7A-7D demonstrate how a time warping function of a second degree (quadratic) polynomial may be applied. FIG. 7B plots a signal response curve 321 of an empty well. FIG. 7D plots the signal response curve 321 of the empty well and the signal response curve 322 (triangles) of a loaded well subjected to a 0-mer flow. There may be a systematic difference between curve 321 (empty well) and 322 (loaded well). This systematic difference may be quantified by considering the frames at which the empty well and the loaded well reach the same signal count. As seen here, the empty well reaches a signal count of 650 at frame 37, whereas the loaded well reaches this signal count later at frame 43. For further consideration of this relationship, FIG. 7A plots where each point matches reference frames and real frames along line 325 (triangles; line 324 is a straight line that represents a linear plot for reference purposes). Line 326 is a quadratic polynomial that approximates this relationship (line 325). Thus, as shown in FIG. 7D, this quadratic polynomial may be used as the transformation function $f(t)$ to time warp the empty well signal response curve 321 so that it aligns with the loaded well signal response curve 322. The time-warped signal response curve for the empty well is shown by line 323.

Figure 8B:
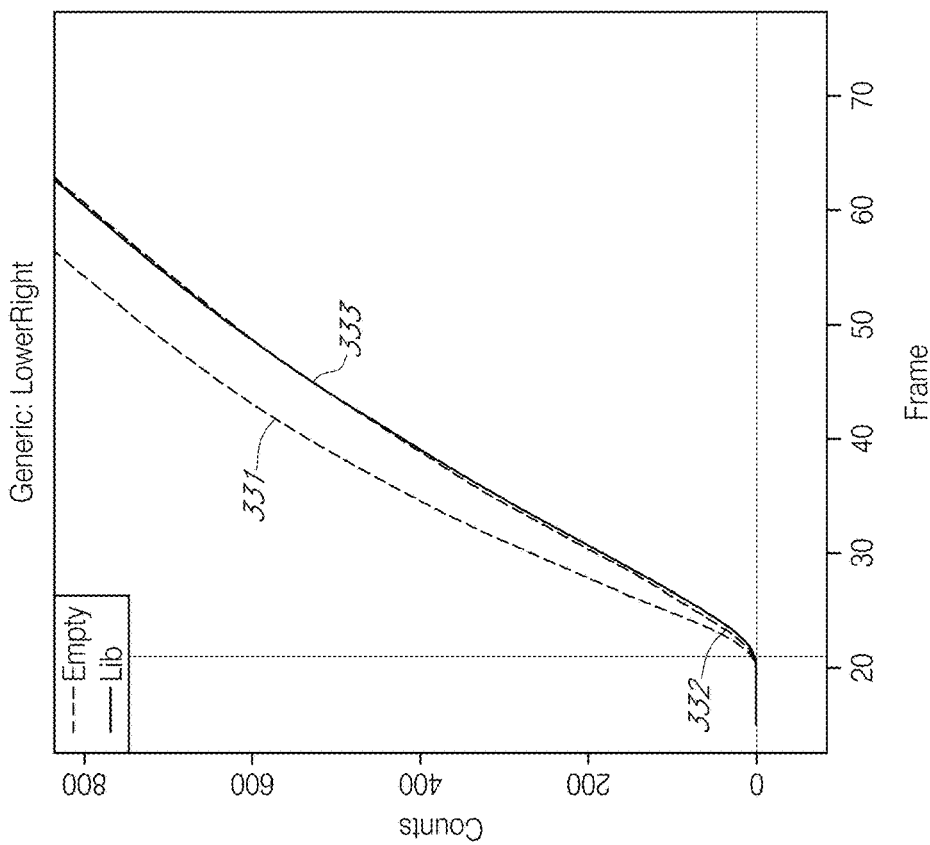
FIGS. 8A-8D demonstrate how a quadratic time warping may remove systematic differences between loaded and empty wells, and show an incorporation signal obtained using a time-warped background.
Figure 8A:
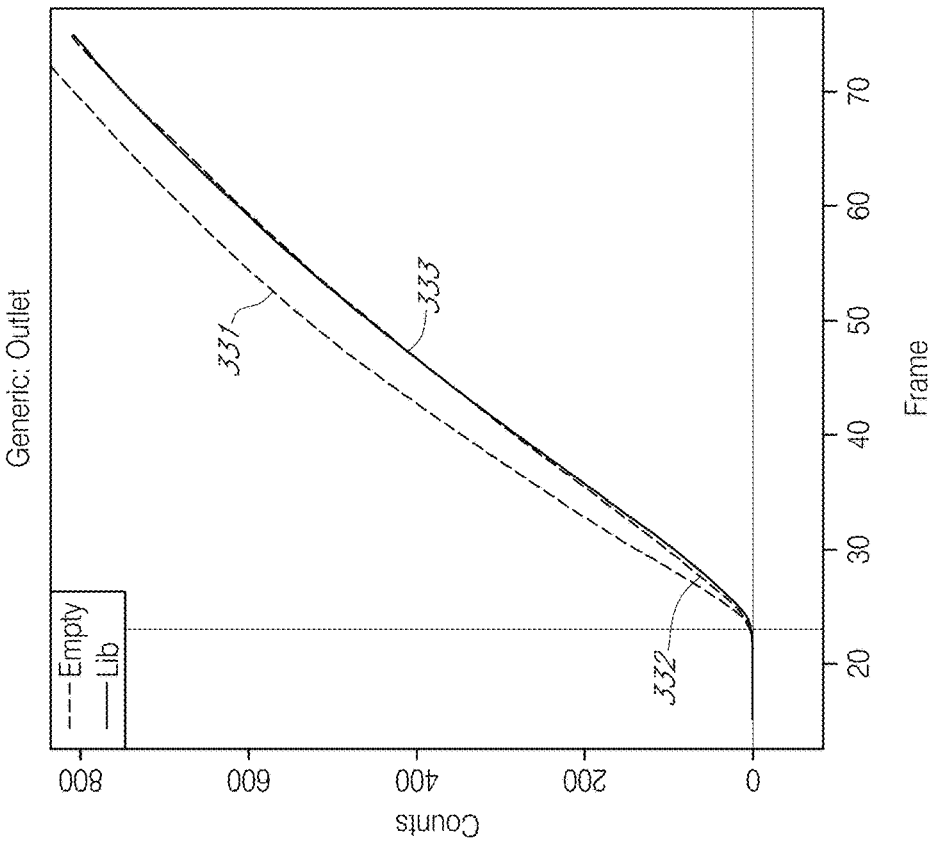
Figure 8D:
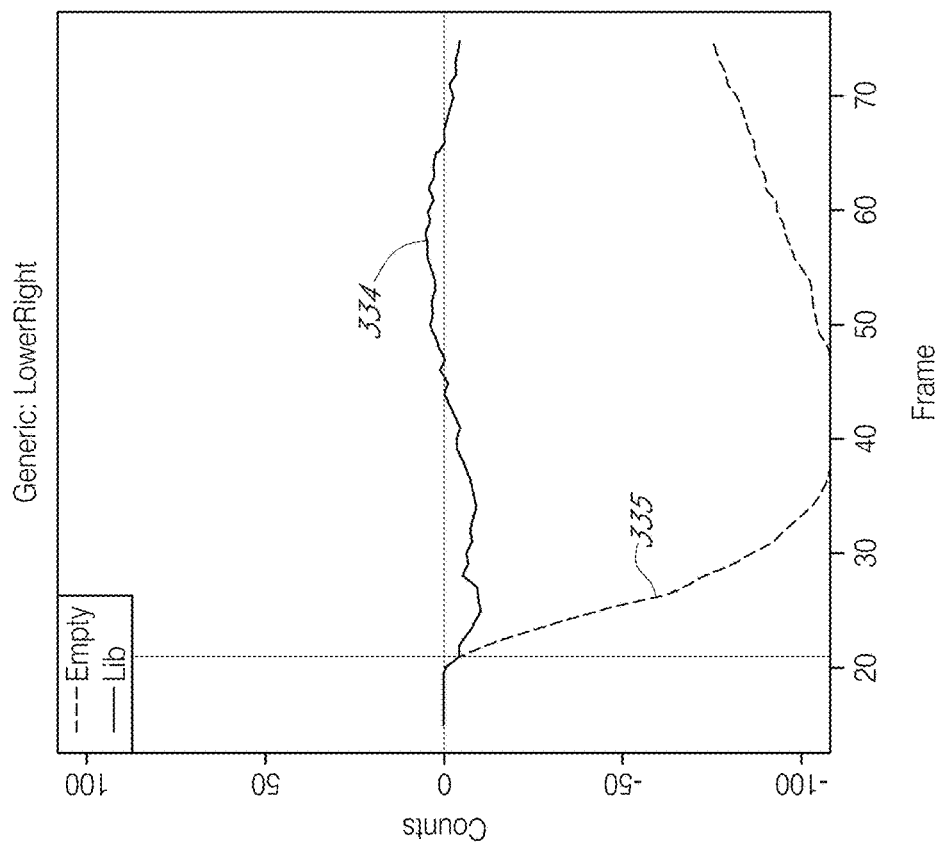
Figure 8C:
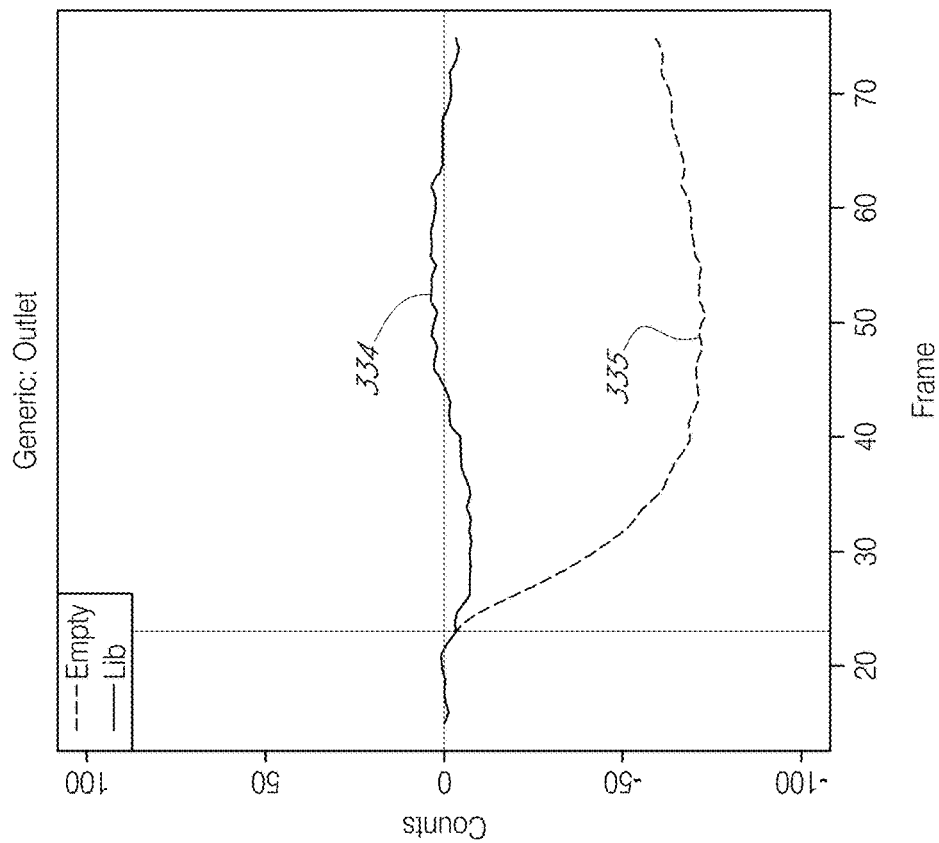

FIGS. 8A-8D demonstrate how this quadratic time warping may remove systematic differences between the empty and loaded wells. FIGS. 8A and 8C show data from wells near the outlet of the flow chamber, and FIGS. 8B and 8D show data from wells in the lower right corner of the flow chamber. In FIGS. 8A and 8B, line 331 is the plot of the signal response in an empty well and line 333 is the plot of the signal from a loaded well subjected to a 0-mer flow. Line 332 is the time-warped signal response of the empty well. In FIGS. 8C and 8D, line 335 is the plot of loaded well signal response curve 333 subtracted by line 331 (raw empty well signal curve). Line 334 is the plot of loaded well signal response curve 333 subtracted by line 332 (time-warped empty well signal curve). As seen here, simply subtracting the raw empty well background results in meaningless negative signal counts, whereas subtracting the time-warped background results in a substantially zero signal count, accurately reflecting the 0-mer event in the well.

Figure 9B:
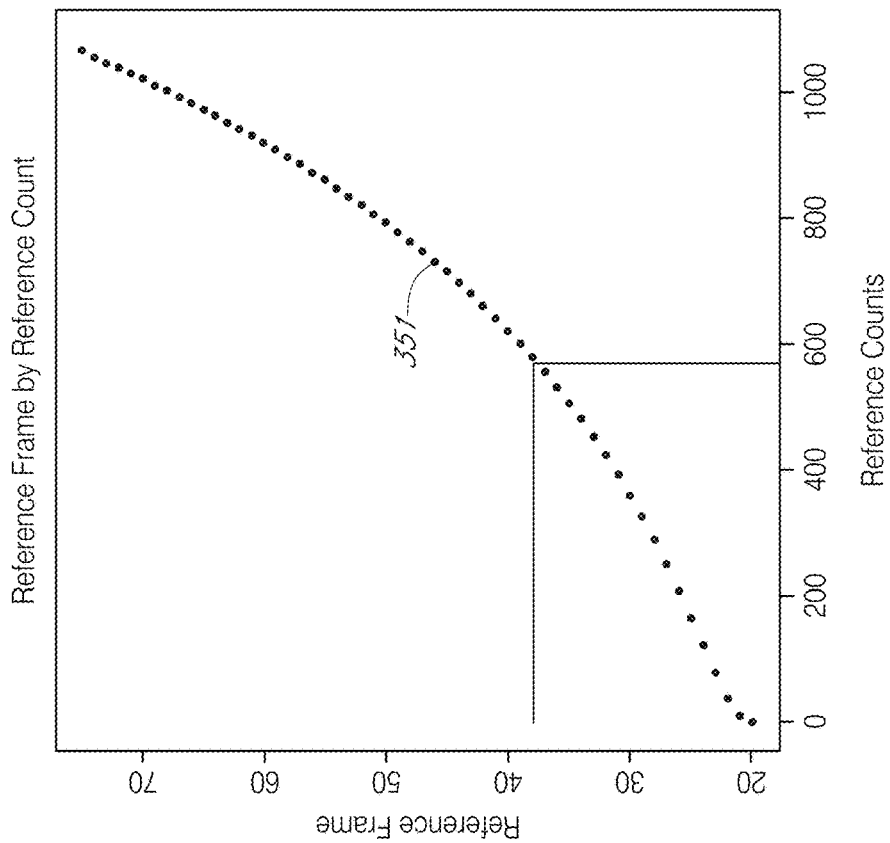
FIGS. 9A-9D demonstrate another example of how a quadratic time warping may be applied to an empty well signal curve.
Figure 9A:
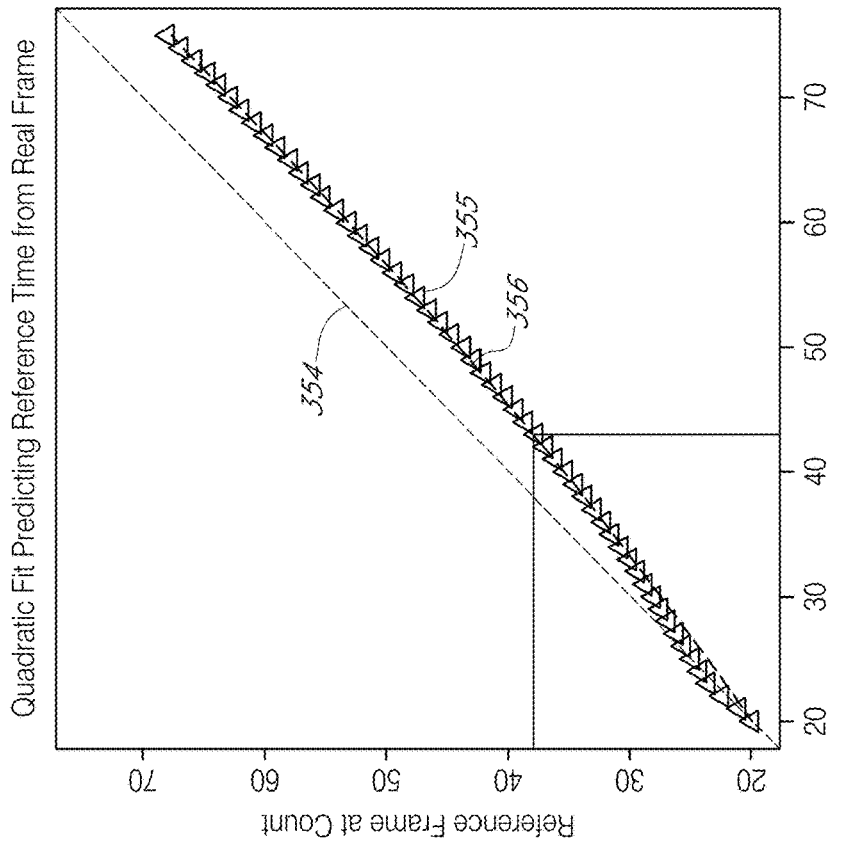
Figure 9D:
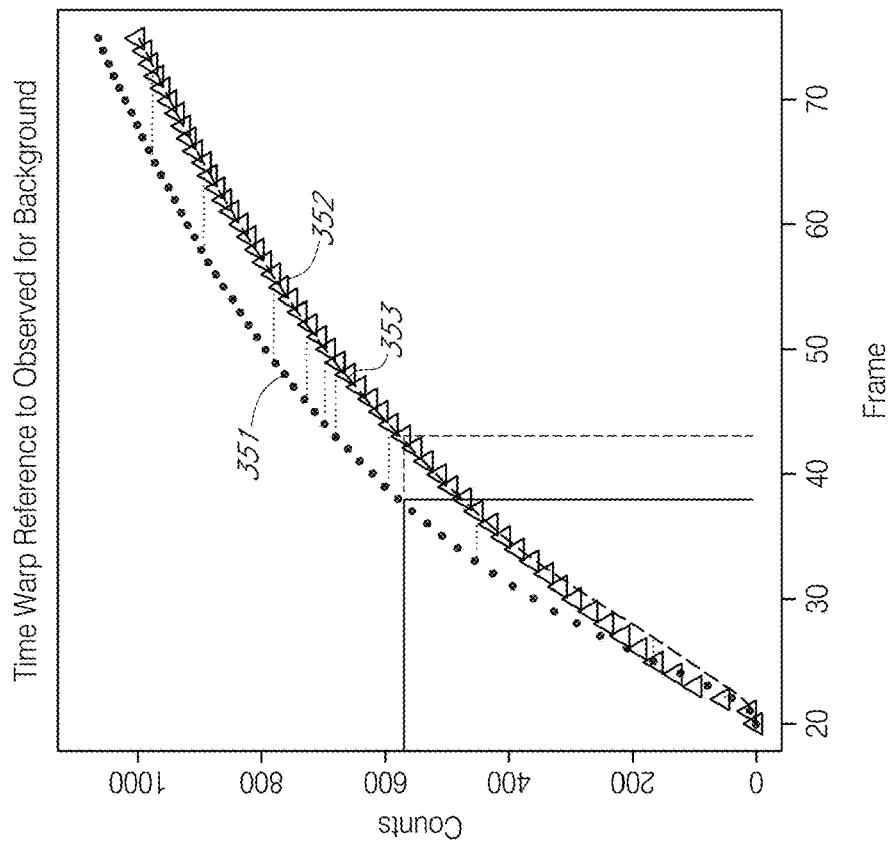
Figure 9C:
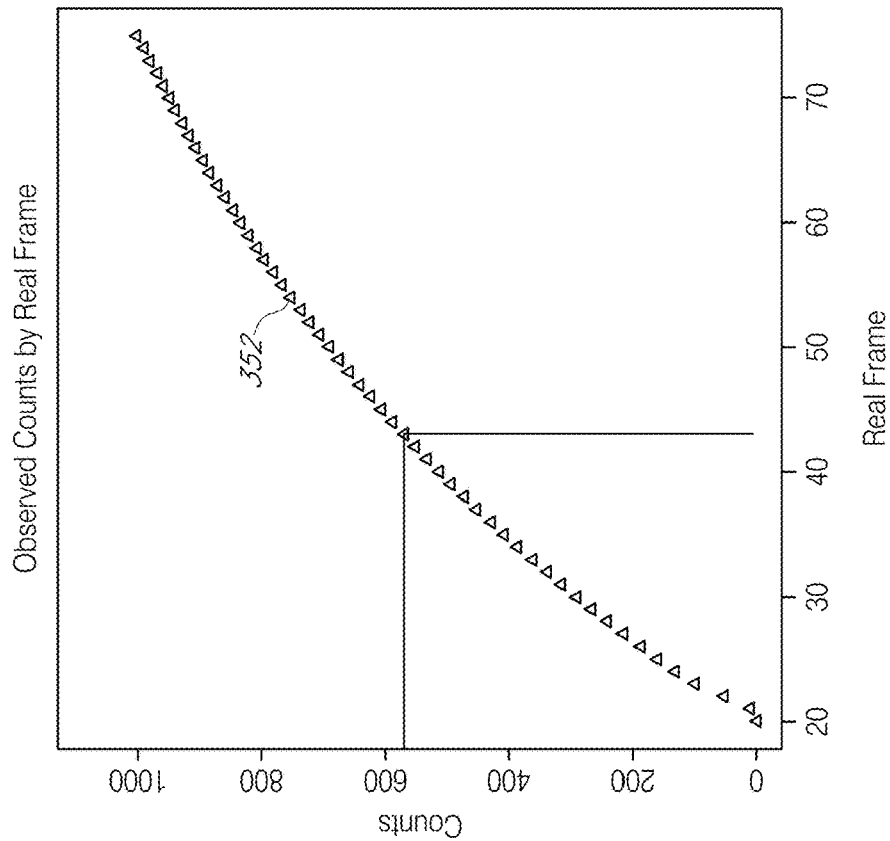

FIGS. 9A-9D demonstrate a similar situation as in FIGS. 7A-7D, except that the loaded well is subjected to a 1-mer flow instead of a 0-mer flow. FIG. 9B plots a signal response curve 351 of an empty well. FIG. 9D plots the signal response curve 351 of the empty well and the signal response curve 352 (triangles) of a loaded well subjected to a 1-mer flow. FIG. 9A plots where each point matches reference frames and real frames along line 355 (triangles; line 354 is a straight line that represents a linear plot for reference purposes). Line 356 is a quadratic polynomial that approximates this relationship (line 355). Thus, as shown in FIG. 9D, this quadratic polynomial may be used as the transformation function $f(t)$ to time warp the empty well signal response curve 351 so that it aligns with the loaded well signal response curve 352. The time-warped signal response curve for the empty well is shown by line 353.

Figure 10A:
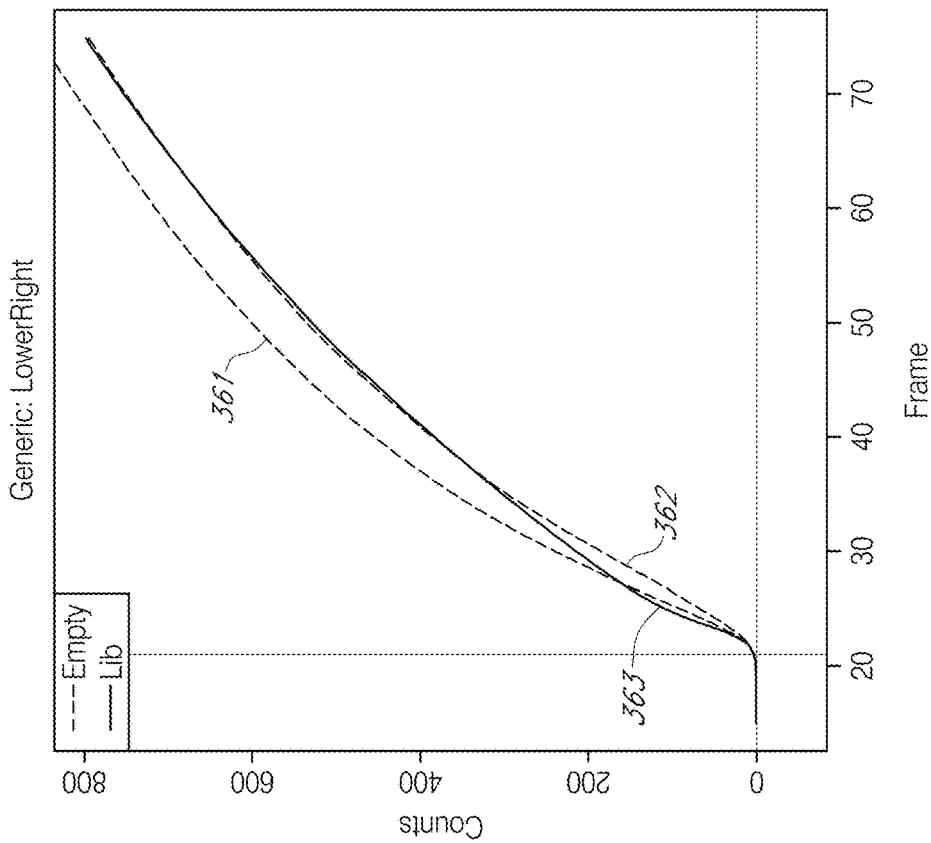
FIGS. 10A-10D demonstrate another example of how a quadratic time warping may remove systematic differences between loaded and empty wells, and show an incorporation signal obtained using a time-warped background.
Figure 10B:
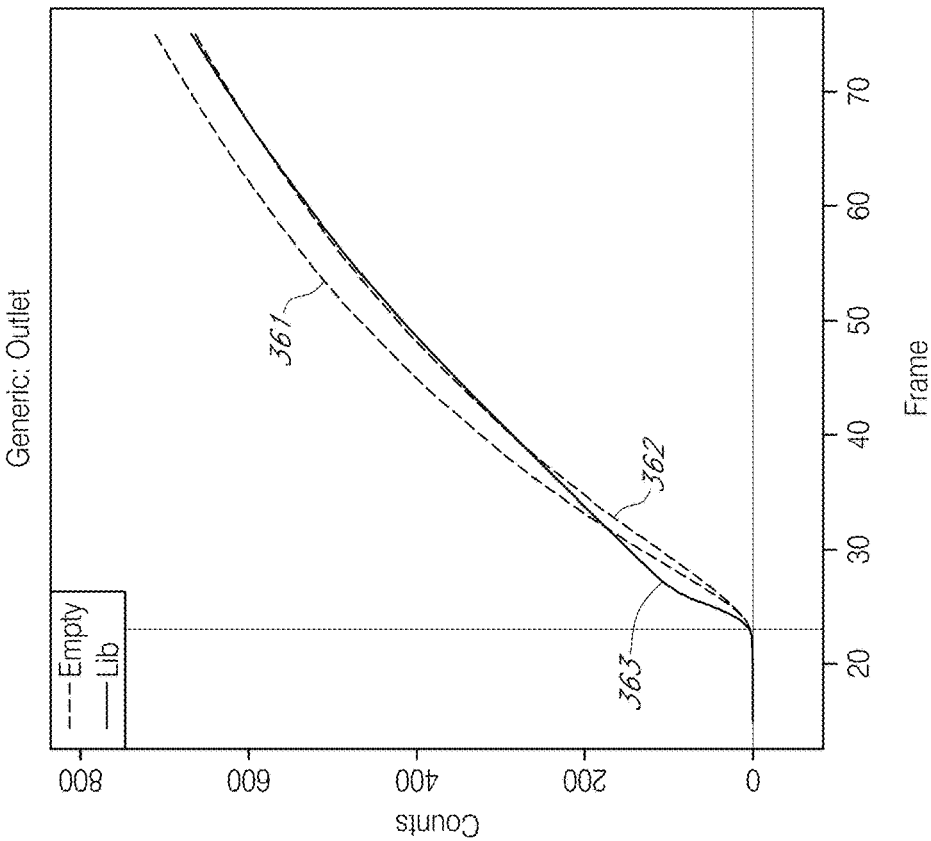
Figure 10C:
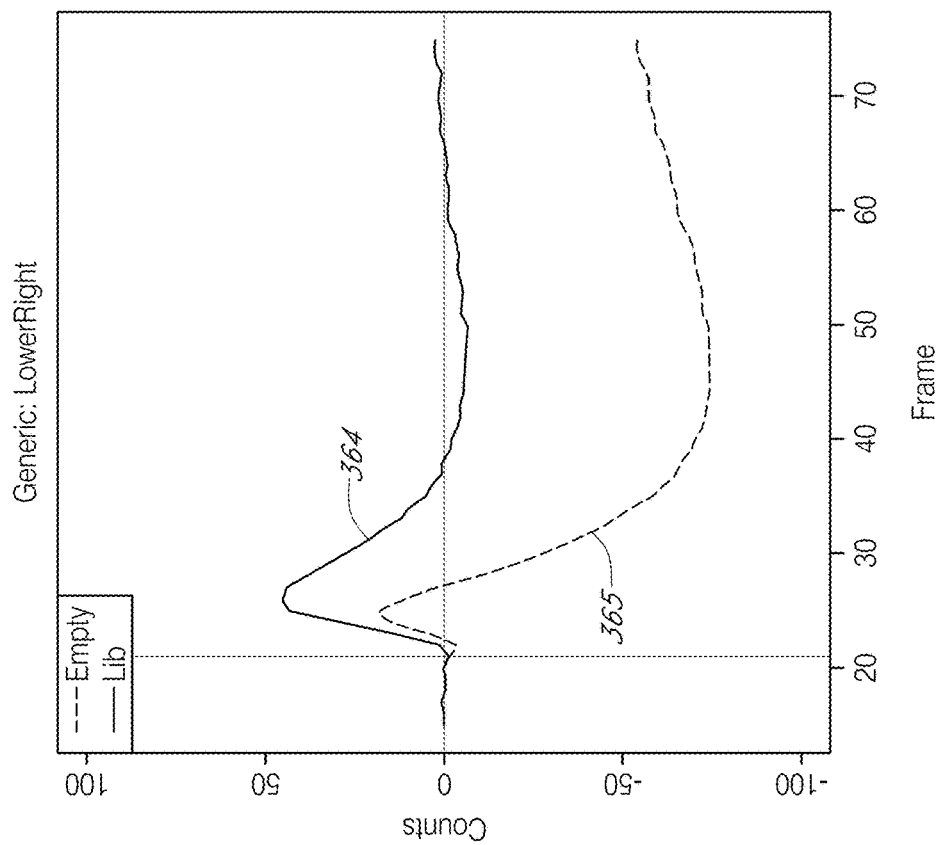
Figure 10D:
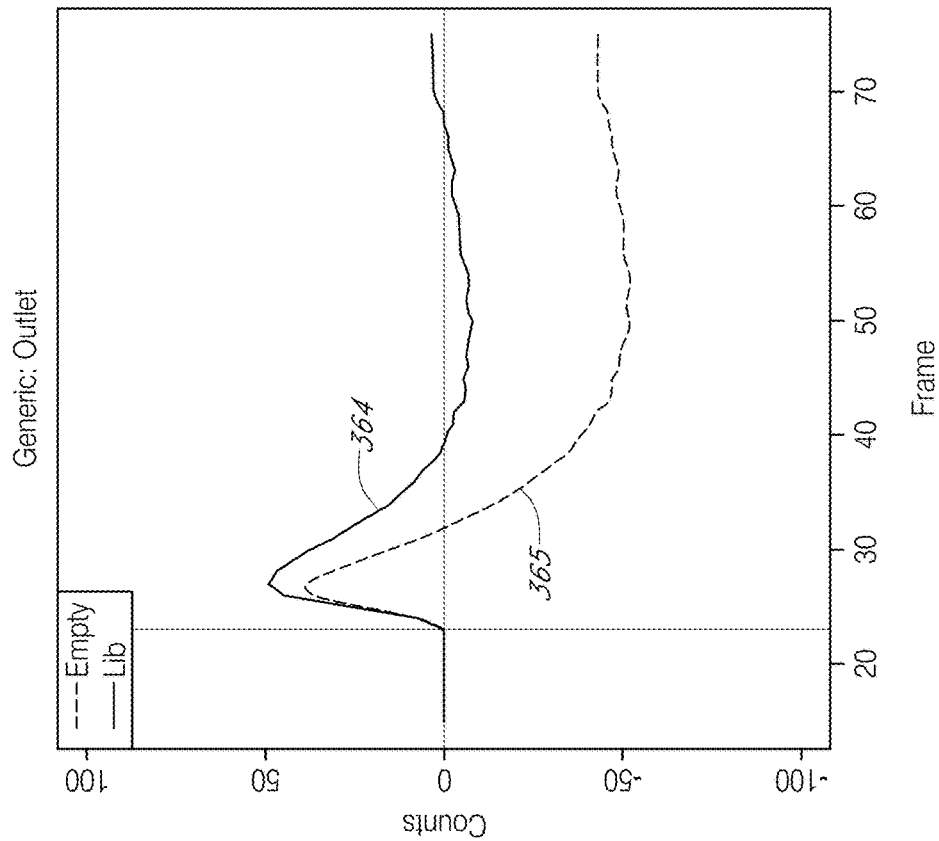
Figure 11A:
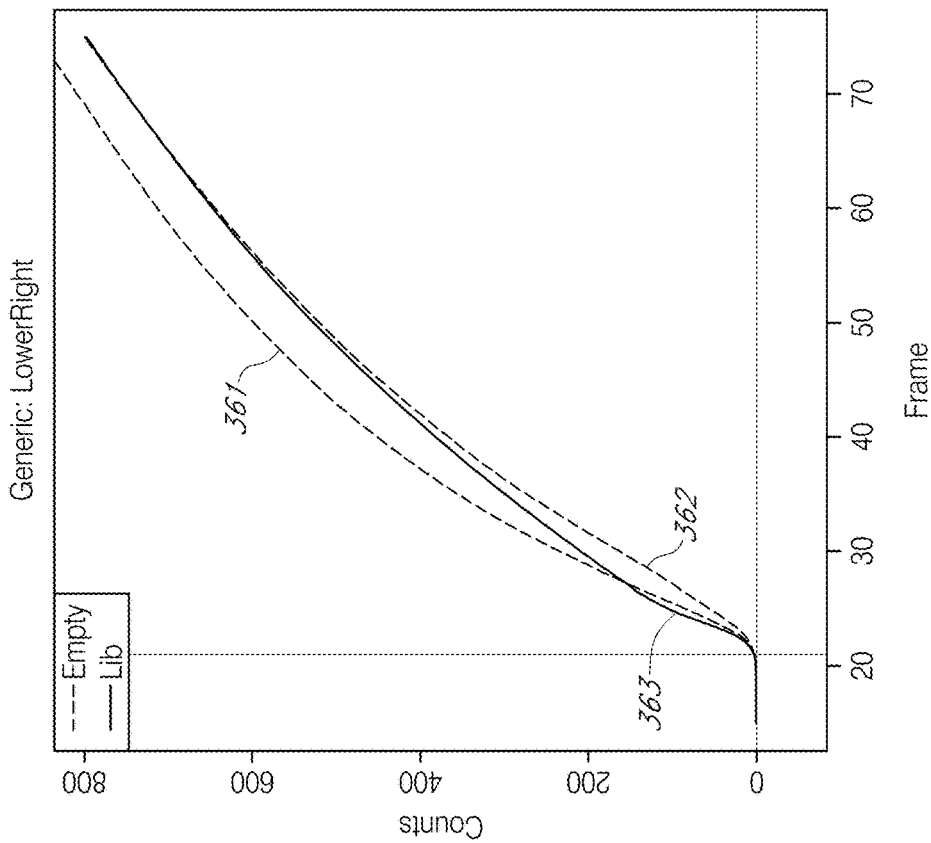
FIGS. 11A-11D demonstrate another example of how a quadratic time warping may remove systematic differences between loaded and empty wells, and show an incorporation signal obtained using a time-warped background.
Figure 11B:
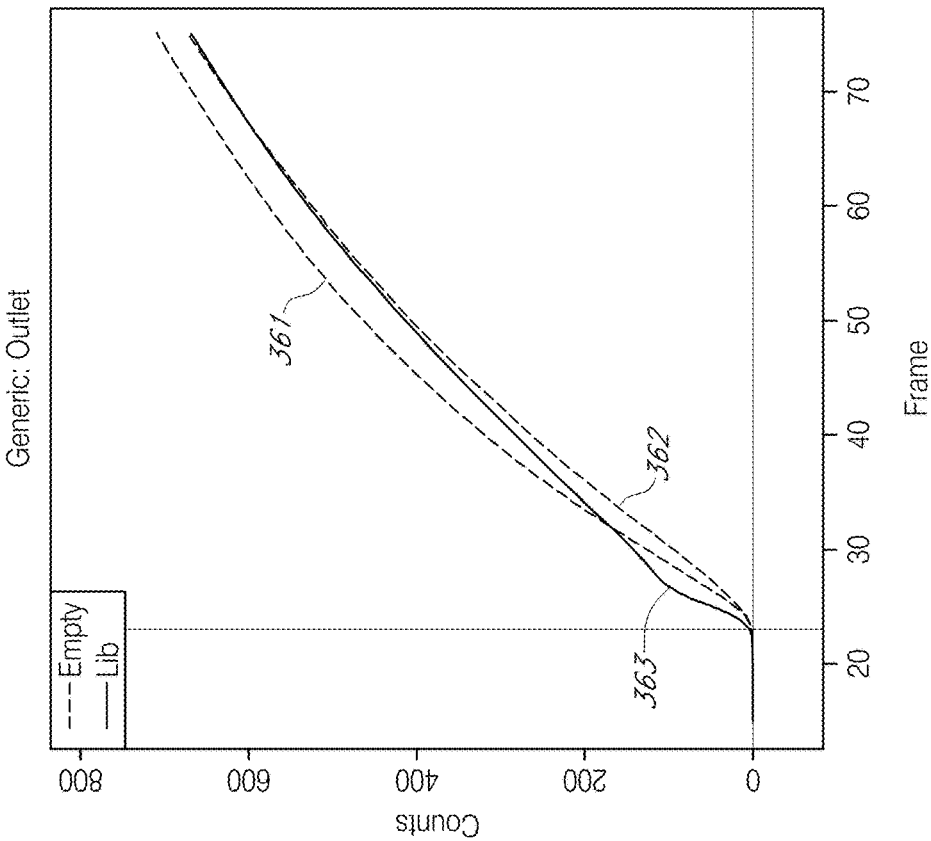
Figure 11D:
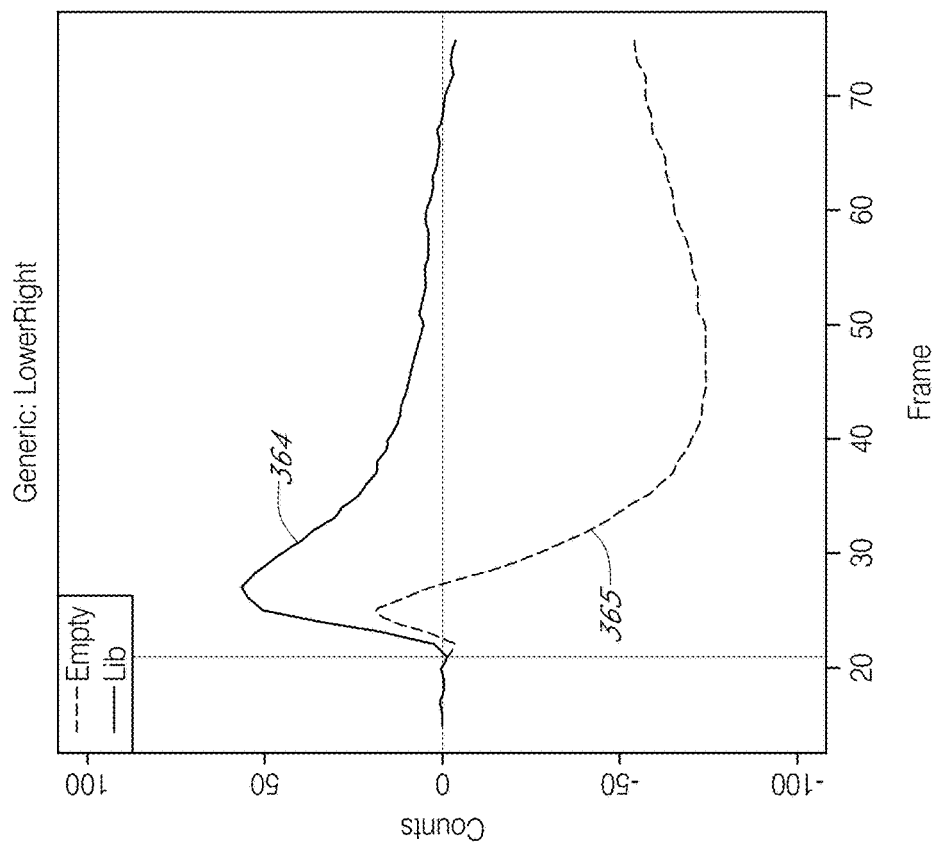
Figure 11C:
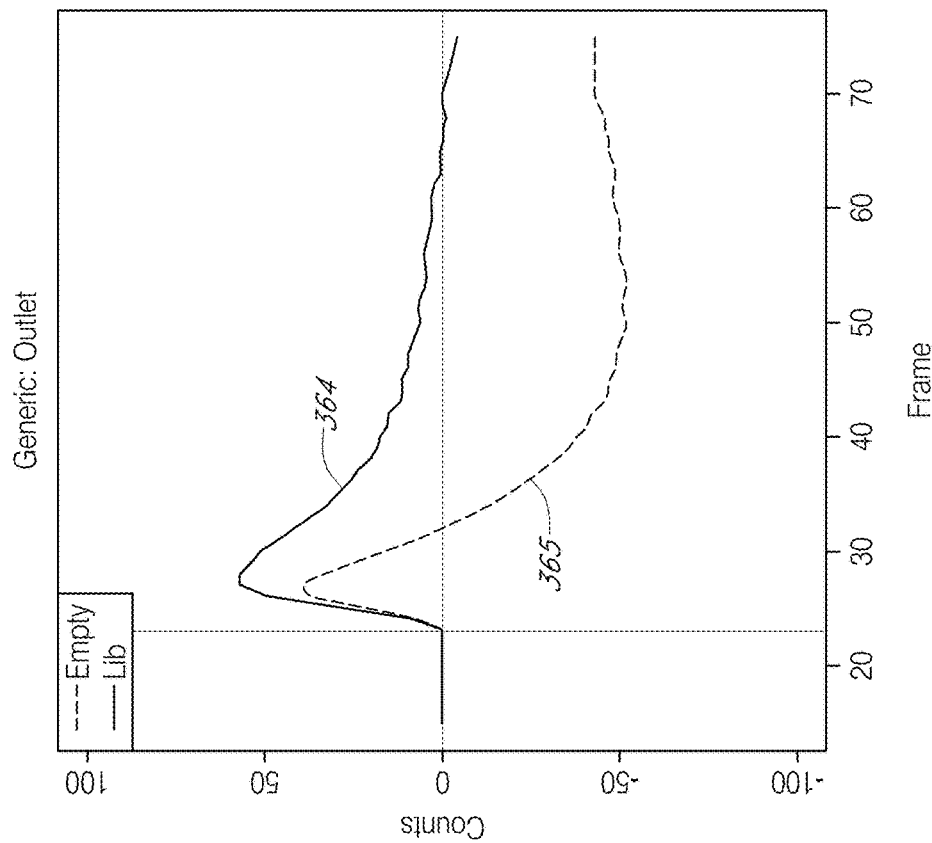
Figure 12A:
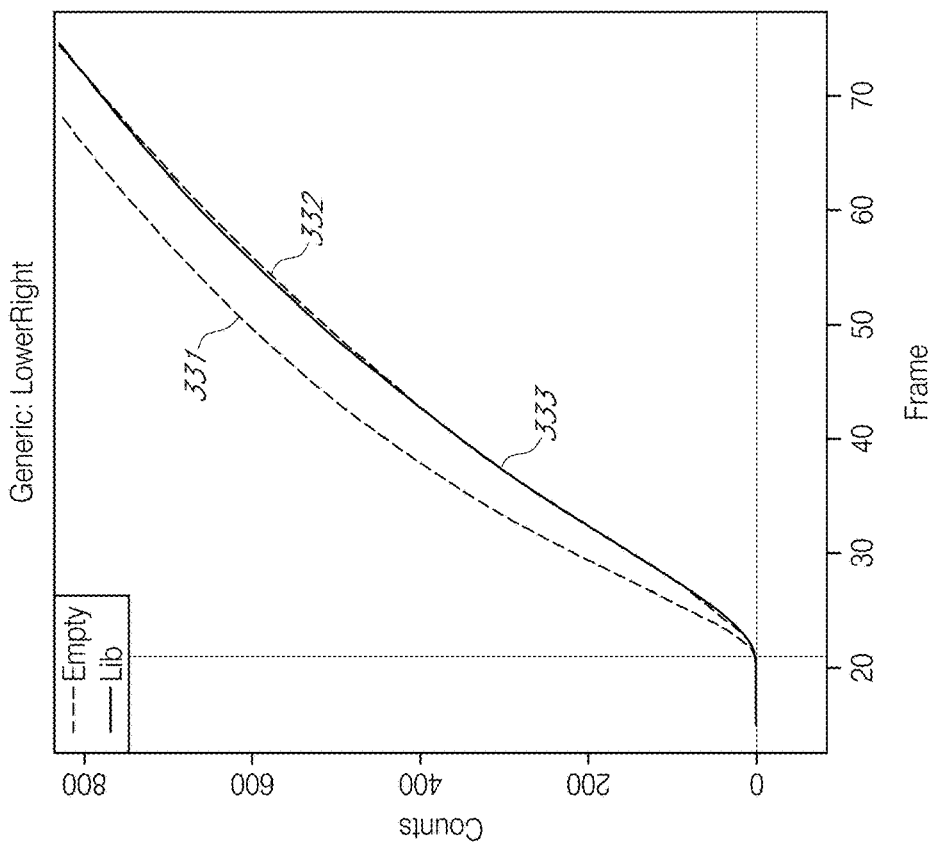
FIGS. 12A-12D demonstrate another example of how a quadratic time warping may remove systematic differences between loaded and empty wells, and show an incorporation signal obtained using a time-warped background.
Figure 12B:
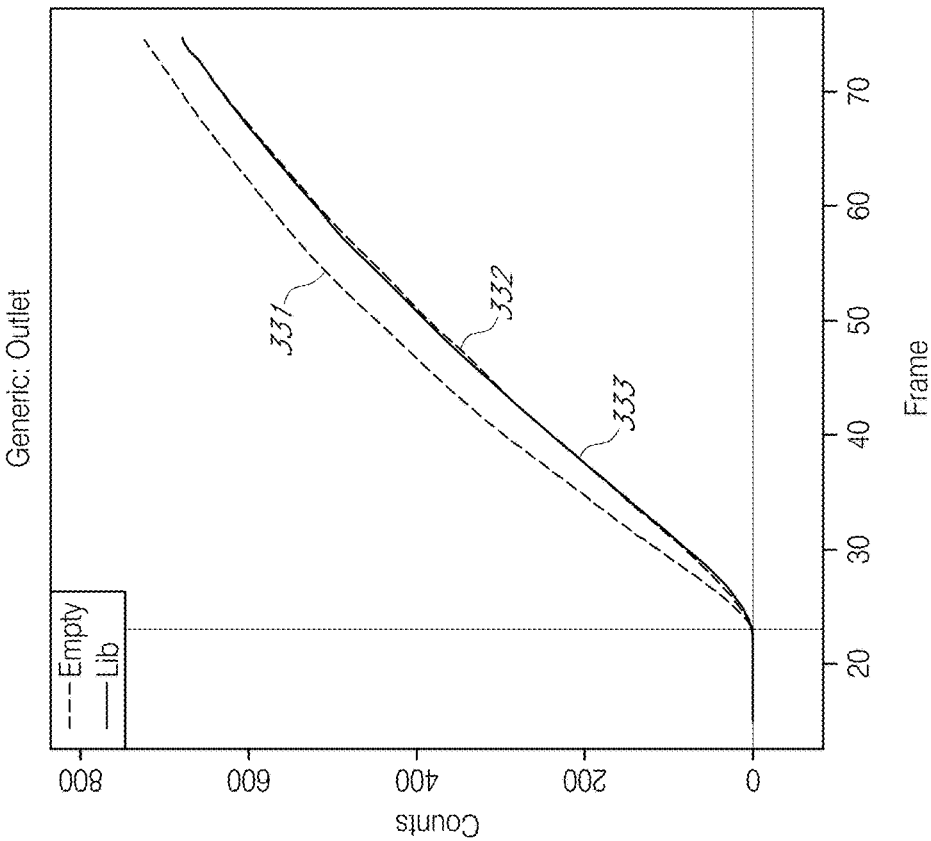
Figure 12D:
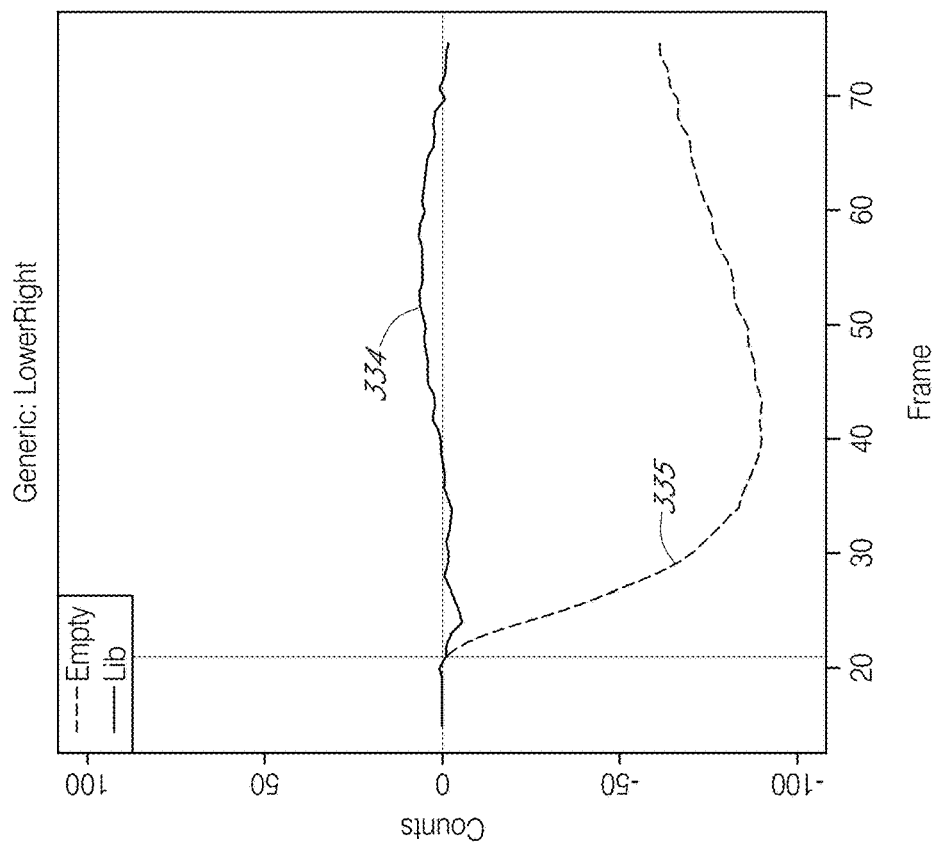
Figure 12C:
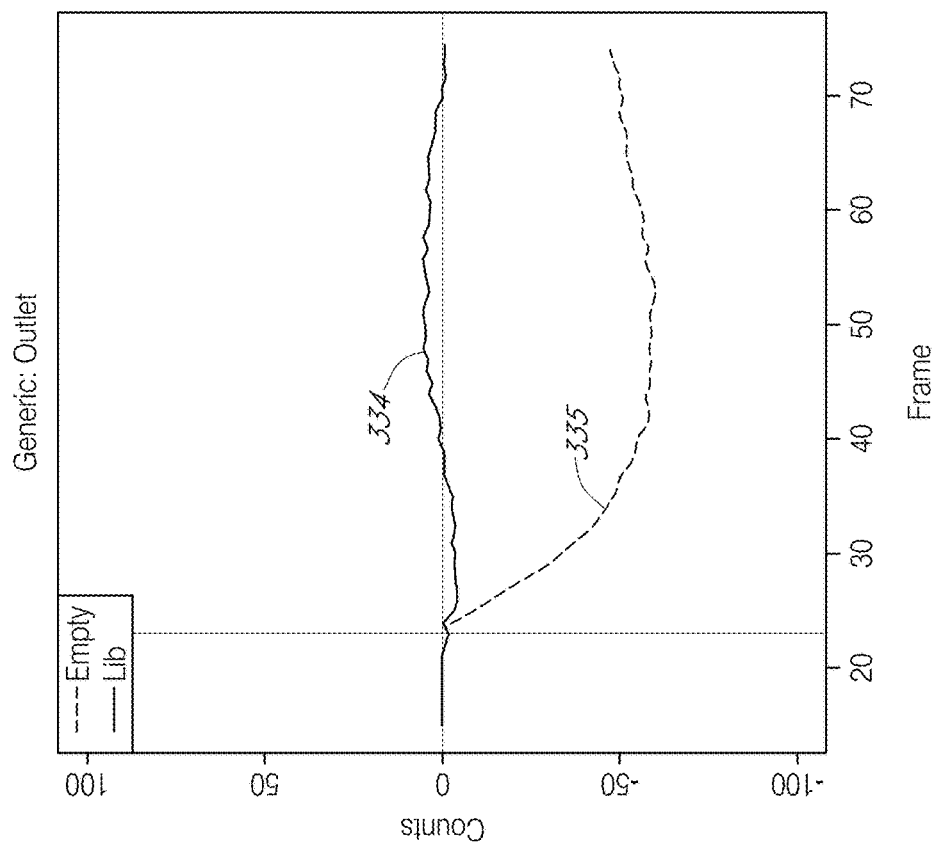
Figure 13A:
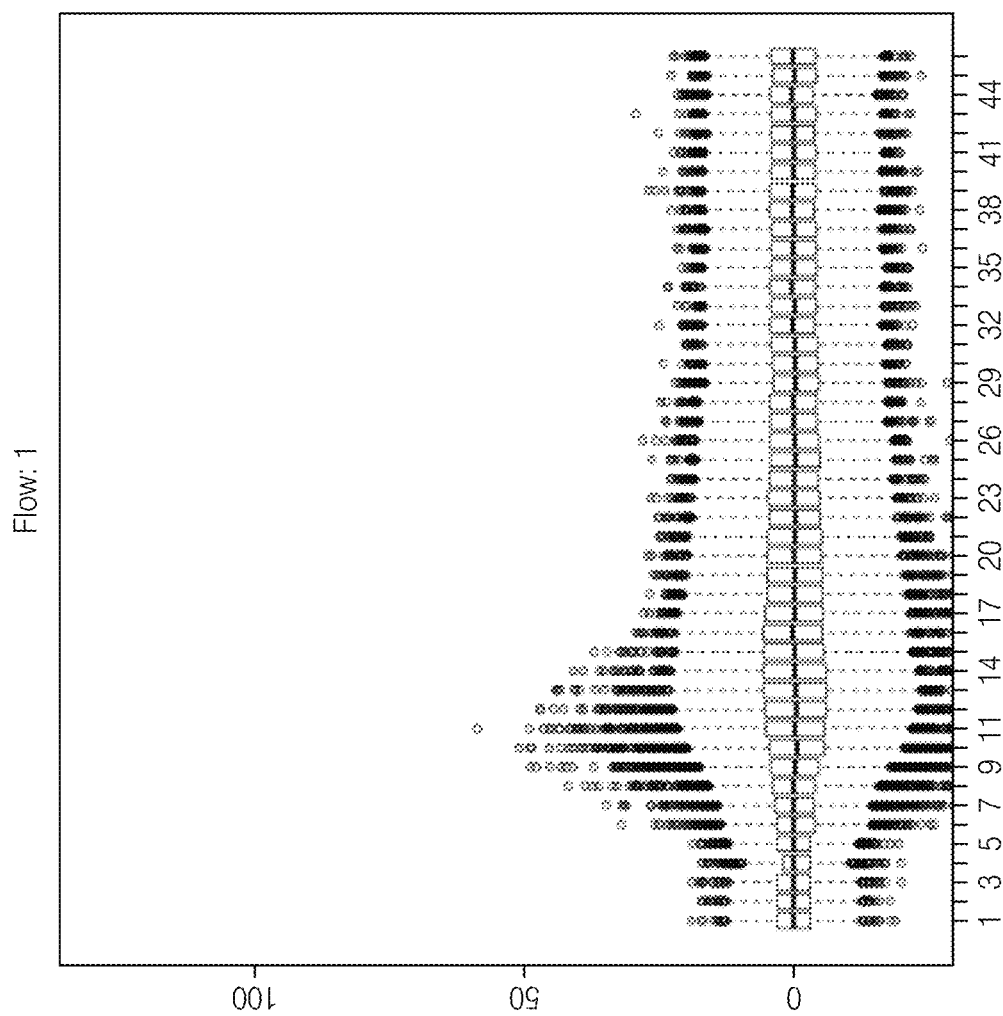
FIG. 13A-13D show best-fit residuals (after subtraction of a time-warped background) in the first four flows for empty wells.
Figure 13B:
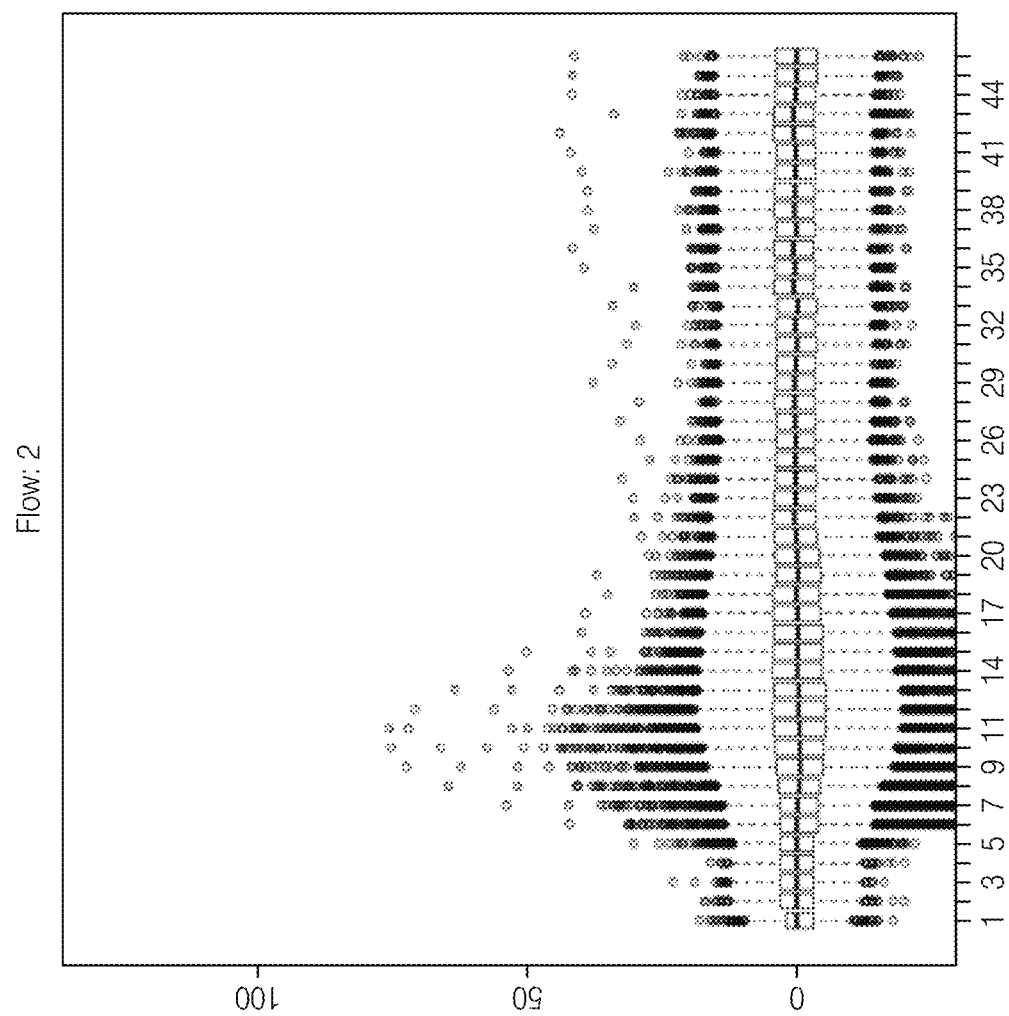
Figure 13C:
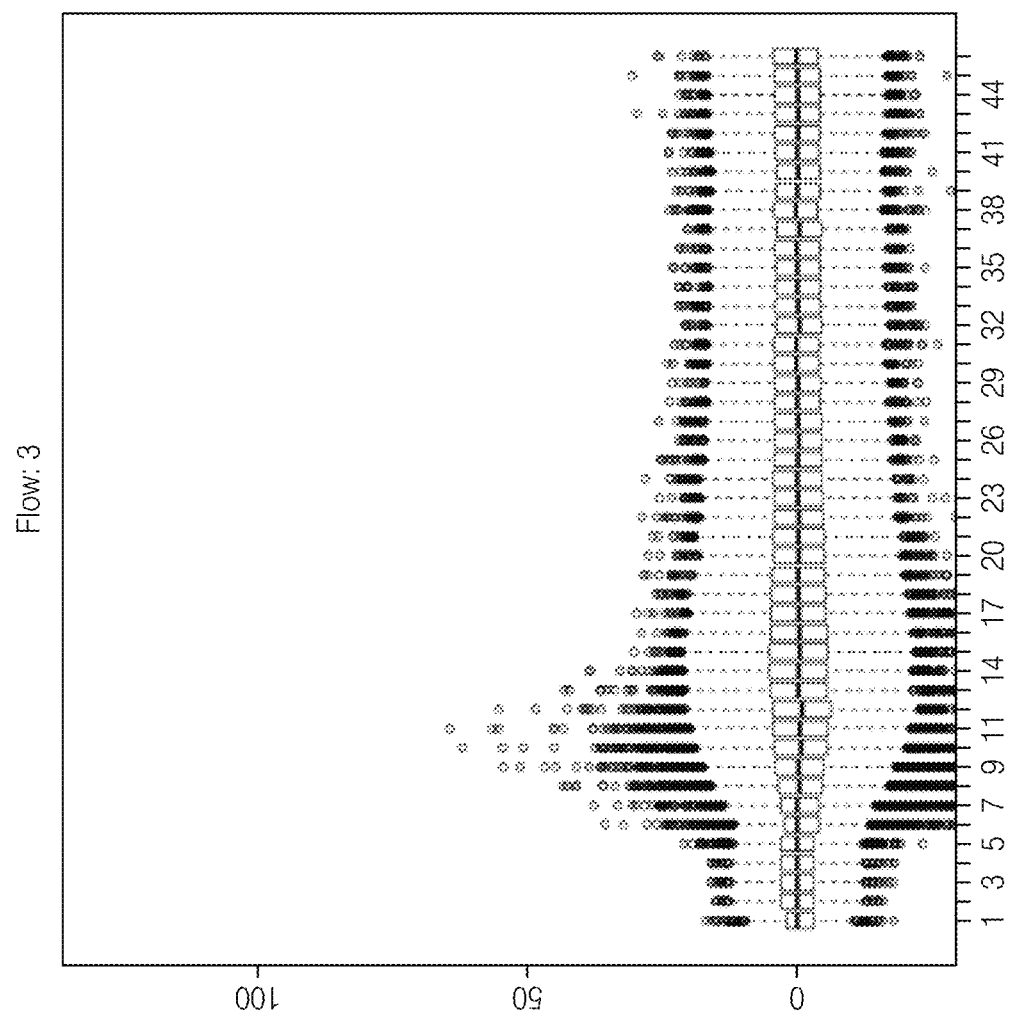
Figure 13D:
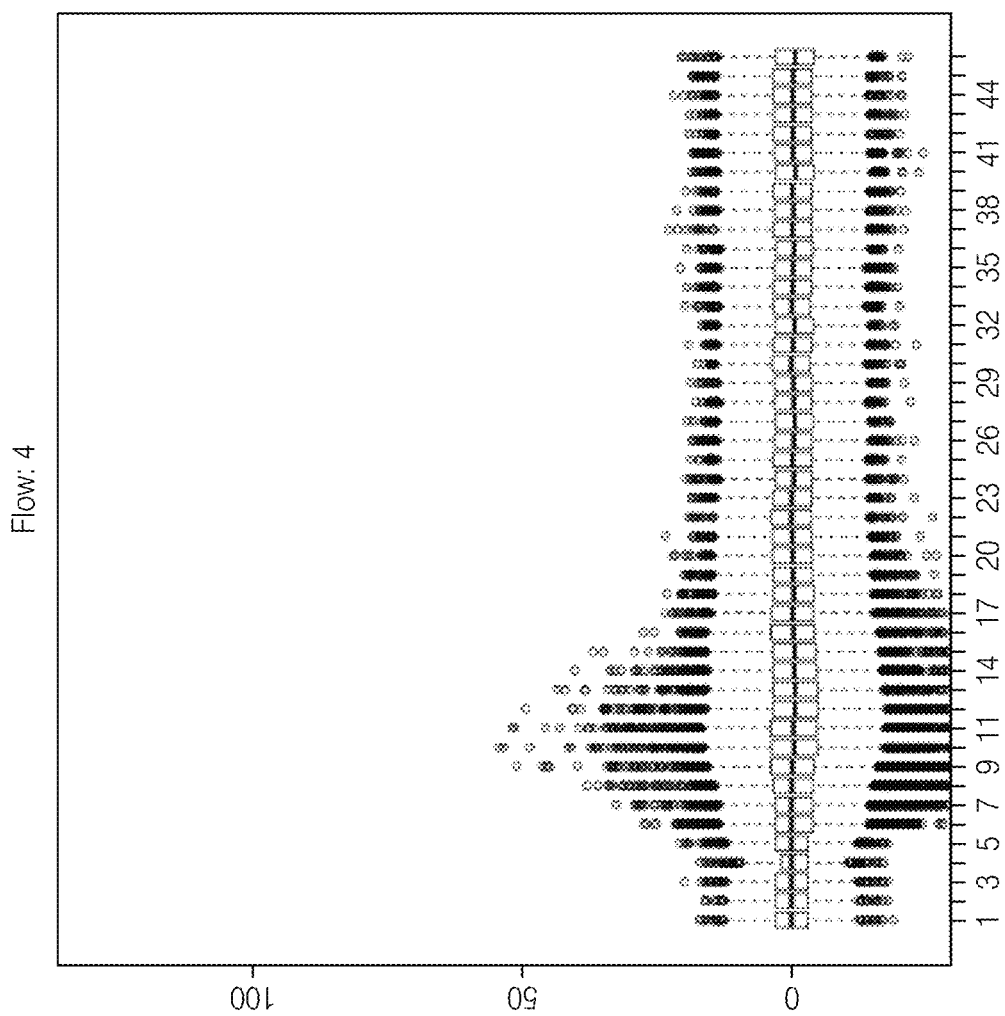
Figure 14A:
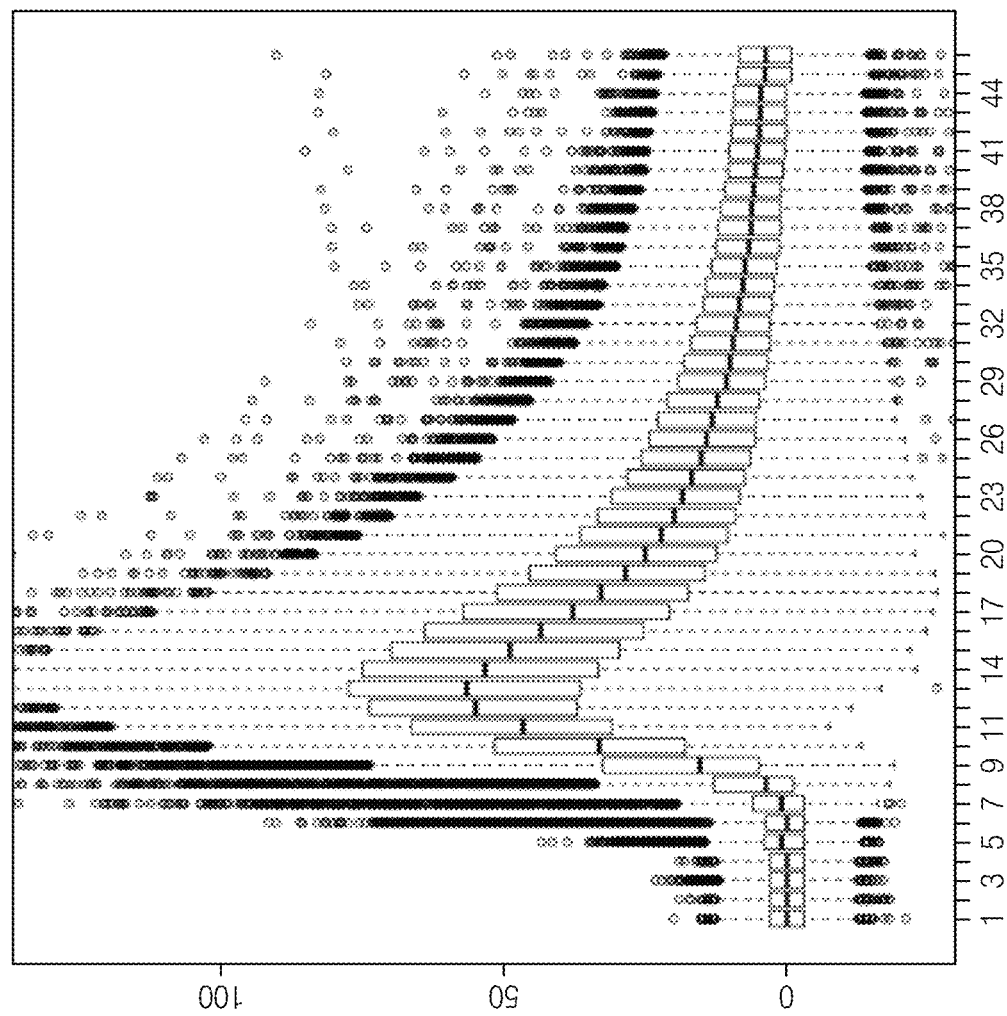
FIGS. 14A-14D show best-fit residuals (after subtraction of a time-warped background) from wells containing beads that have library sequences.
Figure 14B:
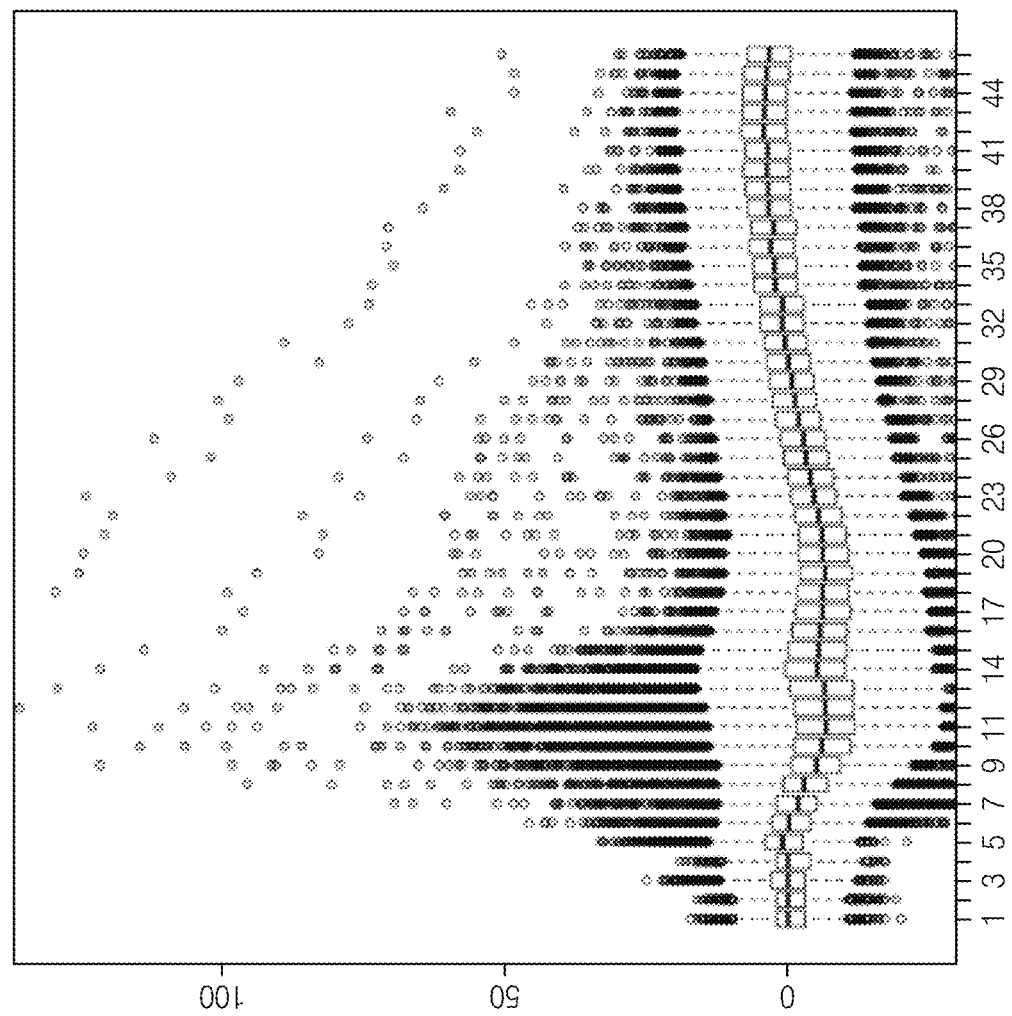
Figure 14C:
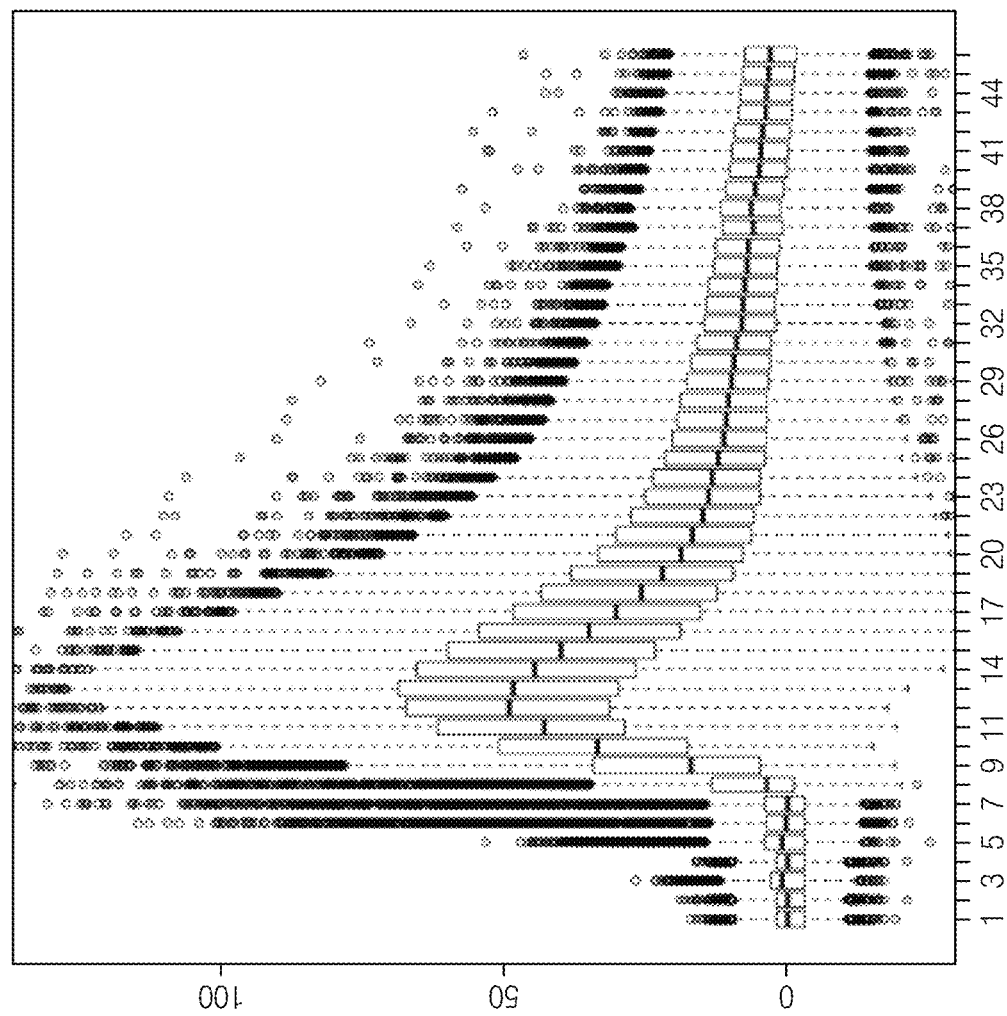
Figure 14D:
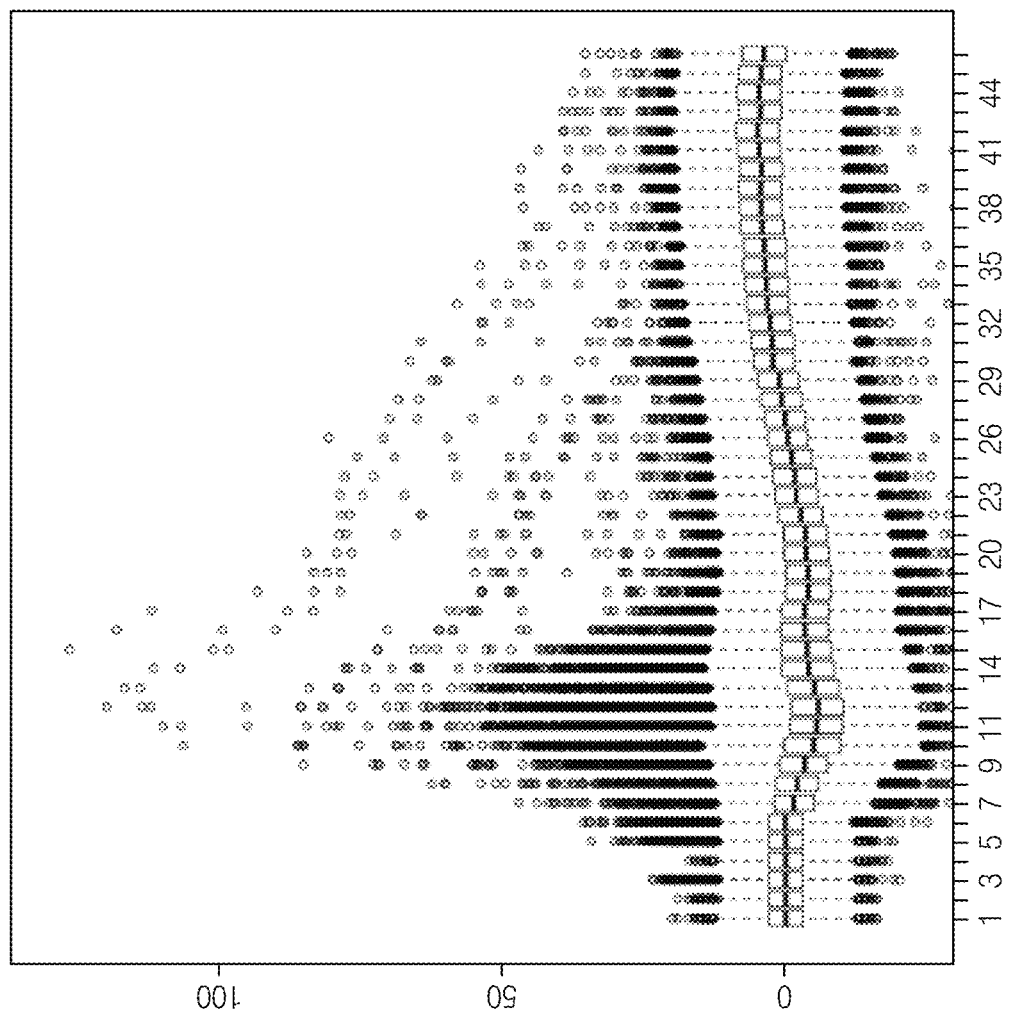

FIGS. 10A-10D demonstrate the results of background subtraction. FIGS. 10A and 10C show data from wells near the outlet of the flow chamber, and FIGS. 10B and 10D show data from wells in the lower right corner of the flow chamber. In FIGS. 10A and 10B, line 361 is the plot of the signal response in an empty well and line 363 is the plot of the signal from a loaded well subjected to a 1-mer flow. Line 362 is the time-warped signal response of the empty well. In FIGS. 10C and 10D, line 365 is the plot of loaded well signal response curve 363 subtracted by line 361 (raw empty well signal curve). Line 364 is the plot of loaded well signal response curve 363 subtracted by line 362 (time-warped empty well signal curve). As seen here, subtracting the time-warped background instead of the raw background results in a clearer picture of the incorporation signal.

FIGS. 10A-10D also demonstrate how a second-degree or third-degree polynomial may be particularly suitable for time warping. As seen in FIG. 10A, there is a small bump in the 1-mer signal curve 363 of the loaded well. This small bump represents the 1-mer incorporation signal. Warping of empty well signal curve 361 to fully fit the 1-mer signal curve 363 may be undesirable because the fitting would leave the incorporation signal undetectable. Thus, in some cases, using simpler polynomials (e.g. second or third degree) for the time warp may provide more useful results.

FIGS. 11A-11D show a series of plots similar to those in FIGS. 10A-10D, except that the time warping function derived from a 0-mer flow was used to time warp line 361 (from an empty well) to result in line 362. These results suggest that the fitted parameters from one flow may be used in another flow if the signal lag responses are similar, even though the signal amplitudes and nucleotide compositions may be different from flow to flow. FIGS. 12A-12D show a series of plots similar to those in FIGS. 8A-8D, except that the time warping function derived from a different 0-mer flow was used to time warp line 331 (from an empty well) to result in line 332.

FIGS. 13A-13D show the best-fit residuals (after subtraction of the time-warped background) in the first four flows for empty wells, compared one at a time to a generic empty well signal response in the middle region of the reactor array, after subtracting the generic background in each frame. Because empty wells are modeled by themselves, the signal noise is relatively low and only rarely shows deviations (which may actually be loaded wells that are misidentified as being empty).

FIGS. 14A-14D shows the best-fit residuals (after subtraction of the time-warped background) from wells containing beads that have library sequences. The plots are shown flow-by-flow aggregated across all beads by the distribution per flow. A strong, systematic signal appears in the flows over the key sequence and a tight distribution in the 0-mer flows. The time-warped background was constructed using the same parameters across all flows, determined from the average of the 0-mer flow parameters. The results would be similar if any particular O-mer flow was used to construct the time warp.

Figure 15:
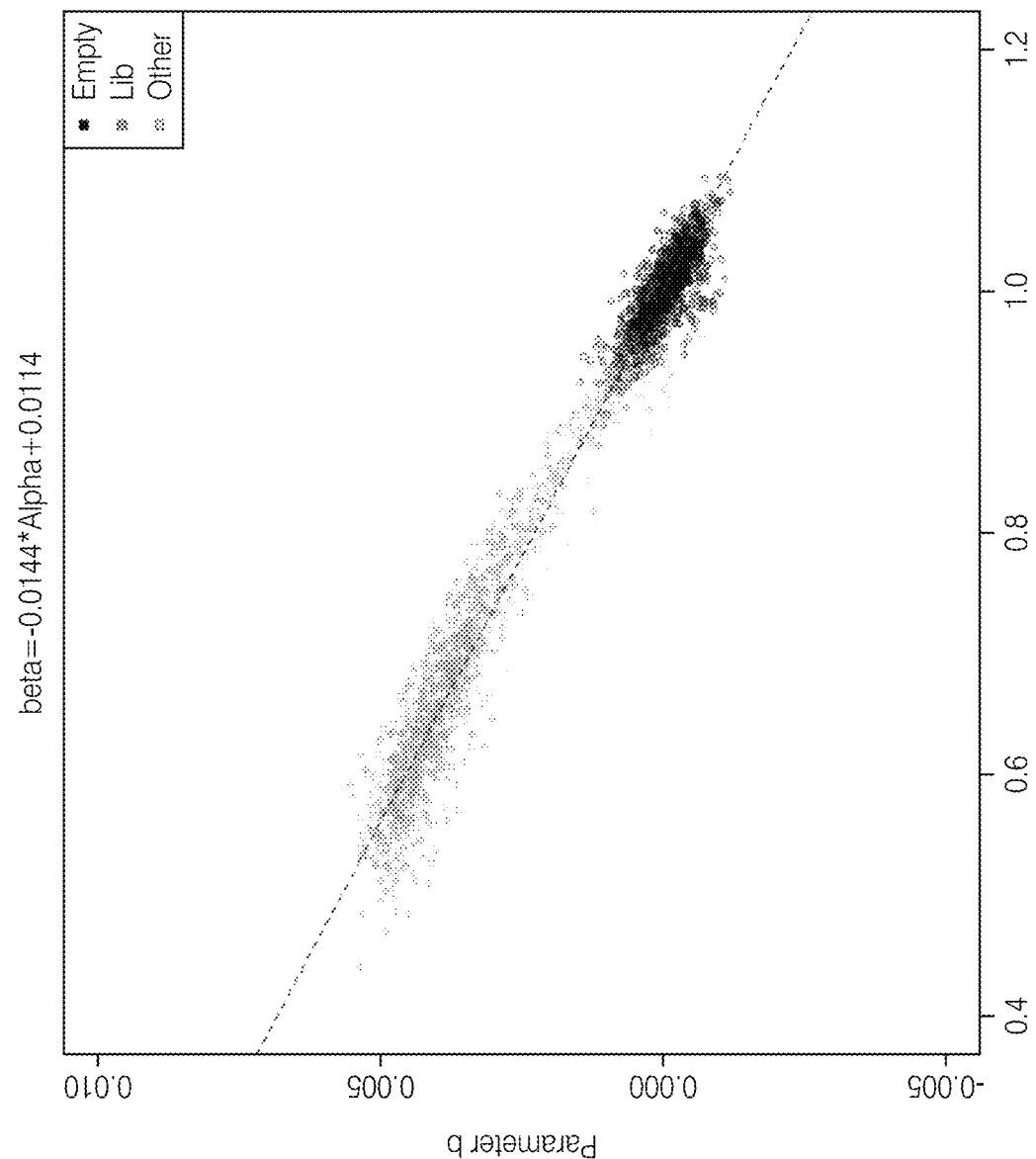
FIG. 15 shows two parameters a and b of a quadratic time warping function plotted against each other.

For a quadratic time warping function $g(t)=at+bt^2$, FIG. 15 shows the two parameters a and b plotted against each other. This demonstrates that the two parameters are highly correlated to each other. As such, the time warping function could be further simplified by using only a single parameter. Also, this plot demonstrates that the different populations of wells become stratified according to these time warp parameters, with loaded wells (with library sequence; light-shaded circles) systematically lagging empty wells (dark-shaded circles), both collectively and individually, and with all other wells (empty circles) distributed somewhere in the middle.

In an exemplary embodiment, direct optimization of an objective function is envisioned using $f(t)$ as the observed 0-mer flow for a loaded well of interest and z(t) as the observed empty well background. The optimization involves finding a solution to the quadratic time warp $g(t)=at+bt^2$ that minimizes $(f(t)-z(g(t)))^2$ over the time range of interest, subject to the constraint that g(t) is monotone increasing over the time range of interest (time only goes forwards).

For some current values of a and b, the result of a step da/db in the function g(t) can be linearly approximated by $f(t)-z(g(t))-da \times z'(g(t)) \times t-db-z'(g(t)) \times t^2)^2$. The problem can be represented as finding a least-squares solution to $FZ=ZP \times d$,
where FZ is the following N×1 matrix:

$$\begin{bmatrix} f(t_0)-z(g(t_0)) \\ \ldots \\ f(t_i)-z(g(t_i)) \\ \ldots \\ f(t_{max})-z(g(t_{max})) \end{bmatrix}$$

for all t in the time range; and ZP is the following N×2 matrix:

$$\begin{bmatrix} z'(g(t_0))t_0 & z'(g(t_0))t_0^2 \\ \ldots & \ldots \\ z'(g(t_i))t_i & z'(g(t_i))t_i^2 \\ \ldots & \ldots \\ z'(g'(t_{max}))t_{max} & z'(g'(t_{max}))t_{max}^2 \end{bmatrix}$$

for all t in the time range; and d is the following vector:

$$\begin{bmatrix} da \\ db \end{bmatrix}$$

The foregoing procedure can be iterative, allowing the parameters a and b to converge to the point where the functions are registered using the time warp parameters. The foregoing is not restricted to the time warp being represented by a quadratic, and can be applied to many different functional forms. The time warp function $g(t)=at+bt^2$ may be monotone over the desired time range (positive derivative). Therefore, in an embodiment, g(t) is optimized within $a>0$ and $b>-a/2t_{max}$.

The following time ranges may be ill-conditioned, where ZP is the following:

$$\begin{bmatrix} z_0(g(t_0))t_0 & z_0(g(t_0))t_0^2 \\ \ldots & \ldots \\ z'(g(t_i))t_i & z'(g(t_i))t_i^2 \\ \ldots & \ldots \\ z'(g(t_{max}))t_{max} & z'(g(t_{max}))t_{max}^2 \end{bmatrix}$$

Therefore, in an exemplary embodiment, the function z(t) may be smooth and differentiable (which can be modeled as splines with few knots). Also, applying a Tikhonov regularization (ridge regression) to the linear model can improve the condition number. That is, $(ZP^T \times ZP + \lambda \times I)^{-1} \times (ZP^T \times ZP \times FZ)$ yields an effective solution even when the data is relatively unstable.

In some cases, the loaded well signal curve may actually lead the empty well signal curve (instead of lagging). This may lead to a situation where the counts can exceed the range of the reference signal. This may be handled by truncating the data for fitting and using only frames within the common range of counts. Residuals may be arbitrarily set to zero after this point. This may indicate something pathological has happened, such as loaded wells that are misidentified as empty wells or unusual local hydrodynamics intersecting the patch of wells.

As will be explained below, a small misalignment of time can be made linear by using t+dt as the direction for adjusting the time warp function. In this case, where the constant term is zero, this adds a new small offset and affects the other terms similarly. This procedure adjusts an existing time warping to fit a new flow using a simple linear model. The residuals from a slight misfit of the time warp to the data should lie along the vectors of the matrix ZP, and therefore, adding those vectors into a modeling attempt should account for much of the variation due to the time warp parameters not exactly fitting a new flow. This can be done using Bayesian techniques or any other suitable technique.

Having established the 0-mer fitted, time-warped empty well function (e.g. by fixing one or more parameters of the function), the fitted time-warped empty well function can be applied to signal data from other flows in the well, including those that result in incorporation events. For example, the parameter(s) of the fitted time-warped empty well function can be obtained from 0-mer flows in one or more of the earlier flows in the sequencing operation (e.g. flows over the known key sequence of the polynucleotide strand), and then with the function parameters established, the fitted time-warped empty well function can be applied to flows that occur later in the sequencing operation (e.g. for unknown portions of the polynucleotide sequence).

The fitted time-warped empty well function may be used in any suitable manner to obtain the incorporation signal. For example, the incorporation signal may be obtained by subtracting the signal curve generated by the fitted time-warped empty well function from the output signal of the flow of interest. In another example, the incorporation signal may be obtained by solving a model for the measured output signal from the well of a reactor array. The output signal may be modeled as a linear combination of one or more signal components.

For example, the output signal may be modeled as a linear combination of a function for the background signal component and a function for the incorporation signal component. The output signal model may also include other sources of errors or offsets (e.g. signal gain). The signal acquired from the reaction in the wells may be represented as $X(\omega, f, t)$ where $\omega$=well, $f$=flow, t=frame, allowing the signal to be decomposed into tractable approximations. For example, the output signal may be represented as $X(\omega, f, t)=I(\omega, f, t)+B(\omega, f, t)+e$, with $I(\omega, f, t)$ being the incorporation component, $B(\omega, f, t)$ being the background component, and e being an error term. In this instance, the 0-mer fitted time-warped empty well function may represent $B(\omega, f, t)$. As such, the output signal function can be expressed as follows: $X(\omega, f, t)=I(\omega, f, t)+Z_f(t|\Theta(\omega))+e$, with $Z_f(t|\Theta(\omega))$ representing the 0-mer fitted time-warped transformed empty well function, with $\Theta$ representing the parameter(s) of the time warping function.

In another example, the background signal z(t) may be modeled as two components: $z(t)=s(t)+C(t)$, where s(t) is a smooth function over time frames and represents the background signal resulting from changes in the bulk reagent fluid and CO is an individual frame noise term designed to capture systematic electronic deviations. The response s(t) in loaded wells lags empty wells. The C(t) term is synchronized to the same frame across wells. Therefore, the transformed background signal curve used may be s(g(t))+C(t instead of z(g(t)).

The function s(t) may be modeled by a natural spline with 5 interior knots that are concentrated after the initial change-point (at $t_0+0, 3, 7, 13, 29, 47$, and the last frame of the rise, for example). This is a linear-model fit to the data using a natural spline basis (z(t)~ns(time)). C(t) may then be set as z(t)−s(t) as an approximation to the individual frame noise term. This may have only slight impact in well-behaved experiments, but may provide better results when there is electronic noise.

The change-point may be computed for a small patch of the reactor array by looking at the reference signal and the frames in which the signal sharply increases above background. The same change-point may be used for the entire patch that is processed. This allows re-use of the same model matrix when doing the quadratic fit, which is desirable when looking at the same frames. This also improves the speed of doing the fits for each well.

As the sequencing operation progresses through further flows over the reactor array, the characteristics of the wells may shift over time. For example, the pH of the nucleotides or the pH buffering properties in the well may change over time (e.g. due to extension of the polynucleotide strands, washing away of polymerase, etc.). As such, in some cases, the model may be refitted to a later 0-mer flow.

In some cases, the parameter(s) of the time warping function may be updated by a linear operation for faster computational processing. In some cases, the linear operation may involve updating the parameter(s) of the time-warped empty well function using the derivative of the time warping function. For small changes in the time warping parameter(s), a shift in parameters may be approximated by the derivative for the current 0-mer incorporation background estimate scaled by the shift in the parameter(s). This allows correction of the current time warping parameter(s) to reflect the data without much computation by simply projecting the observed data onto the appropriate derivative. That is, $z=\omega+(\delta\times\omega')$, where z is the shift in parameter(s), $\omega$ is the current 0-mer incorporation background and where $\delta$ is the small change in the parameter(s). The following may be used to estimate $\delta$: $\delta=o\times\omega'$, where o is the observed data.

In an exemplary embodiment, an estimate in the shift in parameter(s) may be made without altering the incorporation signal (thus allowing maintenance of the incorporation signal). The estimate of the unknown shift in parameter(s) may be made such that, regardless of the amount of incorporation signal detected, it does not interfere with the estimation. One manner of accomplishing this is by modifying the vector that is being projected onto it to make it orthogonal to the incorporation signal shape. That is, we estimate $\delta=o\times(\omega'-(\omega'\times I^2)$, where we have subtracted o, the component of $\omega$ that corresponds to the incorporation signal I. This cancels out the major contribution of any incorporation signal present in the data. This allows tracking of the changes in the well behavior as it affects background and reveals the incorporation signal component of the observed count.

The models described above may be further refined by taking into consideration that there may actually be three components to the sensitivity of the quadratic time warp to small changes in the parameters, respecting three parameters: $t_0$ controlling the start of the warp, the linear component a, and the quadratic component b. Given a time warped background z(g(t)), the derivatives are z'(g(t)), z'(g(t)×t), $z'(g(t)\times t^2)$ with respect to each component of the time warp function g(t).

The function z'(g(t)) is almost co-linear with the incorporation signal. Assuming that $t_0$ is estimated reliably, the contribution of z'(g(t)), which has a steep rise at the beginning followed by an exponential decay, may be ignored. This leaves two relevant components, both of which have regions of frames that are very different to the typical incorporation signal. In an exemplary embodiment, under the assumption that the linear term in the time warp dominates, the model $\omega'=z'(g(t))\times t$ is the relevant derivative of the time warp function.

Figure 16A:
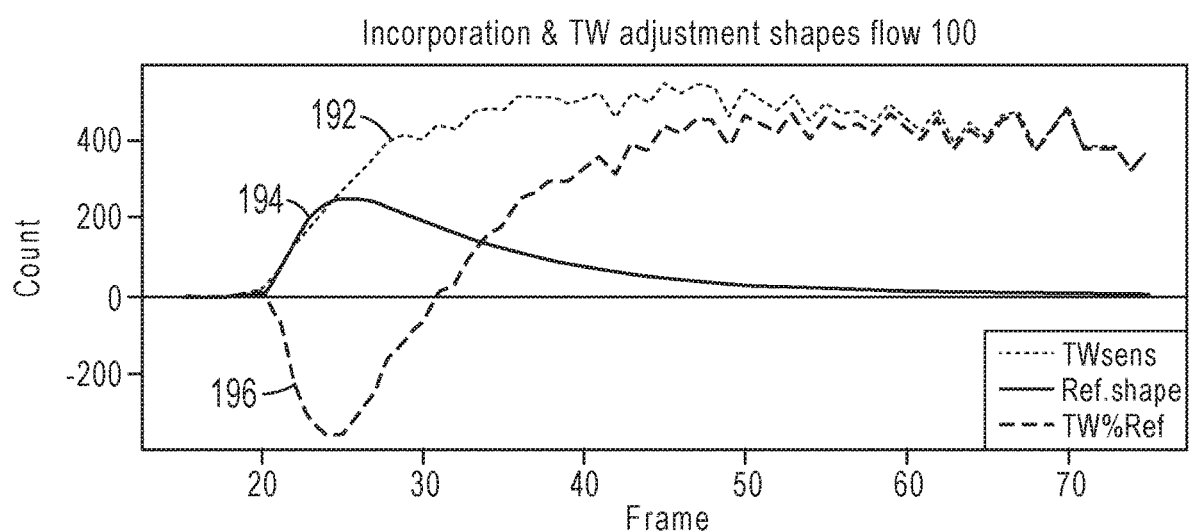
FIGS. 16A and 16B demonstrate the sensitivity of a quadratic time warp to shifts in the linear parameter.
Figure 16B:
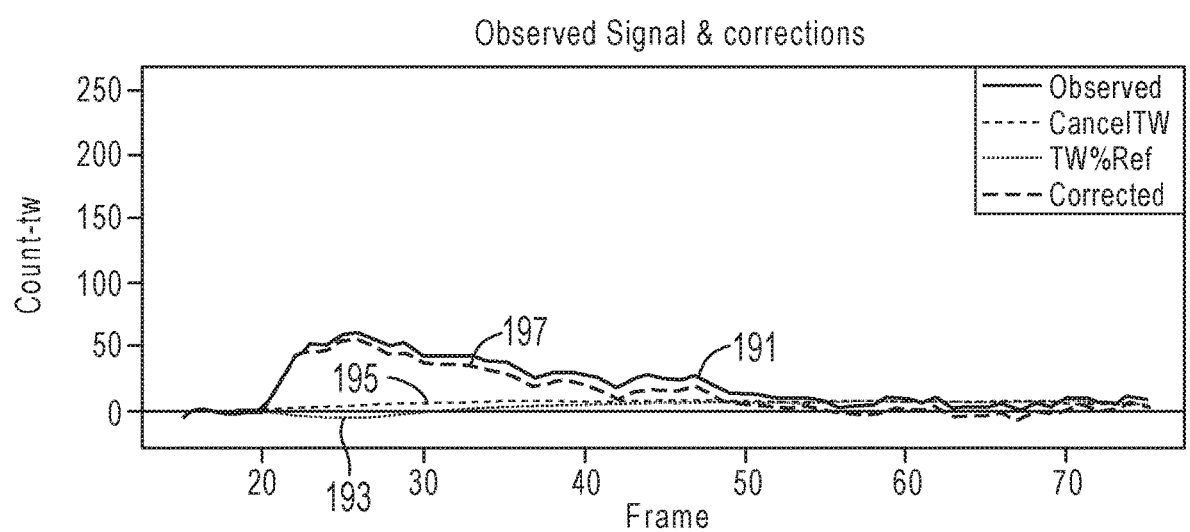

FIG. 16A shows various data from flow number 100 in a well. The dashed line 192 represents the sensitivity of the quadratic time warp to shifts in the linear parameter. Because this is an empirical derivative, there is some roughness in the line, but applying a smoothing would improve the roughness. The line 194 represents the reference incorporation signal shape and line 196 represents the sensitivity curve after making the sensitivity orthogonal to the reference incorporation signal 194. In FIG. 16B, line 191 shows the results of the operation after removing the typical time warp and other shifts due to the time warp. The observed data may be projected onto the sensitivity curve 193 to obtain the shift in the time warp parameter. Applying this shift results in dashed line 195, which may then be subtracted from line 191 to obtain the corrected data for this flow, which is shown as line 197.

After employing orthogonalization, the value obtained is still slightly dependent on the incorporation signal. Therefore, in order to preserve as much of the incorporation signal as possible, especially for large homopolymers, it may be useful to keep the estimate of $\delta$ as robust as possible. As such, in some cases, it can be assumed that flows that occur close to one another in time are likely to be similar, allowing the estimate of $\delta$ to be shrunk to the trend observed in past flows. One way of doing this is to use an exponential smoothing algorithm based on previous values of $\delta$ as an estimate. This allows estimation of a reference level for $\delta$ using only past flows, rather than future flows, so that the correction can proceed as the flows become available. When modeling signals that have a trend, it may be appropriate to use a double exponential smoothing to construct a reference for shrinking the values in any given flow. Because this trend is not necessarily linear (e.g. signal counts may abruptly jump if a bead washes out from a well), in some cases, using an exponential smoothing algorithm may be more appropriate than a linear fit. In some cases, a double exponential smoothing may be used to estimate the parameter(s) as it drifts over time, with a data smoothing factor α that monitors the constant value (starting point) and a trend smoothing factor β that monitors the trend over time.

Figure 17A:
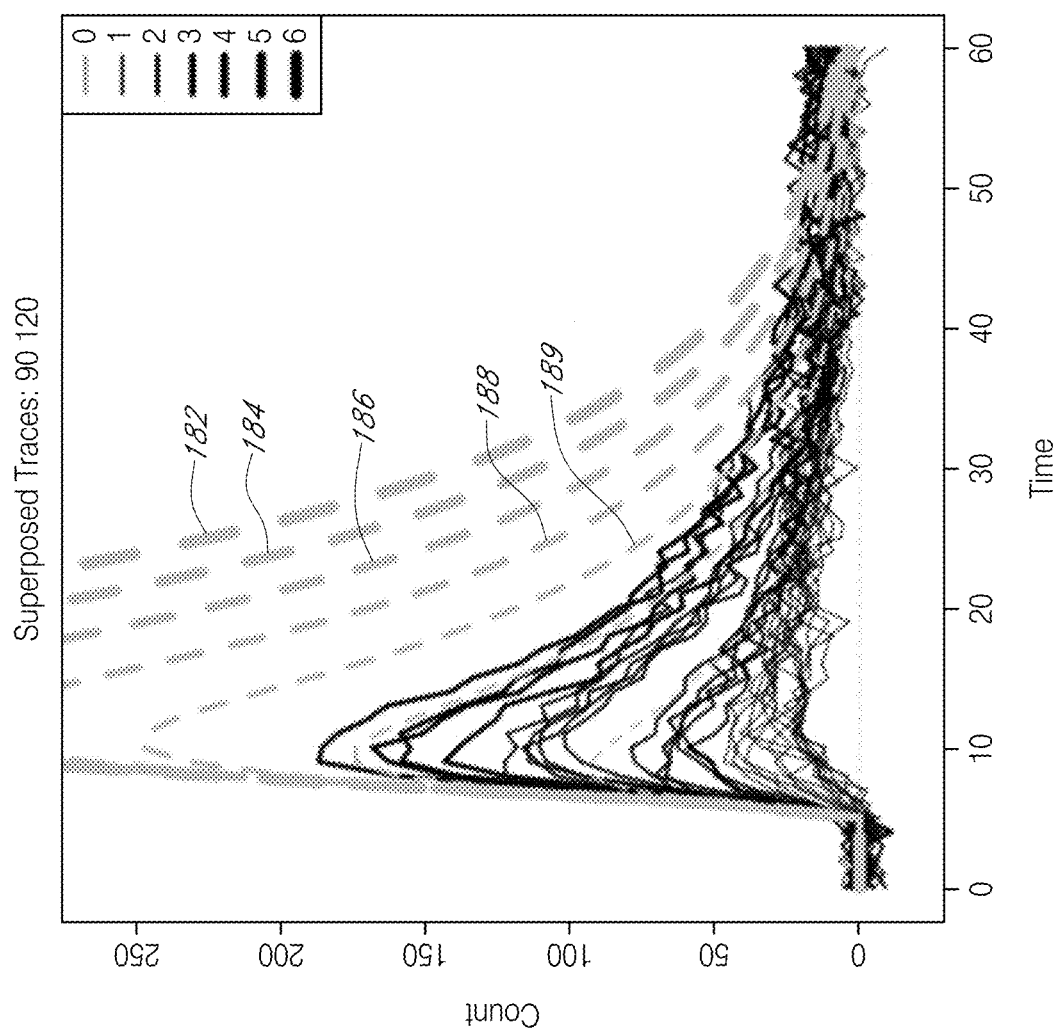
FIGS. 17A-17D show various data relating to shifts in a time warping parameter.
Figure 17B:
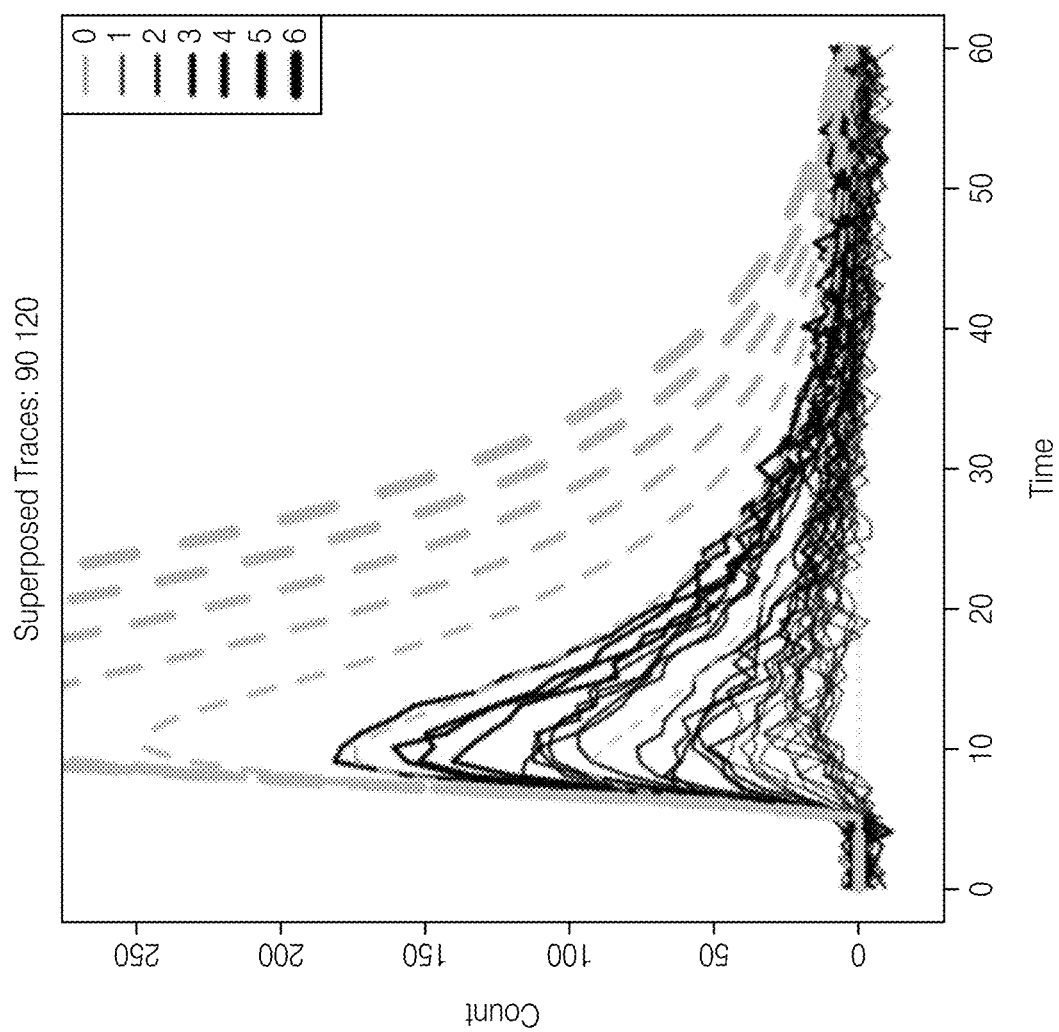
Figure 17C:
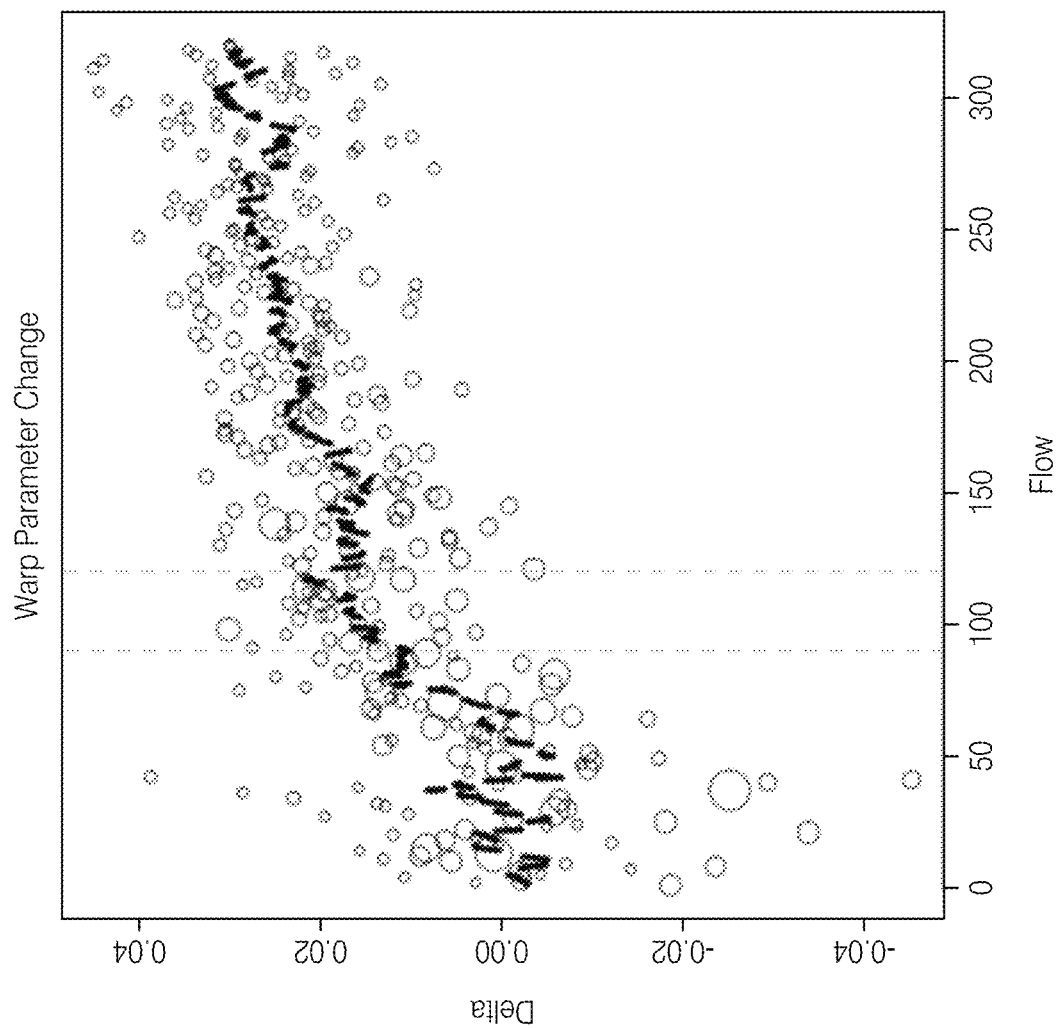
Figure 17D:
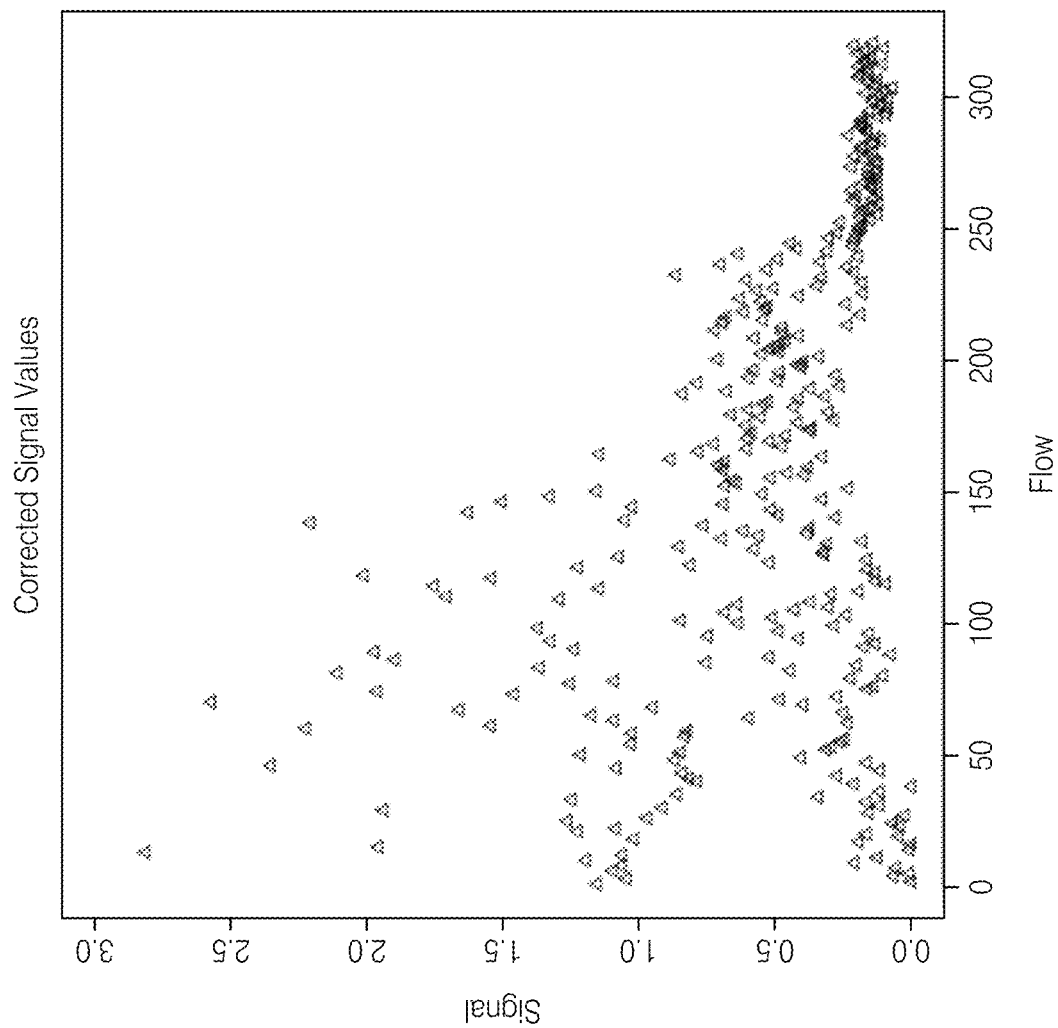

FIGS. 17A-17D show readings that are taken from the same well shown in FIG. 16, but with a plot of superimposed tracings of the observed data for flows 90-120. FIG. 17A shows uncorrected tracings (note that there is a slight deviation from the x-axis at the right hand side of the plots). These slight increases create positive biases in estimated signal. Even very slight biases may interfere with accurate basecalling routines. The dashed lines show incorporation signal curves corresponding to various n-mer lengths, indicated in the legend as follows: n-mer length of 6 (182), n-mer length of 5 (184), n-mer length of 4 (186), n-,er length of 3 (188), and n-mer length of 2 (189), FIG. 17B shows the same traces after correction and demonstrates that this bias is eliminated. FIG. 17C shows the estimated shift in the warping parameters per flow. The estimates for individual flows are variable, but FIG. 17C shows a clear systematic trend. FIG. 17C illustrates both a linear estimate and a tracking exponential smooth as more systematic estimates of the shift in warping parameters. FIG. 17D shows the raw signal outputs (triangles represent the uncorrected data and circles represent the corrected signal). The uncorrected signals systematically overestimate the signal in later flows. This is especially true after the bead stops sequencing at around flow 250 (when the signal should be dropping to zero).

Figure 18A:
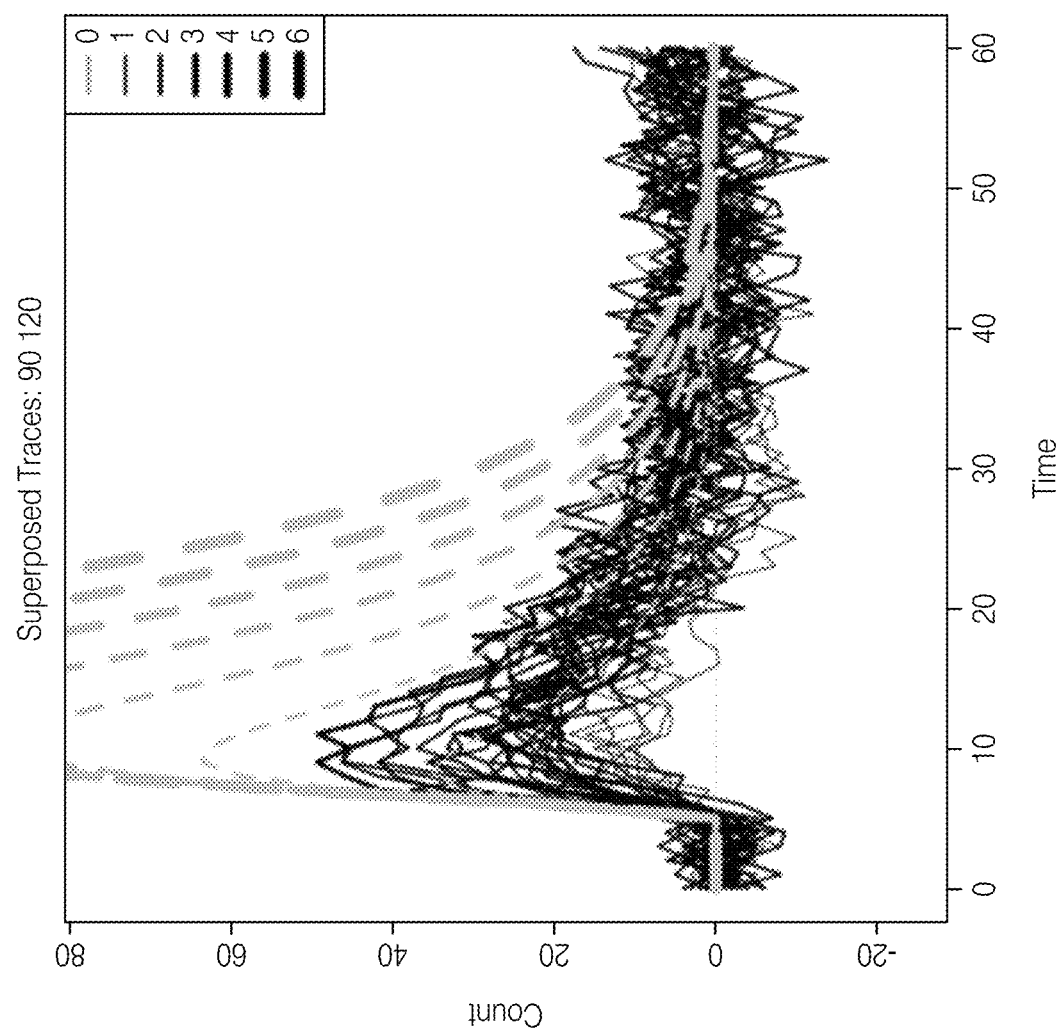
FIGS. 18A-18D show the same type of data as in FIGS. 17A-17D, but for a different well.
Figure 18B:
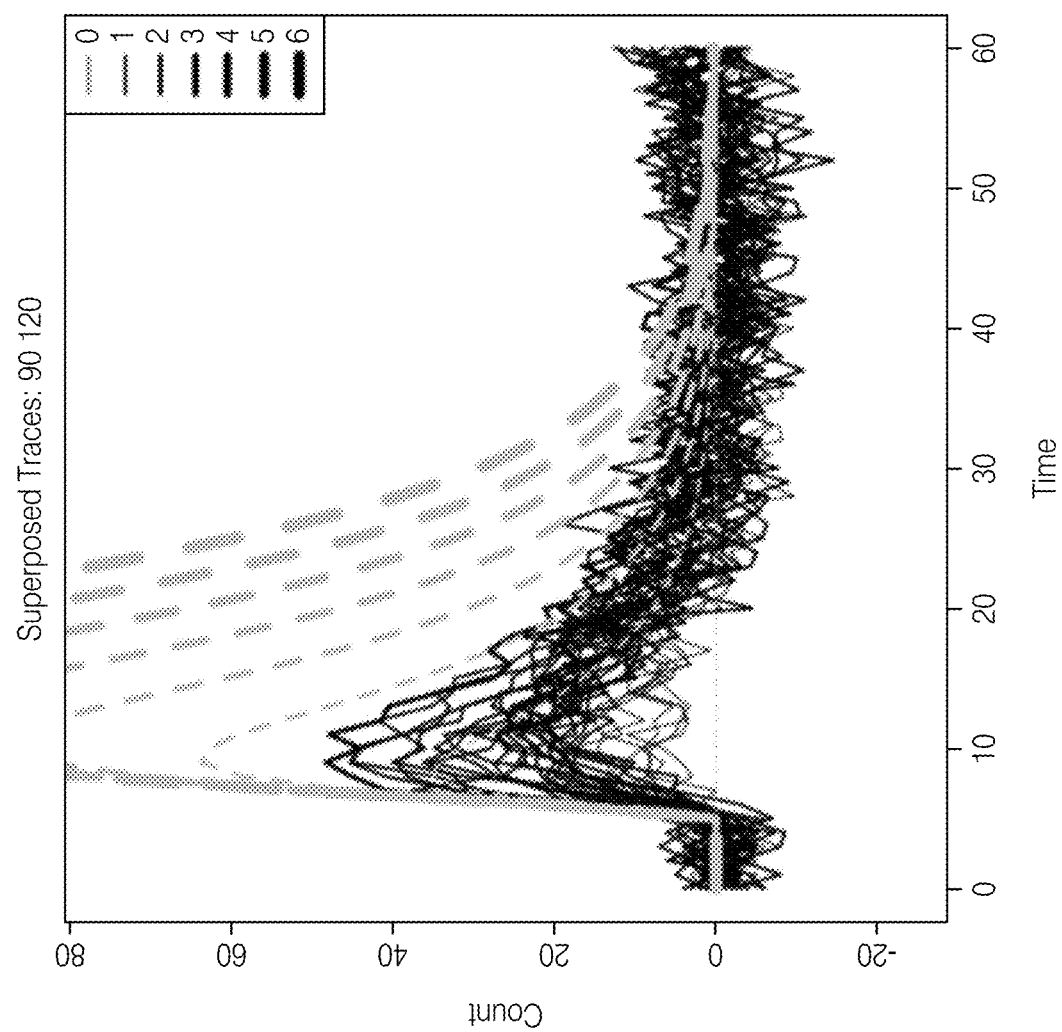
Figure 18C:
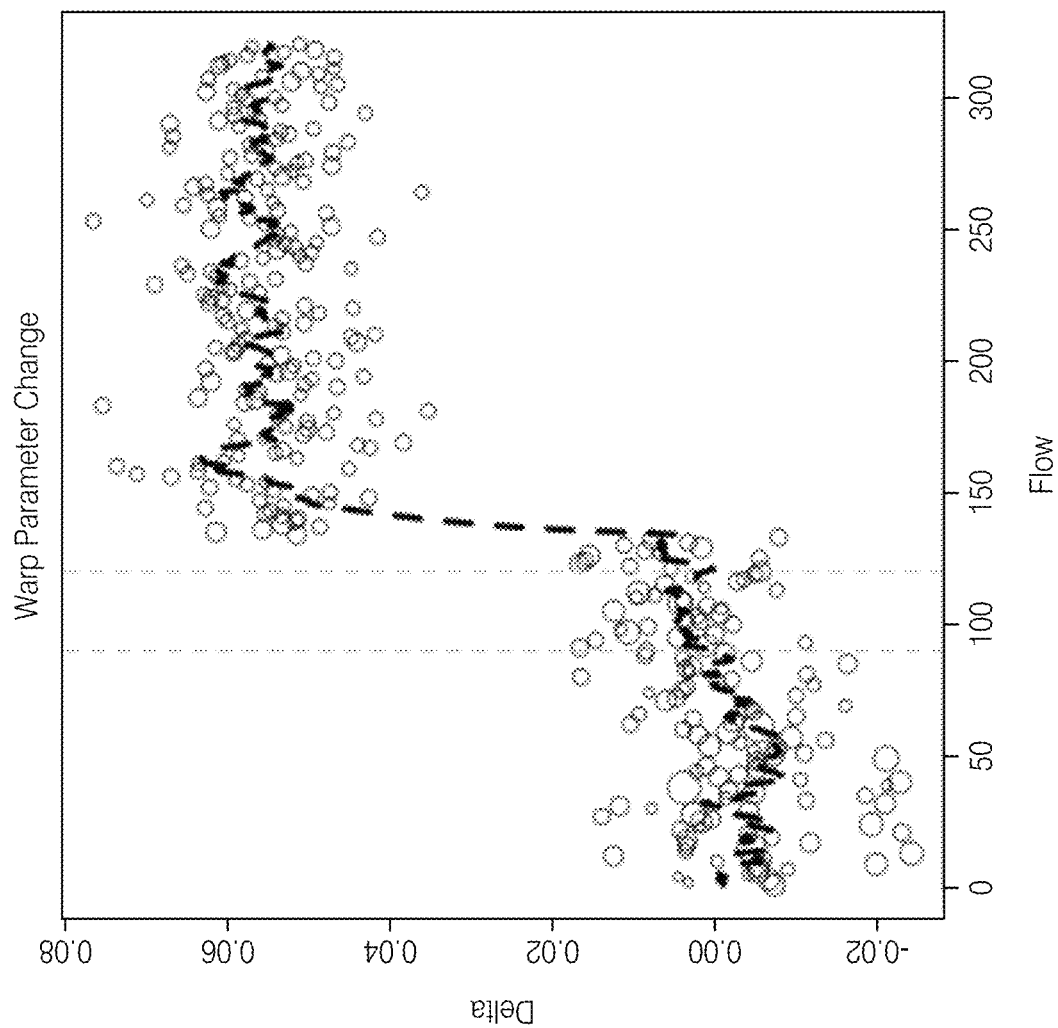
Figure 18D:
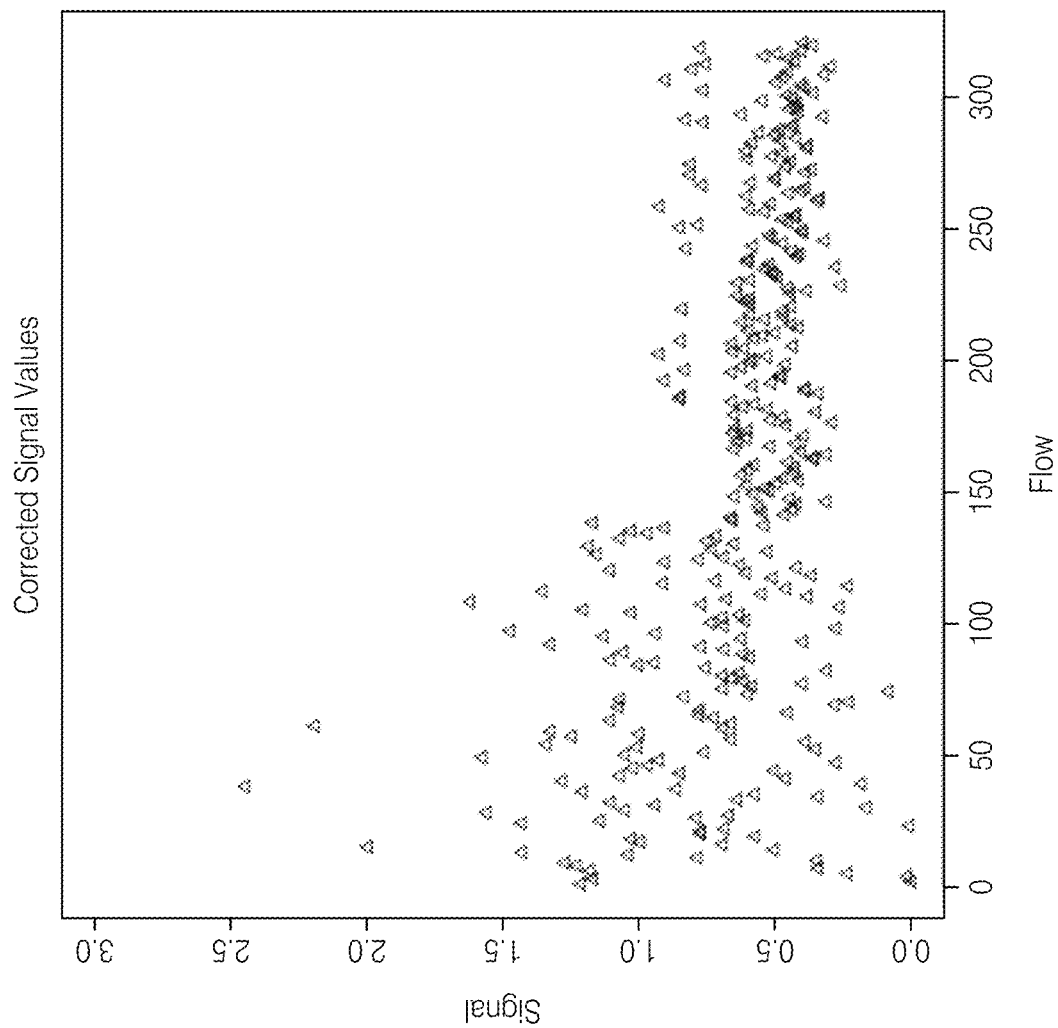

FIGS. 18A-18D show tracing from a different well. FIG. 18A shows uncorrected traces and FIG. 18B shows the same traces after correction. FIG. 18C shows the estimated shift in the time warping parameters per flow. FIG. 18C illustrates both a linear estimate and a tracking exponential smooth as more systematic estimates of the shift in warping parameters. FIG. 18D shows the raw signal outputs (with triangles representing the uncorrected data and circles representing the corrected signal). FIG. 18C shows an abrupt change in warp parameters around flow 130. This is likely due to the bead washing out of the microwell as there is no systematic incorporation signal after this point. This causes the uncorrected signal to yield spuriously large values because the rapid pH rise is mimicking an incorporation signal. The corrected signal is better behaved, but still not perfect (ideally, it should drop to zero). In this particular instance, a linear trend fits the data poorly and the smooth tracker would improve the fit.

The incorporation signal obtained from the above-described process can be analyzed in any suitable manner to estimate the number of nucleotides incorporated into the polynucleotide strand. In some cases, the peak of the incorporation signal curve may be used to estimate the number of nucleotides incorporated into the polynucleotide strand. In some cases, the incorporation signal may be analyzed empirically by comparing to a set of reference signal curves. For example, the incorporation signal may be compared to a signal shape library that comprises multiple signal shapes that are associated with different n-mer lengths of nucleotide incorporations. The incorporation signal may be compared against the representative signal shapes in this library to identify the closest matching signal shape. The n-mer length associated with the closest matching signal shape may then be used to estimate of the number of nucleotides incorporated into the polynucleotide strand.

In some cases, the analysis of the incorporation signal may involve using a function that models the incorporation signal. For example, the function may have a parameter for the n-mer length and the function can be fitted to the incorporation signal to solve for the parameter for the n-mer length. Based on the parameter result, an estimate of the number of nucleotides incorporated into the polynucleotide strand can be determined.

In some cases, the signal shape library or incorporation signal function may be constructed using a catenary multi-compartment model of the polymerase on the polynucleotide strand, as described in U.S. Provisional Application Ser. No. 61/428,097 (filed 29 Dec. 2010; Earl Hubbell), which is incorporated by reference herein in its entirety. The catenary multi-compartment model comprises a series of two or more compartments that represent molecular locations on the homopolymer length.

Figure 19:
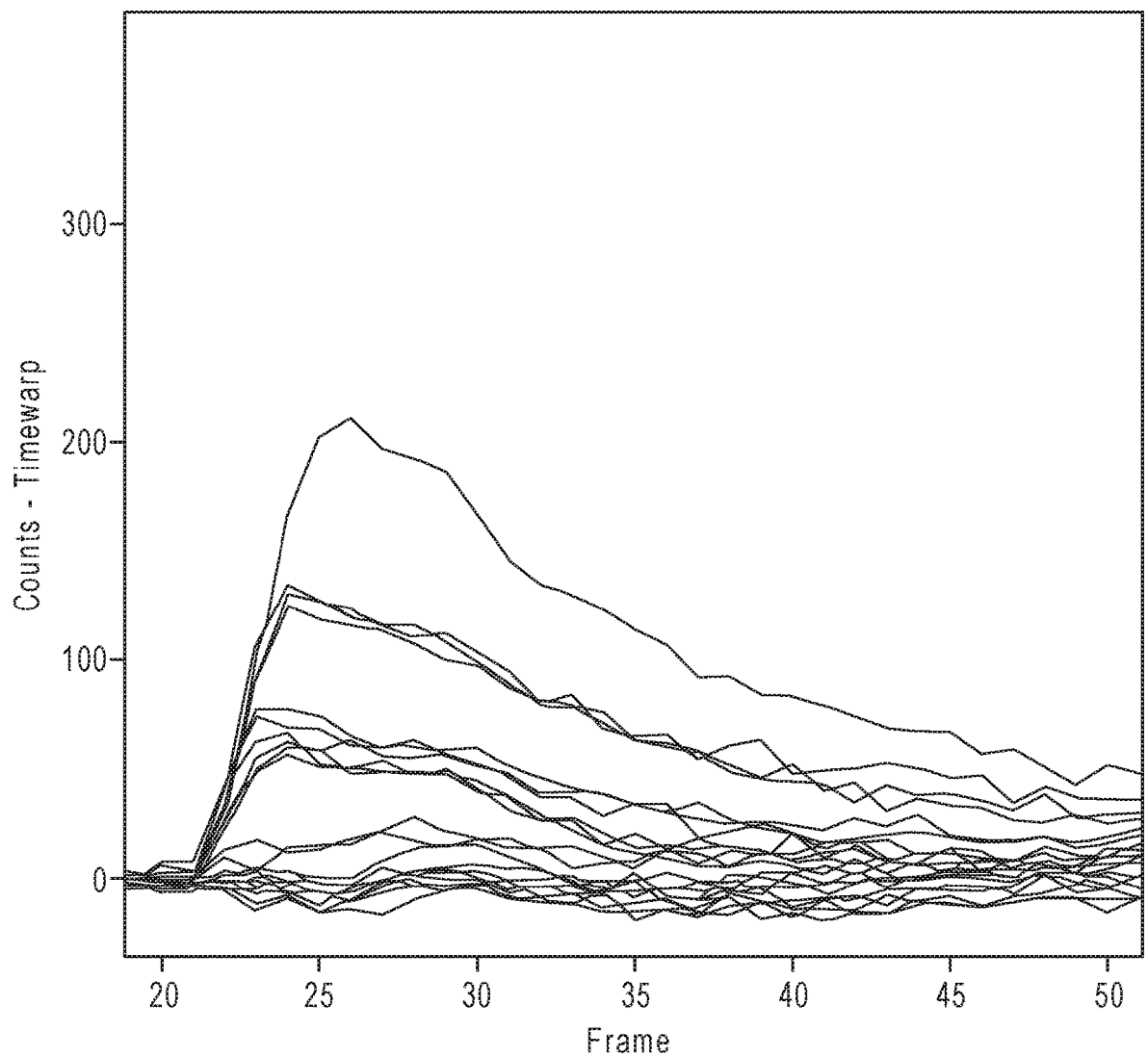
FIG. 19 shows an exemplary set of incorporation signals from a well.

FIG. 19 shows a set of incorporation signals from a well over multiple flows to give the incorporation signals for these flows. These incorporation signals are superimposed upon one another. In an embodiment, the present invention provides a modeling technique to estimate the homopolymer n-mer length that is represented by these incorporation signal curves. A separable regression technique may be used to obtain the shape of basis functions describing typical nonlinear signals (e.g. exponential decay curves at varying rates). The process of finding the coefficients of each basis function then becomes a linear modeling task. In this manner, the more difficult nonlinear task of analyzing shapes can be separated from the easier linear task of interpreting a signal using a shape dictionary. Accordingly, approximate models for incorporation signals of varying rates and homopolymer lengths are useful for constructing a shape library that will be fit to the data.

The generation of hydrogen ions by polymerase-catalyzed nucleotide incorporation reactions on a polynucleotide strand can be modeled on the basis of the molecular/physical location of the polymerase. In the simplest application of this model, for a 1-mer incorporation, there is a first logical compartment that is the molecular location of the polymerase ready to act on a polynucleotide strand and a second logical compartment that is the molecular location of measured hydrogen ions. As the polymerase incorporates a base, the polymerase moves from the first compartment to the second compartment, resulting in the addition of a hydrogen ion to the second compartment for measured hydrogen ions. There is a rate at which polymerase acts to incorporate nucleotide bases and a rate at which hydrogen ions diffuse away from the second logical compartment for measured hydrogen ions. Therefore, 1-mer incorporations can be modeled as being characterized by two rates: one for polymerase action and one for hydrogen ion diffusion, each capable of being represented by a logical compartment.

In a similar manner, a 2-mer incorporation can be modeled using three logical compartments: the first logical compartment is the polymerase standing at a molecular position ready to incorporate two nucleotides, the second logical compartment is the polymerase standing at a molecular position ready to incorporate one nucleotide, and the third logical compartment is the molecular location of the generated hydrogen ions. In the case of a 2-mer incorporation, there are two potential rates for polymerase activity: a rate for two bases remaining and a rate for one base remaining (although they may have the same per-base rate). Similarly, a 3-mer incorporation may be modeled as having four compartments, and so on.

Figure 20:
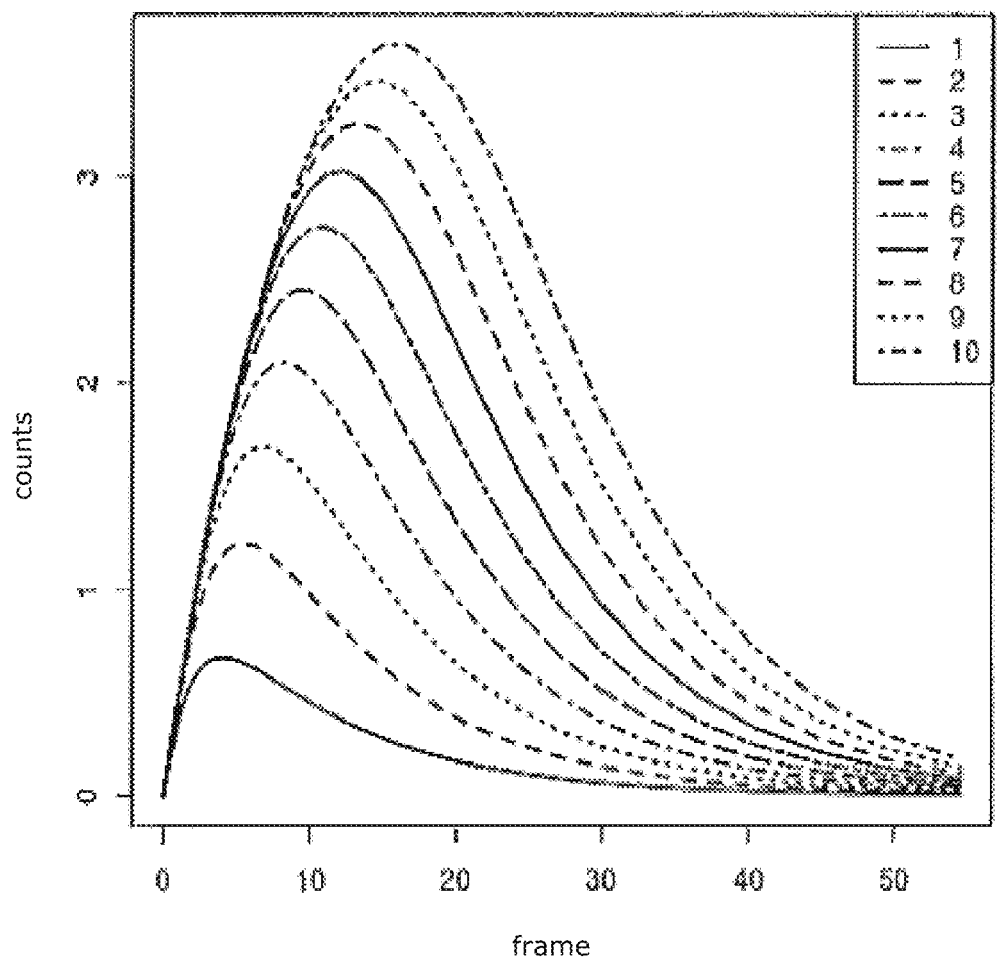
FIG. 20 shows examples of incorporation signals of various lengths as exponential curves.

These logical compartments can be expressed by a set of equations. FIG. 20 shows incorporations signals of various n-mer lengths modeled as exponential curves, which are shown superimposed upon one another. The top-most curve represents a 10-mer incorporation signal and the bottom-most curve represents a 1-mer incorporation signal, with the curves in between representing intermediate n-mer lengths (i.e. 2-mer, 3-mer, and so on). Let k represent a constant for the polymerase activity rate and let m represent a constant for the rate of loss for measured hydrogen ions. Thus, for the compartment where polymerase has acted on zero bases, $x'_0=-kx_0$ describes the rate of loss for polymerase ready to act, and $y'=kx_0-my$ describes the rate of loss of hydrogen ions by diffusion. Accordingly, $x_0=\exp(-kt)$ solves the rate for polymerase ready to act, and $y=\exp(-mt)-\exp(-kt)$ solves the measured hydrogen ion equation ($k/[k-m]$ is the multiplicative constant required here).

In general, for n bases of incorporation, the mass balance equations require that the polymerase leave one compartment and enter another compartment, producing an equivalent number of hydrogen ions. Equation set 1 below can be solved by observing that, as a "lower triangular" matrix, the eigenvalues of the linear system are −k (multiplicity n) and −m, implying the solutions are sums of exponentials with rates −k and −m, with a polynomial term applying to the rate (−k) terms as illustrated by Equation set 2 below.

$$x'_0 = -kx_0$$
$$x'_1 = kx_0 - kx_1$$
$$x'_2 = kx_1 - kx_2$$
$$...$$
$$x'_j = kx_{j-1} - kx_j$$
$$...$$
$$x'_n = kx_{n-1} - kx_n$$
$$y' = kx_0 + kx_1 + ... + kx_n + my$$
$$\text{Equation set 1}$$

$$x_0 = e^{-kt}$$
$$x_1 = kt \cdot e^{-kt}$$
$$x_2 = \frac{(kt)^2}{2!} e^{-kt}$$
$$...$$
$$x_n = \frac{(kt)^n}{n!} e^{-kt}$$
$$...$$
$$x_j = \frac{(kt)^j}{j!} e^{-kt}$$
$$y = a_0 x_0 + a_1 x_1 + ... + a_n x_n + b \cdot e^{-mt}$$
$$\text{Equation set 2}$$

The constants in front of each term for Equation set 2 must be determined. The differential equation relations combined with the functional form for y combine to imply (after some rearrangement) Equation set 3 below.

$$a_0 = \frac{k}{m-k}(1 - a_1)$$
$$a_j = \frac{k}{m-k}(1 - a_{j+1})$$
$$a_n = \frac{k}{m-k}(1 - a_{n+1})$$
$$a_q = p \frac{1 - p^{q+1}}{1 - p}, \text{ where } p \text{ is } \frac{k}{k-m}$$
$$\text{Equation set 3}$$

Parameter b is chosen to satisfy the implied natural boundary requirement that all the polymerase starts in compartment zero and no hydrogen ions have yet been generated. This yields Equation 4 below for the amount of hydrogen ions measured.

$$y = -p \left[ z_n e^{-mt} - \sum Z_j x_{n-j} \right] \text{ where}$$
$$z_n = p \frac{1 - p^{n+1}}{1 - p}$$
$$\text{Equation 4}$$

Thus, for given rate constants for polymerase activity and hydrogen ion diffusion, and a given homopolymer length, the measured hydrogen ion level at time t can be determined analytically, as well as the fraction of polymerase at different states of action.

Figure 21A:
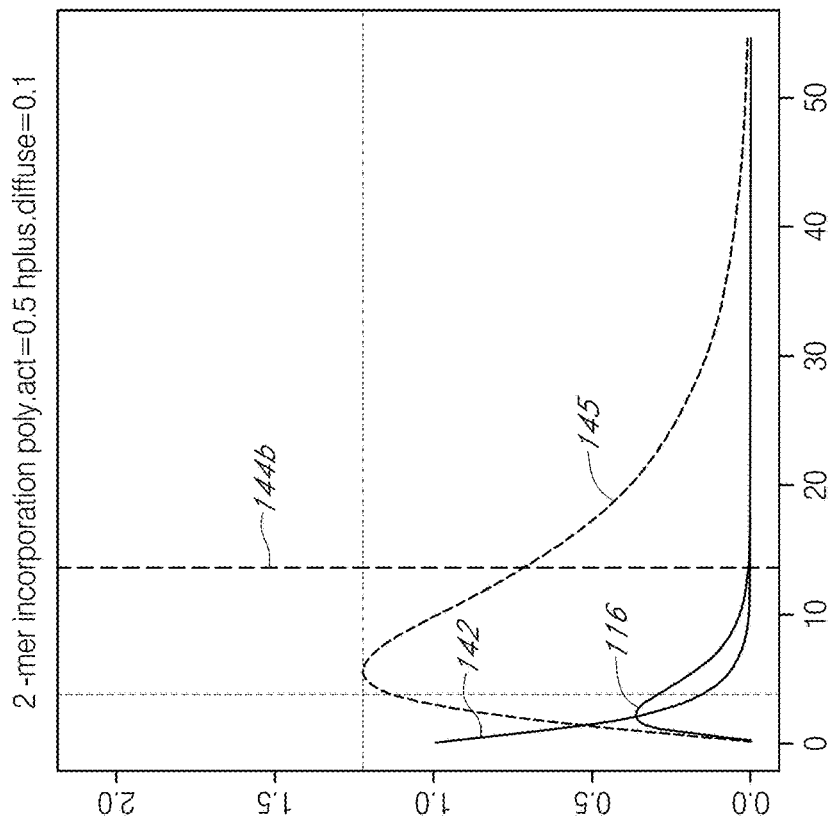
FIGS. 21A-21D show various plots that demonstrate the behavior of an exemplary incorporation signal model.

FIGS. 21A-21D show various plots that demonstrate the behavior of the above-described model. In FIG. 21A, plot line 142 shows the amount polymerase ready act, which is at a maximum ($x_0$) initially and decreases at a rate of $-kx_0$. Plot line 143 is an incorporation signal for a 1-mer incorporation, which is the measured hydrogen ions. As explained above, this is equal to the positive value of the decrease in the amount of polymerase ready to act, reduced by the amount of hydrogen ions lost to diffusion; or y'=$kx_0$−my, for a 1-mer incorporation. Line 144a represents hydrogen ion diffusion of 0.1.

Figure 21B:
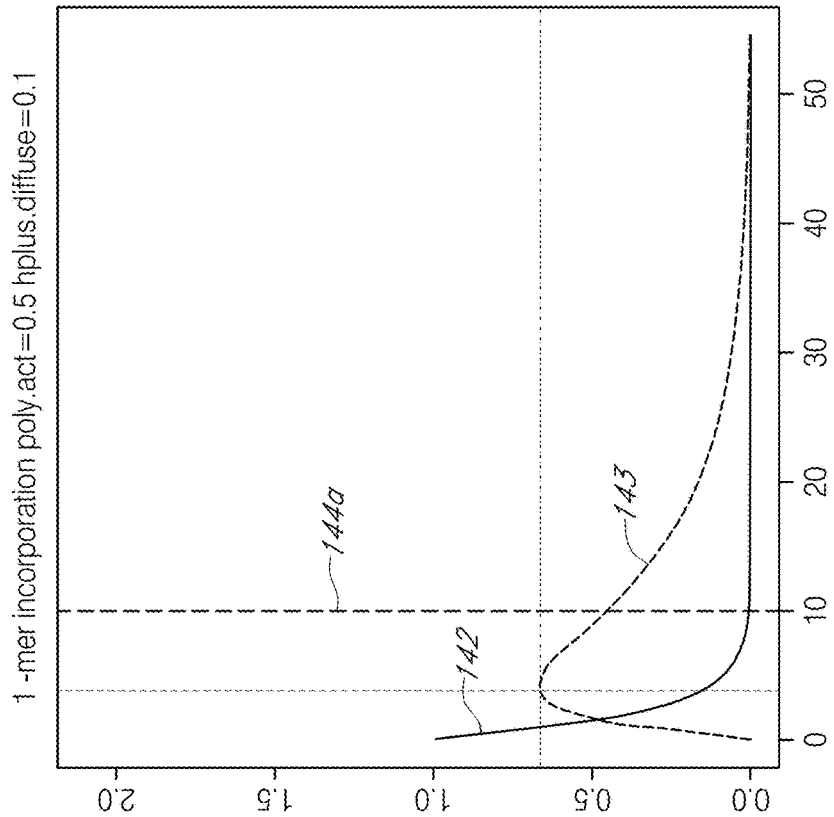

FIG. 21B demonstrates a 2-mer incorporation. As in FIG. 21A, plot line 142 shows the amount of polymerase ready act. The amount of polymerase ready to act decreases at a rate of $-kx_0$ and hydrogen ions are generated at a rate of $kx_0$. Plot line 145 is the incorporation signal for a 2-mer incorporation, which is essentially equal to the incorporation signal for the 1-mer incorporation as shown by plot line 143 in FIG. 21A plus the signal shown by plot line 116 in FIG. 21B. Line 144b represents a hydrogen ion diffusion of 0.1. In this example, the rate of change in the polymerase remains constant regardless of the n-mer length being incorporated. Thus, the second incorporation in a 2-mer incorporation will create hydrogen ions at a rate of $kx_0$.

Figure 21D:
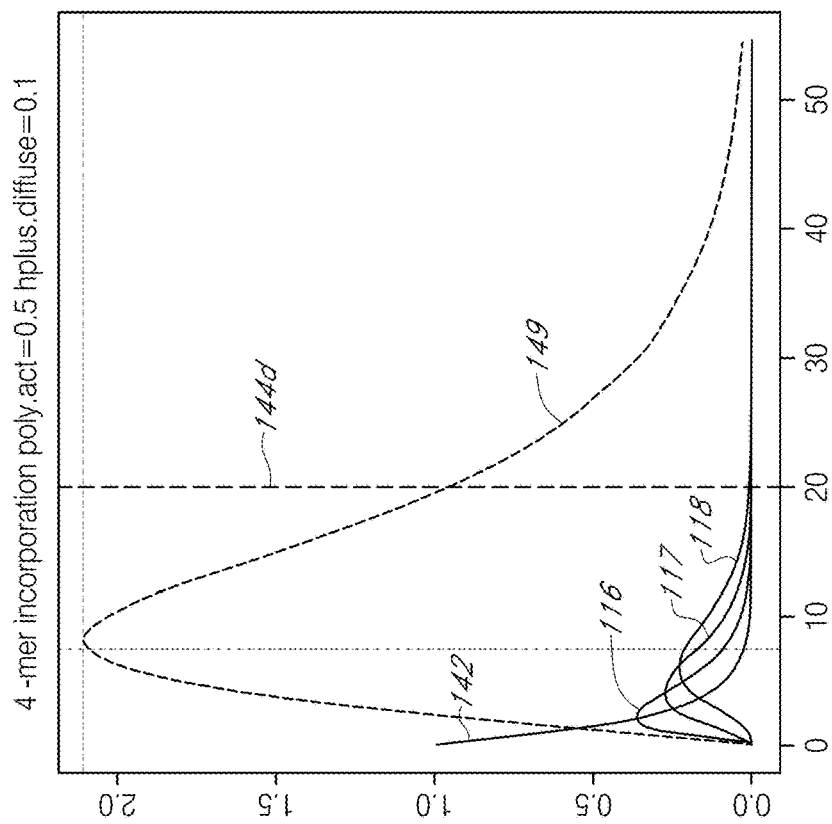
Figure 21C:
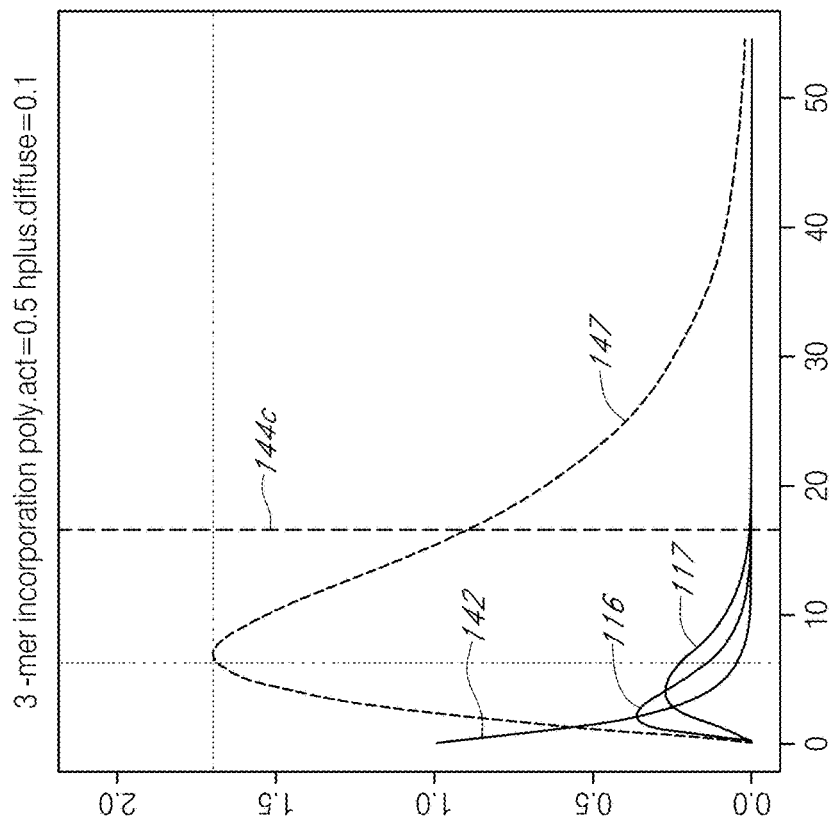

FIG. 21C demonstrates a 3-mer incorporation. Plot line 147 is the incorporation signal for a 3-mer incorporation, which is essentially equal to the incorporation signal for the 2-mer incorporation as shown by plot line 145 in FIG. 21B plus the signal shown by plot line 117 in FIG. 21C. Line 144c represents a hydrogen ion diffusion of 0.1. FIG. 21D demonstrates a 4-mer incorporation. Plot line 149 is the incorporation signal for a 4-mer incorporation, which is essentially equal to the incorporation signal for the 3-mer incorporation as shown by plot line 147 in FIG. 21C plus the signal shown by plot line 118 in FIG. 21D. Line 144d represents a hydrogen ion diffusion of 0.1.

This solution may be used to generate shape libraries for given rate constants or used in a nonlinear solver to fit the data. Rate constants can be uncertain and different pairs of rates can yield similar curves. Thus, curves may be fit only to sources of amplified DNA (such as wells containing multiple copies of the same DNA) having higher signal-to-noise ratios and then extrapolation may be used for wells with lower signal-to noise ratios.

A generalization is to model the whole sequence as comprising multiple compartments, with intermittent changes in the dynamics from one flow to another flow. The form of the solution may still be the same (sums of exponentials with polynomial terms), but the boundary conditions may be different, as each flow can change the initial distribution of polymerases between compartments.

In some cases, the time-warped empty well function may be used to identify wells that behave outside of the typical behavior, i.e., outlier wells, which may be due to wells that contain dud particles, or are located outside the fluid flow or trapped under a fluid bubble. For example, this may be performed using the technique described in U.S. Provisional Application Ser. No. 61/428,097 (filed 29 Dec. 2010; Earl Hubbell), which is incorporated by reference herein in its entirety. This identification of an outlier well may be based on the quality of the fitting of the time-warped empty well function to the output signal from the loaded well. A poor fitting (e.g. least-squares residuals exceeding a certain threshold) may identify the well as an outlier.

A reactor array can be viewed as a "bubble plot," in which each well is depicted as a pixel to graphically illustrate how much each well of the reactor array deviates from the mean. A bubble plot can show bubbles and other artifacts on the reactor array by the atypical behavior of affected wells. As such, one approach to detecting outlier wells is by comparing the signal response with that of a typical well, such as a median well signal response.

Figure 22:
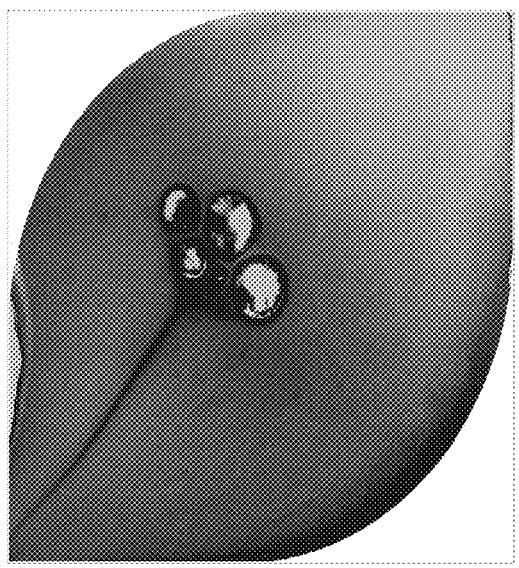
FIGS. 22-24 show an exemplary bubble plots of a reactor array.

FIG. 22 shows an example bubble plot of the wells on a reactor array. The signal curve from each well is compared to that of a median signal curve. The intensity of the plot at each well is the logarithm of the standard deviation of the signal curve across all frames from the average value, i.e., lighter intensity represents relatively larger variation and darker intensity represents relatively smaller variations. The distortions in the middle of the plot represent bubbles in the reagent fluid.

Figure 23:
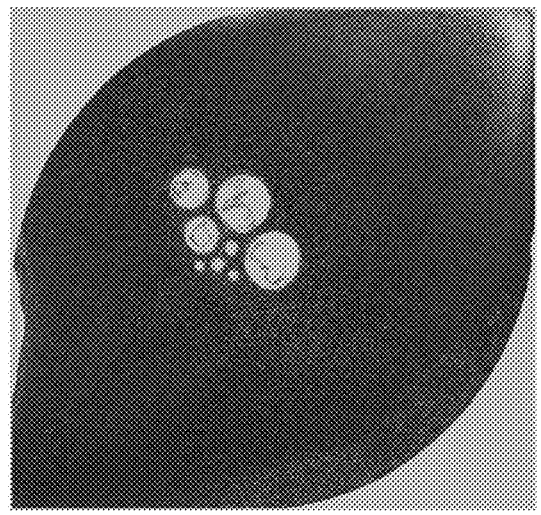

FIG. 23 shows another bubble plot of the same reactor array shown in FIG. 22, but using a more sensitive methodology. In FIG. 23, the signal curve from each well is compared to that of a time-warped median signal curve. The intensity of the plot at each well is the logarithm of the standard deviation from the average value of the signal curve across all frames. The white areas have very high residuals (the deviation of observed data from the modeled median signal), indicating that these wells may not be in contact with the reagent fluid, and thus should be excluded from further analysis. Thus, by comparing to the time-warped median signal curve, it may be possible to identify regions on the reactor array having bubbles that impair the flow of reagent fluid into the wells. Signal data obtained from these wells are unlikely to have useful sequencing information, and thus could be excluded from further analysis.

Figure 24:
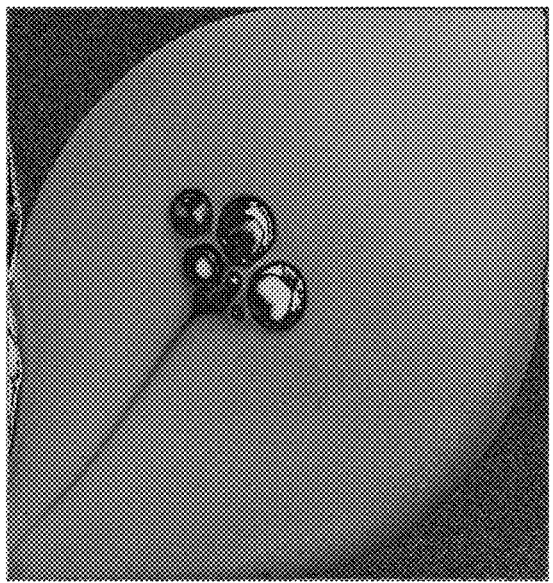

FIG. 24 shows another bubble plot of the same reactor array shown in FIG. 22, but the plot intensity is proportional to the amount of time warping needed for the signal curve in each individual well to match that of the median signal curve. The lighter areas represent wells that reach the median intensity at relatively earlier time frames. The darker areas represent wells that reach the median intensity at relatively later time frames. There is a small difference between wells located at the inlet and wells located at the outlet. Again, the fluid bubbles are readily visible in this plot.

Figure 25A:
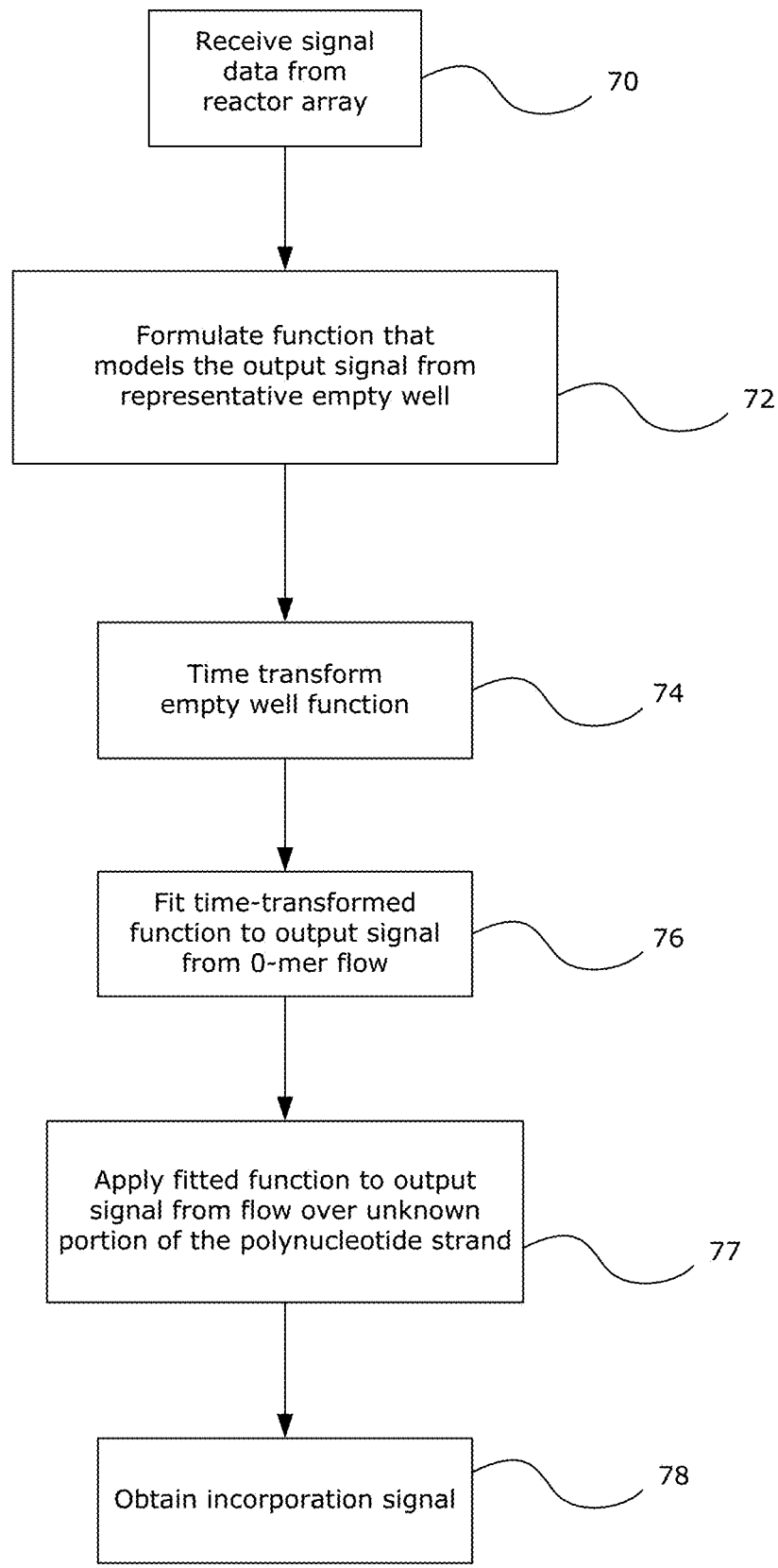
FIG. 25A shows a flow chart illustration of an exemplary embodiment.

FIG. 25A shows a flow chart illustration of a method according to an exemplary embodiment. As shown in step 70, signal data is received from a reactor array. As shown in step 72, a function that models the output signal from a representative empty well is formulated. As shown in steps 74 and 76, this function is time-transformed and fitted to the output signal from a 0-mer flow. As shown in steps 77 and 78, the fitted function is then applied to a nucleotide flow over an unknown portion of the sequence of the polynucleotide strand to obtain an incorporation signal.

Figure 25B:
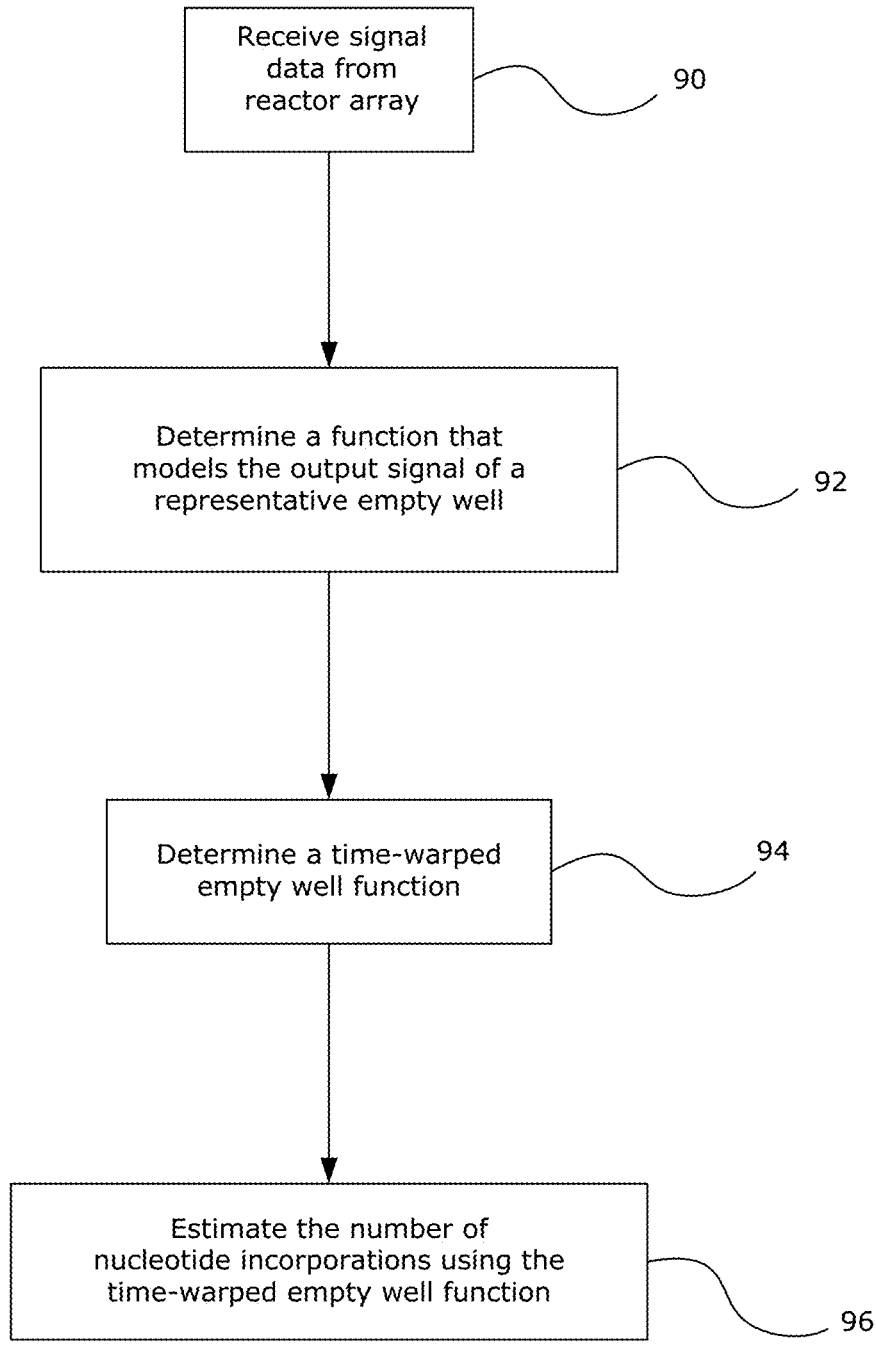
FIG. 25B shows a flow chart illustration of another exemplary embodiment.

FIG. 25B shows a flow chart illustration of a method according to another exemplary embodiment. As shown in step 90, signal data is received from a reactor array. As shown in step 92, a function that models the output signal from a representative empty well is determined. As shown in step 94, a time-warped empty well function is determined. As shown in step 96, the number of nucleotide incorporations is estimated using the time-warped empty well function.

Figure 26:
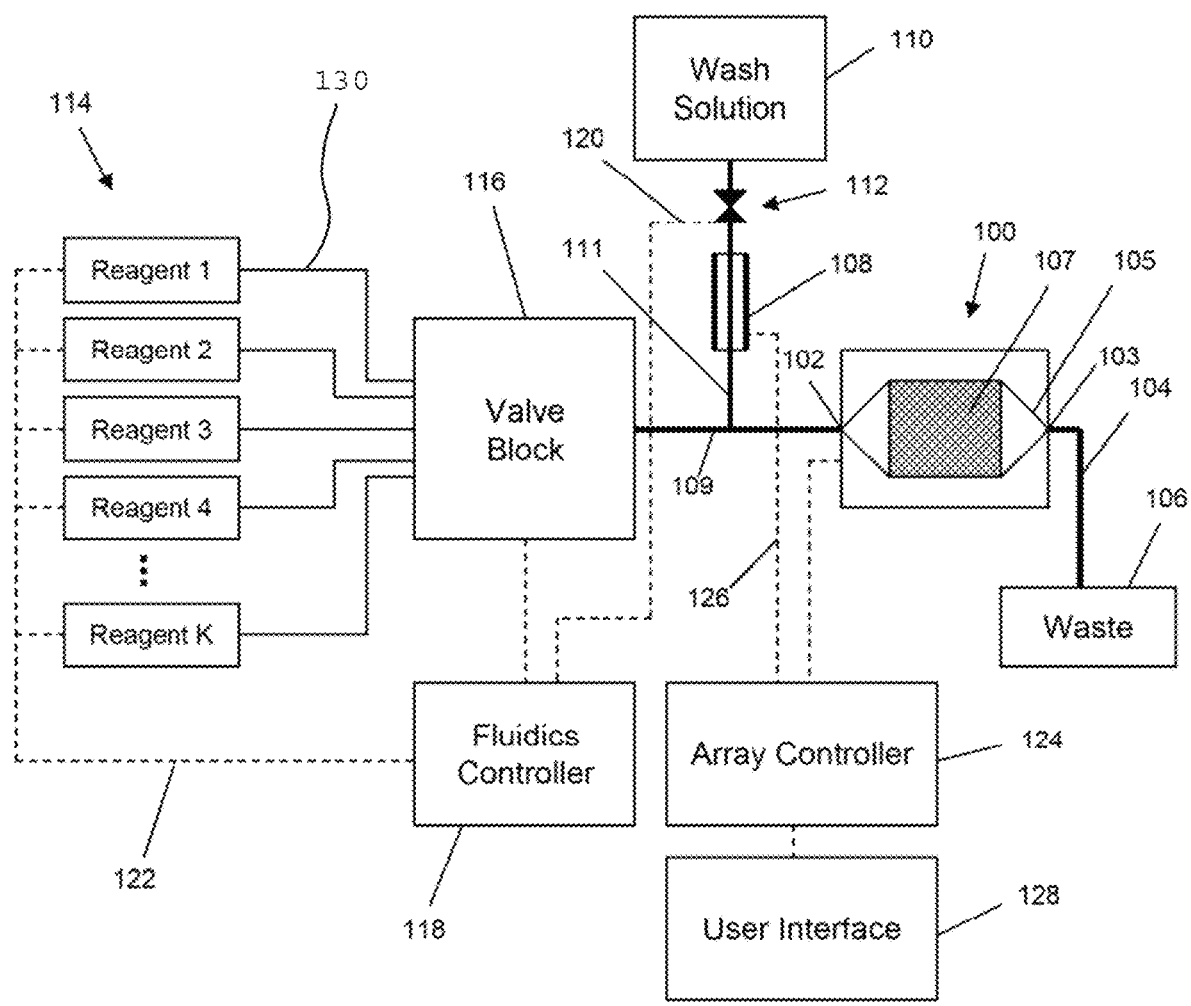
FIG. 26 is a diagram showing a sequencing apparatus according to an exemplary embodiment.

According to an exemplary embodiment, there is provided an apparatus for sequencing polynucleotide strands according to the above-discussed exemplary methods. A particular example of an apparatus of the present invention is shown in FIG. 26. The apparatus of FIG. 26 is configured for pH-based sequencing and includes multiple reservoirs for containing nucleotide reagents 1 through K (114). These reagents contain the nucleotides to be flowed for the sequencing process. The reagents 114 are flowed through fluid passages 130 and through a valve block 116 that controls the flow of the reagents to flow chamber 105 (also referred to herein as a reaction chamber) via fluid passage 109. The apparatus includes a reservoir 110 for containing a wash solution that is used to wash away the nucleotide reagent of the previous step. Reagents are discarded through waste passage 104 into a waste container 106 after exiting the flow chamber 105.

The apparatus also includes a fluidics controller 118, which may programmed to control the flow from the multiple reagent reservoirs to the flow chamber according to a predetermined ordering that comprises an alternate flow ordering, as described above. For this purpose, fluidics controller 118 may be programmed to cause the flow of reagents 114 from the reagents reservoir and operate the valves 112 and 116. The fluidics controller may use any conventional instrument control software, such as LabView (National Instruments, Austin, Tex.). The reagents may be driven through the fluid pathways 130, valves, and flow cell by any conventional mechanism such as pumps or gas pressure.

The apparatus also has a valve 112 for controlling the flow of wash solution into passage 109. When valve 112 is closed, the flow of wash solution is stopped, but there is still uninterrupted fluid and electrical communication between reference electrode 108, passage 109, and sensor array 100. Some of the reagent flowing through passage 109 may diffuse into passage 111, but the distance between reference electrode 108 and the junction between passages 109 and 111 is selected so that little or no amount of the reagents flowing in common passage 109 reach reference electrode 108. This configuration has the advantage of ensuring that reference electrode 108 is in contact with only a single fluid or reagent throughout an entire multi-step reaction process.

As shown in FIG. 26, flow chamber 105 is loaded with a flow cell that includes an inlet 102, an outlet 103, and a microwell array 107 which is operationally associated with a sensor array 100 that measures physical and/or chemical parameters in the microwells that provide information about the status of a reaction taking place therein; or in the case of empty wells, information about the physical and/or chemical environment in the flow cell. Each microwell may have a sensor for detecting an analyte or reaction property of interest. In this particular embodiment, the microwell array is integrated with the sensor array as a single chip. A flow cell can have a variety of designs for controlling the path and flow rate of reagents over the microwell array. This particular apparatus has an array controller 124 which receives information from sensor array 100 and reference electrode 108 via communication line 126. A user interface 128 provides an interface through which a user may interact with the apparatus.

Figure 27:
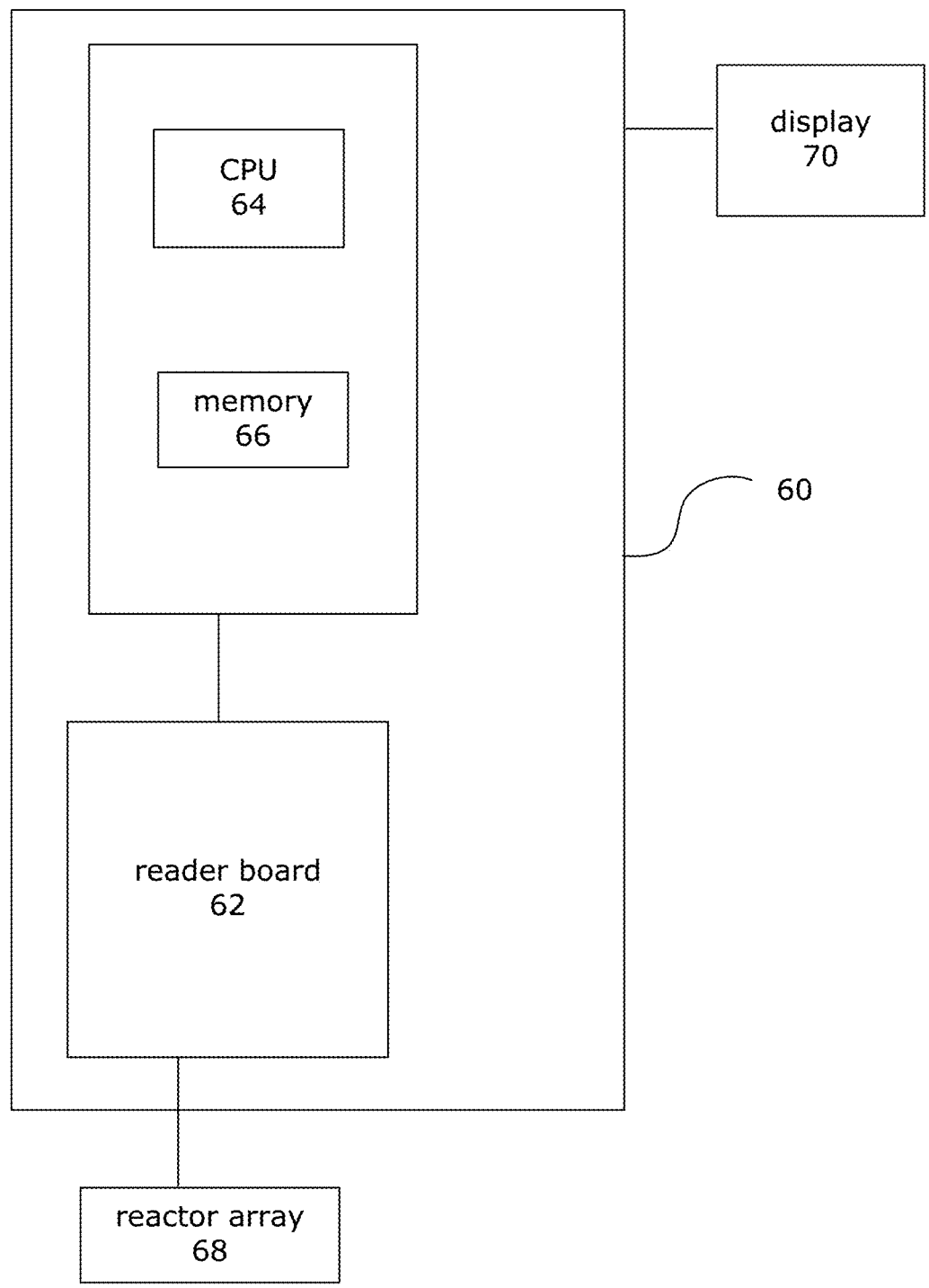
FIG. 27 shows an apparatus according to an exemplary embodiment.

An apparatus may be used to perform the above-described exemplary methods. The apparatus may be a computer that includes various components such as processor(s) and memory. An example of an apparatus of the present teachings is shown in FIG. 27. In some embodiments, the apparatus 60 may include one or more processors 64 and machine-readable memory 66. In some embodiments, the apparatus may include a display 70. In some embodiments, the apparatus may include a reader board 62 which is coupled to a reactor array 68. The reader board 62 may include various components used in signal processing, including analog-to-digital converters. In some embodiments the apparatus may be part of the sequencing apparatus. In other embodiments, the apparatus may be separate from the sequencing apparatus; in some embodiments the apparatus may be coupled to the sequencing apparatus.

Figure 28A:
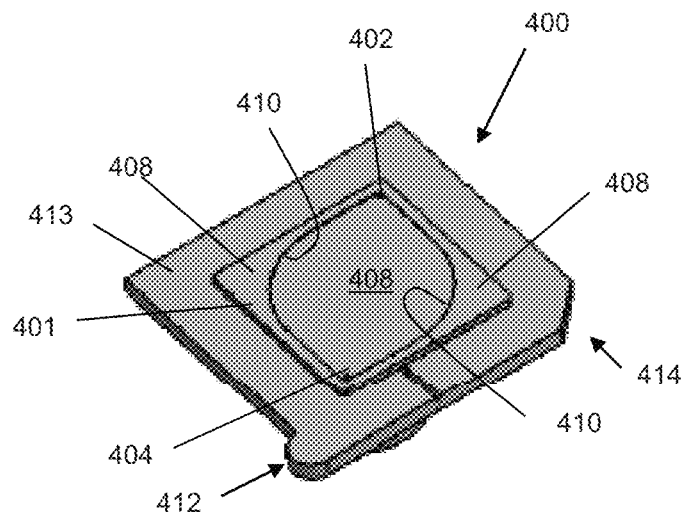
FIGS. 28A-28D show different views of an example flow cell.
Figure 28B:
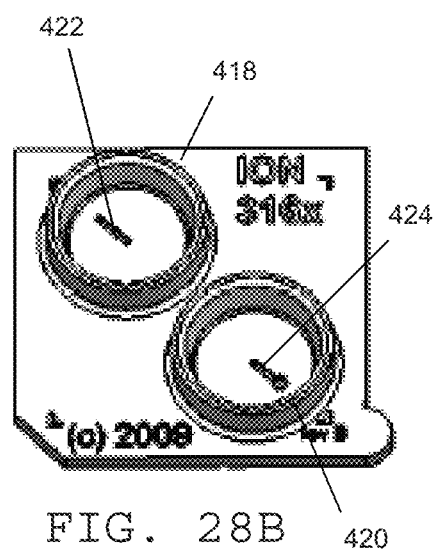
Figure 28C:
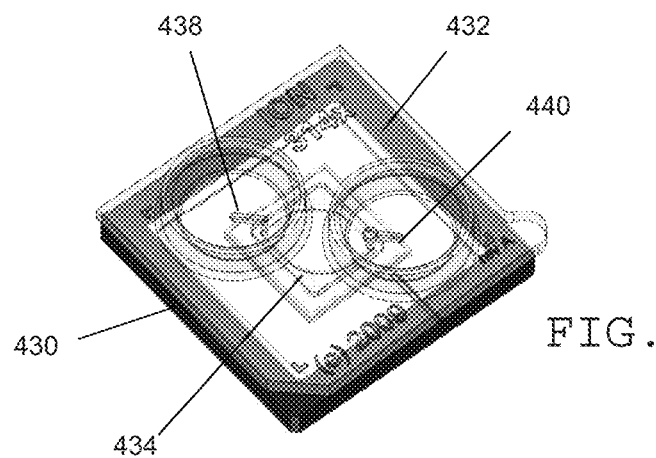
Figure 28D:
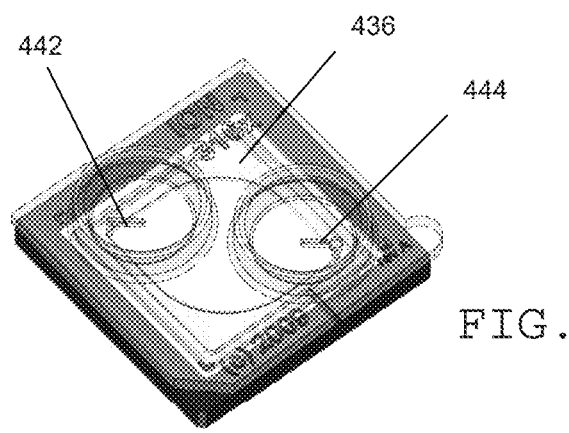

An example of a flow cell that can be used with the present invention is shown in FIGS. 28A-D. In this example, the flow cell is made by attaching a fluidic interface to a housing containing a sensor chip. Typically, an integrated microwell-sensor array (i.e., a sensor chip) is mounted in a housing or package that protects the chip and provides electrical contacts for communicating with other devices. A fluidics interface is designed to provide a cavity or flow chamber for reagents to pass through. FIG. 28A shows a bottom view of component 400. Component 400 is attached to a package containing a sensor array (as shown in FIGS. 28C and 28D). Ridge 401 is elevated from surface 413 and forms walls 410 of ellipsoidal flow chamber 408 when mated with chip housing 430 shown in FIG. 28C. Component 400 may be glued to chip housing 430 to form a fluid-tight seal. FIG. 28B shows a top view of component 400 showing inlet and outlet collars 418 and 420 that permit the flow cell to be connected to a fluidic system. Component 400 may be adapted to accommodate different sized chips with a simple design change, as illustrated by passages 422 and 424. Namely, for a small array 434 shown in FIG. 28C, a passage having an opening at the center of inlet collar 418 and of outlet collar 420 may be directed by such passage towards the center of component 400 to an inlet port and outlet port over chip housing 430. Likewise, for a large array 436, shown in FIG. 28D, similar passages 442 and 444 may be directed away from the center of component 400 and to the inlet and outlet of array 436. This has the advantage of providing a basic design that can be used with multiple sensor array sizes. Protruding tab 412 and bevel 414 ensure the correct orientation of a chip into a complementary socket or appliance for making fluidic and electrical connections to the rest of the apparatus. Other examples of flow cells that can be used with the present invention are described in U.S. Patent Application Publication No. 2009/0127589 (Rothberg et al.), which is incorporated by reference herein.

In pH-based detection methods, the production of hydrogen ions may be monotonically related to the number of contiguous complementary nucleotide bases in the template strands (as well as the total number of template strands with primer and polymerase that participate in an extension reaction). Thus, when there is a number of contiguous identical complementary nucleotide bases in the template (i.e. a homopolymer region), the number of hydrogen ions generated is generally proportional to the number of contiguous identical complementary bases. The corresponding output signals may sometimes be referred to as "1-mer", "2-mer", "3-mer" output signals, and so on, based on the expected number of repeating bases. The term "n-mer" refers to the number of contiguous identical complementary bases that are incorporated into the complementary strand on the template strand. Where the next base in the template is not complementary to the flowed nucleotide, generally no incorporation occurs and there is no substantial release of hydrogen ions (in which case, the output signal is sometimes referred to as a "0-mer" output signal).

Figure 29:
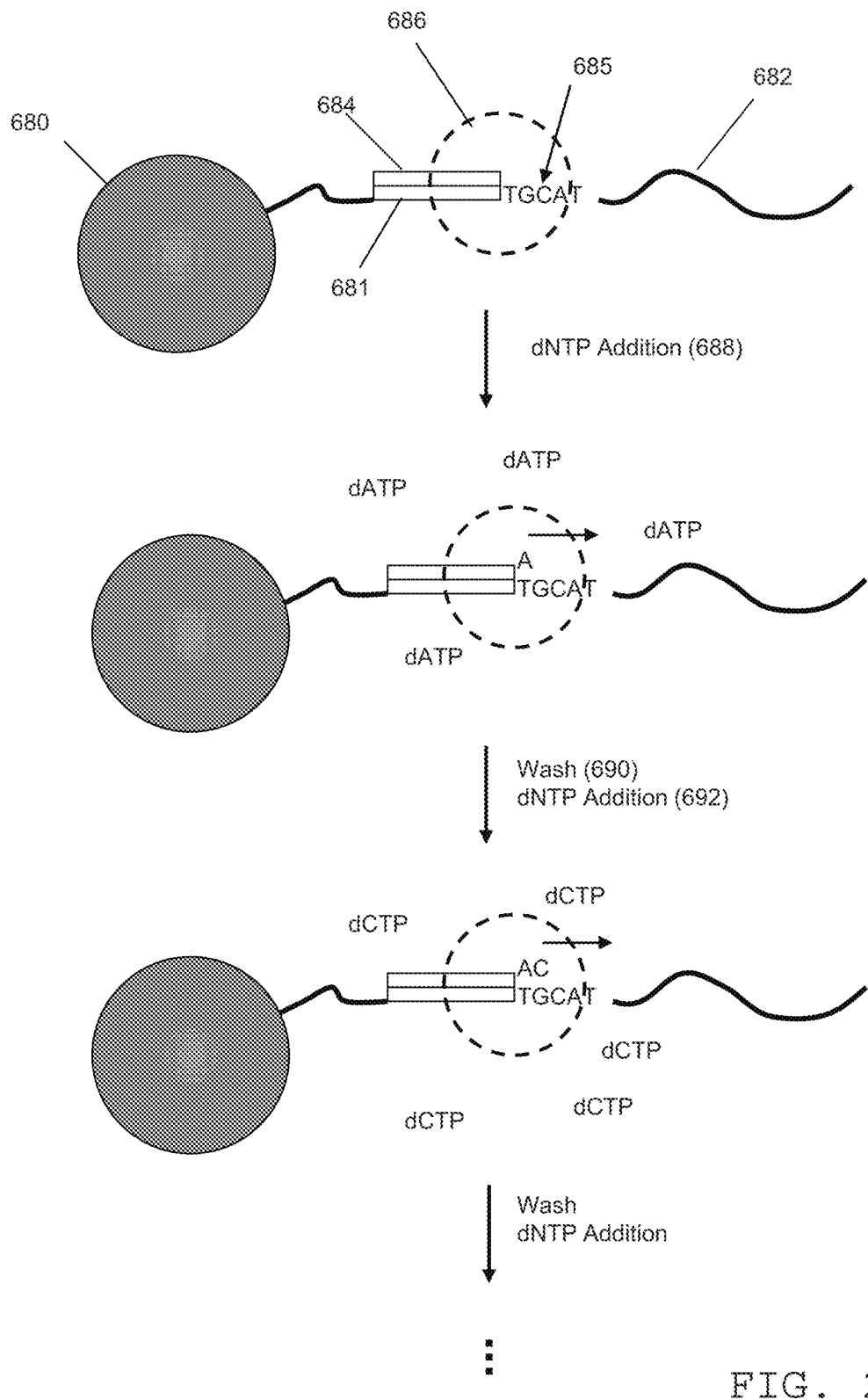
FIG. 29 shows an example of a sequencing-by-synthesis operation.

In each wash step of the cycle, a wash solution (typically having a predetermined pH) is used to remove residual nucleotide of the previous step in order to prevent miscorporations in later cycles. Usually, the four different kinds of nucleotides (e.g. dATP, dCTP, dGTP, and dTTP) are flowed sequentially to the reaction chambers, so that each reaction is exposed to one of the four different nucleotides for a given flow, with the exposure, incorporation, and detection steps being followed by a wash step. An example of this process is illustrated in FIG. 29, which shows a template polynucleotide strand 682 attached to a particle 680. Primer 684 is annealed to template strand 682 at its primer binding site 681. A DNA polymerase 686 is operably bound to the template-primer duplex. Template strand 682 has the sequence 685, which is awaiting complementary base incorporation. Upon the flow of the nucleotide (shown as dATP), polymerase 686 incorporates a nucleotide since "T" is the next nucleotide in template strand 682 (because the "T" base is complementary to the flowed dATP nucleotide). Wash step 690 follows, after which the next nucleotide (dCTP) is flowed 692. Optionally, after each step of flowing a nucleotide, the reaction chambers may be treated with a nucleotide-destroying agent (such as apyrase) to eliminate any residual nucleotides remaining in the chamber, which can cause spurious extensions in subsequent cycles. This process may be repeatedly continued with additional flows of nucleotide reagents.

In various embodiments, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context.

Polynucleotides may comprise the four natural nucleosides (e.g. deoxyadenosine, deoxycytidine, deoxyguanosine, deoxythymidine for DNA or their ribose counterparts for RNA) linked by phosphodiester linkages. However, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity (e.g. single stranded DNA, RNA/DNA duplex, or the like), then selection of an appropriate composition for the oligonucleotide or polynucleotide substrates is well within the knowledge of one of ordinary skill, especially with guidance from treatises such as Sambrook et al, MOLECULAR CLONING, 2nd ed. (Cold Spring Harbor Laboratory, New York, 1989), and like references.

"Polynucleotide" refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. As used herein, the term "oligonucleotide" refers to smaller polynucleotides, for example, having 5-40 monomeric units.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or rewriteable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, or the like, including any medium suitable for use in a computer. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

According to other embodiments of the present teachings, any one or more features of any one or more of the above-discussed teachings and/or exemplary embodiments may be performed or implemented at least partly using a cloud computing resource.

Those skilled in the art may appreciate from the foregoing description that the present teachings may be implemented in a variety of forms, and that the various embodiments may be implemented alone or in combination. Therefore, while the embodiments of the present teachings have been described in connection with particular examples thereof, the true scope of the embodiments and/or methods of the present teachings should not be so limited since other modifications will become apparent to the skilled practitioner upon a study of the drawings, specification, and following claims.

What is claimed is:

1. A method of sequencing a polynucleotide strand, comprising:
    flowing a series of nucleotide reagents onto a reactor array having multiple reaction confinement regions, wherein the polynucleotide strand is located in a loaded reaction confinement region of the reactor array;
    receiving signal data from the reactor array;
    determining a function that models an output signal of a representative empty reaction confinement region;
    determining a time-warped empty reaction confinement region function; and
    estimating a number of nucleotide incorporations using the time-warped empty reaction confinement region function.

2. The method of claim 1, wherein the time-warped empty reaction confinement region function is determined by applying a time transformation to the empty reaction confinement region function.

3. The method of claim 2, further comprising fitting the time-warped empty reaction confinement region function to an output signal from the loaded reaction confinement region that is representative of a first flow, wherein the first flow results in a non-incorporation event in the loaded reaction confinement region.

4. The method of claim 3, further comprising applying the fitted time-warped empty reaction confinement region function to the output signal for a second flow to the loaded reaction confinement region to obtain an incorporation signal for the second flow.

5. The method of claim 4, further comprising analyzing the incorporation signal to determine an estimate of a number of nucleotides incorporated into the polynucleotide strand.

6. The method of claim 2, wherein the time transformation is a polynomial function of time.

7. The method of claim 6, wherein the time transformation is a quadratic or cubic polynomial function of time.

8. The method of claim 2, wherein the time transformation is a linear function of time.

9. The method of claim 1, wherein the step of determining the empty reaction confinement region function comprises performing a spline fitting of the output signal from the representative empty reaction confinement region.

10. The method of claim 1, wherein the empty reaction confinement region function is a polynomial function of time.

11. The method of claim 4, further comprising fitting the time-warped empty reaction confinement region function to output signal from the loaded reaction confinement region representative of a third flow, wherein the third flow occurs later than the second flow and results in a non-incorporation event in the loaded reaction confinement region.

12. The method of claim 4, wherein the time transformation comprises a parameter, and further comprising:
    obtaining an output signal from the loaded reaction confinement region that is representative of a third flow, wherein the third flow occurs later than the second flow and results in a non-incorporation event in the loaded reaction confinement region;
    obtaining a derivative of the output signal for the third flow; and
    adjusting the parameter of the time transformation using the derivative.

13. The method of claim 4, wherein the polynucleotide strand includes a portion having a known sequence, and wherein the first flow is over the portion having the known sequence.

14. The method of claim 4, wherein the step of fitting the time-warped empty reaction confinement region function comprises minimizing a difference between the output signal from the loaded reaction confinement region and a signal predicted by the time-warped empty reaction confinement region function.

15. The method of claim 4, wherein the incorporation signal is obtained by subtracting the time-warped empty reaction confinement region function from the output signal for the second flow.

16. The method of claim 4, wherein the incorporation signal is obtained by solving a model for an output signal from the loaded reaction confinement region, wherein the output signal model comprises a background component and an incorporation signal component, wherein the background component is the fitted time-warped empty reaction confinement region function.

17. The method of claim 4, further comprising:
comparing the incorporation signal to a library of incorporation signal shapes comprising multiple signal shapes that are associated with different n-mer lengths; and
based on the comparison, determining an estimate of the number of nucleotides incorporated into the polynucleotide strand.

18. The method of claim 4, further comprising:
determining a function for the incorporation signal, wherein the function includes a parameter for the n-mer length;
fitting the incorporation signal function to the incorporation signal to solve for the parameter for the n-mer length; and
using the parameter for the n-mer length to estimate the number of nucleotides incorporated into the polynucleotide strand.

19. A sequencing apparatus comprising:
a machine-readable memory; and
a processor configured to execute machine-readable instructions, said instructions which when executed cause the apparatus to:
  receive signal data relating to chemical reactions resulting from the flow of a series of nucleotide reagents onto a reactor array having multiple reaction confinement regions, wherein a polynucleotide strand is located in a loaded reaction confinement region of the reactor array;
  determine a function that models an output signal of a representative empty reaction confinement region, wherein the function is stored in a computer memory;
  determine a time-warped empty reaction confinement region function;
  estimate a number of nucleotide incorporations using the time-warped empty reaction confinement region function; and
  store the estimated number of nucleotide incorporations in the memory.

20. A non-transitory machine-readable storage medium comprising instructions which, when executed by a processor, cause the processor to:
  receive signal data relating to chemical reactions resulting from the flow of a series of nucleotide reagents onto a reactor array having multiple reaction confinement regions, wherein a polynucleotide strand is located in a loaded reaction confinement region of the reactor array;
  determine a function that models an output signal of a representative empty reaction confinement region, wherein the function is stored in a computer memory;
  determine a time-warped empty reaction confinement region function;
  estimate a number of nucleotide incorporations using the time-warped empty reaction confinement region function; and
  store the estimated number of nucleotide incorporations in the memory.

* * * * *